United States Patent
Austin et al.

(10) Patent No.: US 11,896,270 B2
(45) Date of Patent: *Feb. 13, 2024

(54) SYSTEMS AND METHODS FOR USING POLYAXIAL PLATES

(71) Applicant: Smith & Nephew, Inc., Memphis, TN (US)

(72) Inventors: Gene Edward Austin, Bartlett, TN (US); Jon A. Harmon, Byhalia, MS (US); Timothy J. Petteys, Bartlett, TN (US); Thomas A. Russell, Collierville, TN (US); Paul Tornetta, Chestnut Hill, MA (US); William M. Ricci, Richmond Heights, MO (US)

(73) Assignee: SMITH & NEPHEW, INC., Memphis, TN (US)

( * ) Notice: Subject to any disclaimer, the term of this patent is extended or adjusted under 35 U.S.C. 154(b) by 624 days.

This patent is subject to a terminal disclaimer.

(21) Appl. No.: 16/916,668

(22) Filed: Jun. 30, 2020

(65) Prior Publication Data

US 2020/0323570 A1    Oct. 15, 2020

Related U.S. Application Data

(63) Continuation of application No. 15/970,779, filed on May 3, 2018, now Pat. No. 10,736,680, which is a (Continued)

(51) Int. Cl.
*A61B 17/80* (2006.01)
*A61B 17/74* (2006.01)
(Continued)

(52) U.S. Cl.
CPC .......... *A61B 17/8052* (2013.01); *A61B 17/74* (2013.01); *A61B 17/8033* (2013.01);
(Continued)

(58) Field of Classification Search
CPC .................. A61B 17/8605; A61B 17/8052
See application file for complete search history.

(56) References Cited

U.S. PATENT DOCUMENTS

| 300,146 A | 6/1884 | Sinnett |
| 351,751 A | 11/1886 | Douglas |
| (Continued) | | |

FOREIGN PATENT DOCUMENTS

| AU | 754857 B2 | 11/2002 |
| AU | 2003254686 B2 | 3/2005 |
| (Continued) | | |

OTHER PUBLICATIONS

Smith & Nephew Brochure entitled "Surgical Technique PERI-LOC VLP Variable-Angle Locked Plating System," pp. 1-32 (Nov. 2007).

(Continued)

*Primary Examiner* — Andrew Yang
(74) *Attorney, Agent, or Firm* — KDW Firm PLLC

(57) ABSTRACT

Certain embodiments of the invention provide plates for treating periarticular fractures or other non-full body weight bearing applications that combine polyaxial fixation with a low profile and enhanced contouring that more closely conforms to bone. Such plates can be designed to achieve buttressing effect and/or to be used in a reinforcement mode. Other features can be combined with these. Such plates can be created for use on bone sites such as on a tibia, fibula, metatarsal, calcaneous, other foot bone, humerus, radius, ulna, spinal, maxillofacial, as well as sites on other bones.

18 Claims, 46 Drawing Sheets

Related U.S. Application Data continuation of application No. 15/706,877, filed on Sep. 18, 2017, now Pat. No. 10,092,337, which is a continuation of application No. 14/535,573, filed on Nov. 7, 2014, now Pat. No. 9,795,424, which is a continuation of application No. 13/774,721, filed on Feb. 22, 2013, now Pat. No. 8,888,824, said application No. 13/774,721 is a continuation of application No. 12/069,331, filed as application No. PCT/US2006/028778 on Jul. 25, 2006, now Pat. No. 8,382,807, and a continuation-in-part of application No. 11/996,795, filed on Aug. 1, 2008, now Pat. No. 8,940,028.

(60) Provisional application No. 60/702,231, filed on Jul. 25, 2005.

(51) Int. Cl.
  *A61B 17/86* (2006.01)
  *A61B 17/00* (2006.01)

(52) U.S. Cl.
  CPC ...... *A61B 17/8057* (2013.01); *A61B 17/8061* (2013.01); *A61B 17/8605* (2013.01); *A61B 17/8085* (2013.01); *A61B 17/863* (2013.01); *A61B 2017/00004* (2013.01)

(56) References Cited

U.S. PATENT DOCUMENTS

| | | |
|---|---|---|
| 382,670 A | 5/1888 | Trovillion |
| 544,606 A | 8/1895 | Balsley |
| 545,331 A | 8/1895 | Balsley |
| 565,808 A | 8/1896 | Staples |
| 575,631 A | 1/1897 | Brooks |
| 583,158 A | 5/1897 | Upham |
| 637,990 A | 11/1899 | Hoepner |
| 651,949 A | 6/1900 | Lillie |
| 689,722 A | 12/1901 | Hoover |
| 766,270 A | 8/1904 | Lapham |
| 775,427 A | 11/1904 | Lusted, Sr. |
| 902,040 A | 10/1908 | Wyckoff |
| 1,025,008 A | 4/1912 | Miner |
| 1,105,105 A | 7/1914 | Sherman |
| 1,275,810 A | 8/1918 | White |
| 1,575,149 A | 3/1926 | Craig et al. |
| 1,755,588 A | 4/1930 | Bronk |
| 1,925,385 A | 9/1933 | Humes et al. |
| 2,010,913 A | 8/1935 | Bruce et al. |
| 2,133,859 A | 10/1938 | Hawley |
| 2,152,977 A | 4/1939 | Shindel |
| 2,388,921 A | 11/1945 | Kooiker |
| 2,501,978 A | 3/1950 | Wickman |
| 2,524,167 A | 10/1950 | Grande |
| 2,560,912 A | 7/1951 | Aitto |
| 2,667,194 A | 1/1954 | Fisher et al. |
| 2,756,791 A | 7/1956 | Ferrara |
| 3,056,441 A | 10/1962 | Helms |
| 3,279,510 A | 10/1966 | Dreyer et al. |
| 3,347,293 A | 10/1967 | Clark |
| 3,409,058 A | 11/1968 | La Pointe |
| 3,547,114 A | 12/1970 | Haboush |
| 3,552,389 A | 1/1971 | Allgower et al. |
| 3,630,261 A | 12/1971 | Gley |
| 3,662,797 A | 5/1972 | Healis |
| 3,668,972 A | 6/1972 | Allgower et al. |
| 3,716,050 A | 2/1973 | Johnston |
| 3,739,825 A | 6/1973 | Knox |
| 3,741,205 A | 6/1973 | Markolf et al. |
| 3,744,488 A | 7/1973 | Cox |
| 3,779,240 A | 12/1973 | Kondo |
| 3,782,432 A | 1/1974 | Allen |
| 3,866,607 A | 2/1975 | Forsyth et al. |
| 3,906,550 A | 6/1975 | Rostoker et al. |
| 3,935,762 A | 2/1976 | Tudisco |
| RE28,841 E | 6/1976 | Allgower et al. |
| 4,059,102 A | 11/1977 | Devas |
| 4,060,114 A | 11/1977 | Matsushima |
| 4,096,896 A | 6/1978 | Engel |
| 4,219,015 A | 8/1980 | Steinemann |
| 4,246,811 A | 1/1981 | Bondhus et al. |
| 4,263,904 A | 4/1981 | Judet |
| 4,338,926 A | 7/1982 | Kummer et al. |
| 4,364,382 A | 12/1982 | Mennen |
| 4,388,921 A | 6/1983 | Sutter et al. |
| 4,408,601 A | 10/1983 | Wenk |
| RE31,628 E | 7/1984 | Allgower et al. |
| 4,484,570 A | 11/1984 | Sutter et al. |
| 4,493,317 A | 1/1985 | Klaue |
| 4,513,744 A | 4/1985 | Klaue |
| 4,535,658 A | 8/1985 | Molinari |
| 4,564,007 A | 1/1986 | Coombs et al. |
| 4,565,193 A | 1/1986 | Streli |
| 4,573,458 A | 3/1986 | Lower |
| 4,683,878 A | 8/1987 | Carter |
| 4,704,929 A | 11/1987 | Osada |
| 4,791,918 A | 12/1988 | Von Hasselbeck |
| 4,797,948 A | 1/1989 | Wolter |
| 4,838,252 A | 6/1989 | Klaue |
| 4,927,421 A | 5/1990 | Goble et al. |
| 4,978,349 A | 12/1990 | Frigg |
| 4,988,350 A | 1/1991 | Herzberg |
| 5,002,544 A | 3/1991 | Klaue et al. |
| 5,006,120 A | 4/1991 | Carter |
| 5,041,114 A | 8/1991 | Chapman et al. |
| 5,053,036 A | 10/1991 | Perren et al. |
| 5,085,660 A | 2/1992 | Lin |
| 5,129,901 A | 7/1992 | Decoste |
| 5,151,103 A | 9/1992 | Tepic et al. |
| 5,190,544 A | 3/1993 | Chapman et al. |
| 5,192,281 A | 3/1993 | de la Caffiniere |
| 5,197,966 A | 3/1993 | Sommerkarnp |
| 5,198,308 A | 3/1993 | Shetty et al. |
| 5,237,893 A | 8/1993 | Ryder et al. |
| 5,259,398 A | 11/1993 | Vrespa |
| 5,269,784 A | 12/1993 | Mast |
| 5,275,601 A | 1/1994 | Gogolewski et al. |
| 5,304,180 A | 4/1994 | Slocurn |
| 5,312,410 A | 5/1994 | Miller et al. |
| 5,324,290 A | 6/1994 | Zdeblick et al. |
| 5,324,291 A | 6/1994 | Ries et al. |
| 5,356,410 A | 10/1994 | Penning |
| 5,360,452 A | 11/1994 | Engelhardt et al. |
| 5,364,398 A | 11/1994 | Chapman et al. |
| 5,364,399 A | 11/1994 | Lowery et al. |
| 5,395,374 A | 3/1995 | Miller et al. |
| 5,415,658 A | 5/1995 | Kilpela et al. |
| 5,423,820 A | 6/1995 | Miller et al. |
| 5,423,826 A | 6/1995 | Coates et al. |
| 5,429,641 A | 7/1995 | Ross et al. |
| 5,431,659 A | 7/1995 | Ross et al. |
| 5,470,333 A | 11/1995 | Ray |
| 5,474,553 A | 12/1995 | Baumgart |
| 5,487,743 A | 1/1996 | Laurain et al. |
| 5,514,138 A | 5/1996 | McCarthy |
| 5,520,690 A | 5/1996 | Errico et al. |
| 5,522,902 A | 6/1996 | Yuan et al. |
| 5,527,310 A | 6/1996 | Cole et al. |
| 5,531,143 A | 7/1996 | Habermehl et al. |
| 5,531,746 A | 7/1996 | Errico et al. |
| 5,531,748 A | 7/1996 | de la Caffiniere |
| 5,534,932 A | 7/1996 | Van de Wateriaat et al. |
| 5,536,127 A | 7/1996 | Penning |
| 5,569,253 A | 10/1996 | Farris et al. |
| 5,578,034 A | 11/1996 | Estes |
| 5,591,168 A | 1/1997 | Judet et al. |
| 5,601,553 A | 2/1997 | Trebing et al. |
| 5,607,426 A | 3/1997 | Ralph et al. |
| 5,607,428 A | 3/1997 | Lin |
| 5,643,265 A | 7/1997 | Errico et al. |
| 5,647,873 A | 7/1997 | Errico et al. |
| 5,665,088 A | 9/1997 | Gil et al. |

(56) References Cited

U.S. PATENT DOCUMENTS

| | | |
|---|---|---|
| 5,665,089 A | 9/1997 | Dall et al. |
| 5,676,667 A | 10/1997 | Hausman |
| 5,702,399 A | 12/1997 | Kilpela et al. |
| 5,709,686 A | 1/1998 | Talos et al. |
| 5,713,900 A | 2/1998 | Benzel et al. |
| 5,725,588 A | 3/1998 | Errico et al. |
| 5,733,287 A | 3/1998 | Tepic et al. |
| 5,735,853 A | 4/1998 | Olerud |
| 5,741,258 A | 4/1998 | Klaue et al. |
| 5,749,872 A | 5/1998 | Kyle et al. |
| 5,769,850 A | 6/1998 | Chin |
| 5,772,662 A | 6/1998 | Chapman et al. |
| 5,776,196 A | 7/1998 | Matsuzaki et al. |
| 5,788,697 A | 8/1998 | Kilpela et al. |
| 5,797,912 A | 8/1998 | Runciman et al. |
| 5,810,823 A | 9/1998 | Klaue et al. |
| 5,824,247 A | 10/1998 | Tunc |
| 5,876,402 A | 3/1999 | Errico et al. |
| 5,888,204 A | 3/1999 | Ralph et al. |
| 5,893,856 A | 4/1999 | Jacob et al. |
| 5,902,305 A | 5/1999 | Beger et al. |
| 5,904,683 A | 5/1999 | Pohndorf et al. |
| 5,904,684 A | 5/1999 | Rooks |
| 5,925,047 A | 7/1999 | Errico et al. |
| 5,935,130 A | 8/1999 | Kilpela et al. |
| 5,935,133 A | 8/1999 | Wagner et al. |
| 5,938,664 A | 8/1999 | Winquist et al. |
| 5,954,722 A | 9/1999 | Bono |
| 5,960,681 A | 10/1999 | Anderson et al. |
| 5,961,524 A | 10/1999 | Crombie |
| 5,964,769 A | 10/1999 | Wagner et al. |
| 5,968,046 A | 10/1999 | Castleman |
| 5,968,047 A | 10/1999 | Reed |
| 5,976,141 A | 11/1999 | Haag et al. |
| 6,016,727 A | 1/2000 | Morgan |
| 6,019,762 A | 2/2000 | Cole |
| 6,022,352 A | 2/2000 | Vandewalle |
| 6,053,921 A | 4/2000 | Wagner et al. |
| 6,096,040 A | 8/2000 | Esser |
| 6,129,730 A | 10/2000 | Bono et al. |
| 6,176,861 B1 | 1/2001 | Bernstein et al. |
| 6,183,475 B1 | 2/2001 | Lester et al. |
| 6,193,721 B1 | 2/2001 | Michelson |
| 6,206,881 B1 | 3/2001 | Frigg et al. |
| 6,214,049 B1 | 4/2001 | Gayer et al. |
| 6,228,085 B1 | 5/2001 | Theken et al. |
| 6,235,033 B1 | 5/2001 | Brace et al. |
| RE37,249 E | 6/2001 | Leibinger et al. |
| 6,258,092 B1 | 7/2001 | Dall |
| 6,273,889 B1 | 8/2001 | Richelsoph |
| 6,302,001 B1 | 10/2001 | Karie |
| 6,302,883 B1 | 10/2001 | Bono |
| 6,306,136 B1 | 10/2001 | Baccelli |
| 6,306,140 B1 | 10/2001 | Siddiqui |
| 6,309,393 B1 | 10/2001 | Tepic et al. |
| 6,321,562 B1 | 11/2001 | Wolter |
| 6,342,055 B1 | 1/2002 | Eisermann et al. |
| 6,355,041 B1 | 3/2002 | Martin |
| 6,355,043 B1 | 3/2002 | Adam |
| 6,358,250 B1 | 3/2002 | Orbay |
| 6,361,537 B1 | 3/2002 | Anderson |
| 6,364,885 B1 | 4/2002 | Kilpela et al. |
| 6,370,091 B1 | 4/2002 | Kuroda |
| 6,379,359 B1 | 4/2002 | Dahners |
| 6,386,808 B2 | 5/2002 | Fujii et al. |
| 6,391,030 B1 | 5/2002 | Wagner et al. |
| 6,413,259 B1 | 7/2002 | Lyons et al. |
| 6,428,542 B1 | 8/2002 | Michelson |
| 6,436,100 B1 | 8/2002 | Berger |
| 6,440,135 B2 | 8/2002 | Orbay et al. |
| 6,454,770 B1 | 8/2002 | Klaue |
| 6,454,769 B2 | 9/2002 | Wagner et al. |
| 6,468,278 B1 | 10/2002 | Muckter |
| 6,475,218 B2 | 11/2002 | Gournay et al. |
| 6,506,191 B1 | 1/2003 | Joos |
| 6,520,965 B2 | 2/2003 | Chervitz et al. |
| 6,524,238 B2 | 2/2003 | Velikaris et al. |
| 6,527,776 B1 | 3/2003 | Michelson |
| 6,558,387 B2 | 5/2003 | Errico et al. |
| 6,575,975 B2 | 6/2003 | Brace et al. |
| 6,595,993 B2 | 7/2003 | Donno et al. |
| 6,595,994 B2 | 7/2003 | Kilpela et al. |
| 6,605,090 B1 | 8/2003 | Trieu et al. |
| 6,623,486 B1 | 9/2003 | Weaver et al. |
| 6,669,700 B1 | 12/2003 | Farris et al. |
| 6,669,701 B2 | 12/2003 | Steiner et al. |
| 6,682,531 B2 | 1/2004 | Winquist et al. |
| 6,682,533 B1 | 1/2004 | Dinsdale et al. |
| 6,684,741 B2 | 2/2004 | Blackston |
| 6,689,133 B2 | 2/2004 | Morrison et al. |
| 6,692,581 B2 | 2/2004 | Tong et al. |
| 6,719,759 B2 | 4/2004 | Wagner et al. |
| 6,730,091 B1 | 5/2004 | Pfefferle et al. |
| 6,755,829 B1 | 6/2004 | Bono et al. |
| 6,767,351 B2 | 7/2004 | Orbay et al. |
| 6,780,186 B2 | 8/2004 | Errico et al. |
| 6,821,278 B2 | 11/2004 | Frigg et al. |
| 6,866,665 B2 | 3/2005 | Orbay |
| 6,893,443 B2 | 5/2005 | Frigg et al. |
| 6,893,444 B2 | 5/2005 | Orbay |
| 6,916,320 B2 | 7/2005 | Michelson |
| 6,945,975 B2 | 9/2005 | Dalton |
| 6,955,677 B2 | 10/2005 | Dahners |
| 6,960,213 B2 | 11/2005 | Chervitz et al. |
| 6,969,390 B2 | 11/2005 | Michelson |
| 6,973,860 B2 | 12/2005 | Nish |
| 6,974,461 B1 | 12/2005 | Wolter |
| 6,979,334 B2 | 12/2005 | Dalton |
| 7,073,415 B2 | 7/2006 | Casutt et al. |
| 7,074,221 B2 | 7/2006 | Michelson |
| 7,128,744 B2 | 10/2006 | Weaver et al. |
| 7,172,593 B2 | 2/2007 | Trieu et al. |
| 7,179,260 B2 | 2/2007 | Gerlach et al. |
| 7,230,039 B2 | 6/2007 | Trieu et al. |
| 7,250,053 B2 | 7/2007 | Orbay |
| 7,250,054 B2 | 7/2007 | Allen et al. |
| 7,255,701 B2 | 8/2007 | Allen et al. |
| 7,282,053 B2 | 10/2007 | Orbay |
| 7,294,130 B2 | 11/2007 | Orbay |
| 7,341,589 B2 | 3/2008 | Weaver et al. |
| 7,419,714 B1 | 9/2008 | Magerl et al. |
| 7,637,928 B2 * | 12/2009 | Fernandez ......... A61B 17/8047 606/289 |
| 7,695,472 B2 | 4/2010 | Young |
| 7,722,653 B2 | 5/2010 | Young et al. |
| 7,766,948 B1 | 8/2010 | Leung |
| 8,105,367 B2 | 1/2012 | Austin et al. |
| 8,992,581 B2 | 3/2015 | Austin et al. |
| 2001/0037112 A1 | 11/2001 | Brace et al. |
| 2001/0047174 A1 | 11/2001 | Donno et al. |
| 2002/0013587 A1 | 1/2002 | Winquist et al. |
| 2002/0045901 A1 | 4/2002 | Wagner et al. |
| 2002/0058940 A1 | 5/2002 | Frigg et al. |
| 2002/0058943 A1 | 5/2002 | Kippela et al. |
| 2002/0115742 A1 | 8/2002 | Trieu et al. |
| 2002/0143338 A1 | 10/2002 | Orbay et al. |
| 2002/0161370 A1 | 10/2002 | Frigg et al. |
| 2003/0040749 A1 | 2/2003 | Grabowski et al. |
| 2003/0057590 A1 | 3/2003 | Loher et al. |
| 2003/0060827 A1 | 3/2003 | Coughin |
| 2003/0105462 A1 | 6/2003 | Haider |
| 2003/0183335 A1 | 10/2003 | Winniczek et al. |
| 2004/0010257 A1 | 1/2004 | Cachia et al. |
| 2004/0030342 A1 | 2/2004 | Trieu et al. |
| 2004/0044345 A1 | 3/2004 | DeMoss et al. |
| 2004/0059334 A1 | 3/2004 | Weaver et al. |
| 2004/0059335 A1 | 3/2004 | Weaver et al. |
| 2004/0073218 A1 | 4/2004 | Dahners |
| 2004/0087954 A1 | 5/2004 | Allen et al. |
| 2004/0097942 A1 | 5/2004 | Allen et al. |
| 2004/0138666 A1 | 7/2004 | Molz et al. |
| 2004/0181228 A1 | 9/2004 | Wagner et al. |
| 2004/0199169 A1 | 10/2004 | Koons et al. |
| 2004/0213645 A1 | 10/2004 | Kovac |

(56) References Cited

U.S. PATENT DOCUMENTS

| | | | |
|---|---|---|---|
| 2004/0215195 A1 | 10/2004 | Shipp et al. | |
| 2004/0220570 A1 | 11/2004 | Frigg | |
| 2004/0236332 A1 | 11/2004 | Frigg | |
| 2004/0260306 A1 | 12/2004 | Fallin et al. | |
| 2005/0010220 A1 | 1/2005 | Casutt et al. | |
| 2005/0010226 A1 | 1/2005 | Grady et al. | |
| 2005/0027298 A1 | 2/2005 | Michelson | |
| 2005/0043736 A1 | 2/2005 | Mathieu et al. | |
| 2005/0049593 A1 | 3/2005 | Duong et al. | |
| 2005/0049594 A1 | 3/2005 | Wack et al. | |
| 2005/0070904 A1 | 3/2005 | Gerlach et al. | |
| 2005/0080421 A1 | 4/2005 | Weaver et al. | |
| 2005/0107796 A1 | 5/2005 | Gerlach et al. | |
| 2005/0149026 A1 | 7/2005 | Butler et al. | |
| 2005/0165400 A1 | 7/2005 | Fernandez | |
| 2005/0192580 A1 | 9/2005 | Dalton | |
| 2005/0234457 A1 | 10/2005 | Jarmes et al. | |
| 2005/0261688 A1 | 11/2005 | Grady et al. | |
| 2005/0277937 A1 | 12/2005 | Leung et al. | |
| 2005/0283154 A1 | 12/2005 | Orbay et al. | |
| 2006/0004361 A1 | 1/2006 | Hayeck et al. | |
| 2006/0009770 A1 | 1/2006 | Speirs et al. | |
| 2006/0009771 A1 | 1/2006 | Orbay et al. | |
| 2006/0095040 A1 | 5/2006 | Schlienger et al. | |
| 2006/0116678 A1 | 5/2006 | Impellizzeri | |
| 2006/0122602 A1 | 6/2006 | Konieczynski et al. | |
| 2006/0129148 A1 | 6/2006 | Simmons et al. | |
| 2006/0129151 A1 | 6/2006 | Allen et al. | |
| 2006/0149265 A1 | 7/2006 | James et al. | |
| 2006/0165400 A1 | 7/2006 | Spencer | |
| 2006/0167464 A1 | 7/2006 | Allen et al. | |
| 2006/0200147 A1 | 9/2006 | Ensign et al. | |
| 2006/0235400 A1 | 10/2006 | Schneider | |
| 2006/0235410 A1 | 10/2006 | Ralph et al. | |
| 2006/0259039 A1 | 11/2006 | Pitkanen et al. | |
| 2007/0010817 A1 | 1/2007 | de Coninck | |
| 2007/0043366 A1 | 2/2007 | Pfefferle et al. | |
| 2007/0093836 A1 | 4/2007 | Derouet | |
| 2007/0161995 A1 | 7/2007 | Trautwein et al. | |
| 2007/0162016 A1 | 7/2007 | Matityahu | |
| 2007/0162020 A1 | 7/2007 | Gerlach et al. | |
| 2007/0185488 A1 | 8/2007 | Pohjonen et al. | |
| 2007/0213828 A1 | 9/2007 | Trieu et al. | |
| 2007/0233106 A1 | 10/2007 | Horan et al. | |
| 2007/0260244 A1 | 11/2007 | Wolter et al. | |
| 2007/0270691 A1 | 11/2007 | Bailey et al. | |
| 2007/0270832 A1 | 11/2007 | Moore | |
| 2007/0270833 A1 | 11/2007 | Bonutti et al. | |
| 2007/0276383 A1 | 11/2007 | Rayhack | |
| 2008/0021474 A1 | 1/2008 | Bonutti et al. | |
| 2008/0039845 A1 | 2/2008 | Bonutti et al. | |
| 2008/0086129 A1 | 4/2008 | Lindermann et al. | |
| 2008/0140130 A1 | 6/2008 | Chan et al. | |
| 2008/0154367 A1 | 6/2008 | Justis et al. | |
| 2008/0154368 A1 | 6/2008 | Justis et al. | |
| 2008/0154373 A1 | 6/2008 | Protopsaltis et al. | |
| 2008/0167717 A9 | 7/2008 | Trieu et al. | |
| 2008/0208259 A1 | 8/2008 | Gilbert et al. | |
| 2008/0300637 A1 | 12/2008 | Austin et al. | |
| 2009/0024161 A1 | 1/2009 | Bonutti et al. | |
| 2009/0076553 A1 | 3/2009 | Wolter et al. | |
| 2009/0088807 A1 | 4/2009 | Castaneda et al. | |
| 2009/0143824 A1 | 6/2009 | Austin et al. | |
| 2009/0149888 A1 | 6/2009 | Abdelgany | |
| 2009/0192549 A1 | 7/2009 | Sanders et al. | |
| 2009/0312803 A1 | 12/2009 | Austin et al. | |
| 2012/0143193 A1 | 6/2012 | Hulliger | |
| 2012/0265253 A1 | 10/2012 | Conley et al. | |

FOREIGN PATENT DOCUMENTS

| | | |
|---|---|---|
| CA | 2047521 A1 | 1/1992 |
| CA | 2408327 C | 3/2001 |
| CA | 2536960 A1 | 3/2005 |
| CH | 611147 A5 | 5/1979 |
| CN | 1373646 A | 10/2002 |
| CN | 1380043 A | 11/2002 |
| CN | 1188086 C | 2/2005 |
| CN | 1331572 C | 8/2007 |
| CN | 101022767 A | 8/2007 |
| DE | 323214 C | 7/1920 |
| DE | 2602900 C3 | 4/1979 |
| DE | 3513600 A1 | 10/1986 |
| DE | 3804749 A1 | 3/1989 |
| DE | 3832343 A1 | 3/1990 |
| DE | 9000161 U | 4/1990 |
| DE | 4341980 A1 | 6/1995 |
| DE | 4343117 A1 | 6/1995 |
| DE | 4438261 C1 | 9/1995 |
| DE | 4438264 C2 | 11/1996 |
| DE | 19629011 A1 | 1/1998 |
| DE | 19962317 A1 | 3/2001 |
| DE | 102004035546 A1 | 2/2006 |
| DE | 19858889 B4 | 8/2008 |
| EP | 0201024 A1 | 11/1986 |
| EP | 0207884 A2 | 1/1987 |
| EP | 0274713 A1 | 7/1988 |
| EP | 0355035 A2 | 2/1990 |
| EP | 0468192 A3 | 4/1992 |
| EP | 0486762 B1 | 5/1995 |
| EP | 0530585 B1 | 12/1995 |
| EP | 0705572 A2 | 4/1996 |
| EP | 0760632 A1 | 3/1997 |
| EP | 0799124 B1 | 8/2001 |
| EP | 1143867 A1 | 10/2001 |
| EP | 1211992 A1 | 6/2002 |
| EP | 1211993 A1 | 6/2002 |
| EP | 1211994 A2 | 6/2002 |
| EP | 1330209 A2 | 7/2003 |
| EP | 08288459 B1 | 9/2003 |
| EP | 1364623 A1 | 11/2003 |
| EP | 1404492 A1 | 4/2004 |
| EP | 1169971 B1 | 10/2004 |
| EP | 1649819 A1 | 4/2006 |
| EP | 1658015 A1 | 5/2006 |
| EP | 1711114 A2 | 10/2006 |
| EP | 1093385 B1 | 12/2006 |
| EP | 1764054 A1 | 3/2007 |
| EP | 1776055 A1 | 4/2007 |
| EP | 1813292 A1 | 8/2007 |
| EP | 1857073 A1 | 11/2007 |
| EP | 1718229 B1 | 4/2008 |
| EP | 1931268 A1 | 6/2008 |
| EP | 2019639 A1 | 2/2009 |
| EP | 1988837 A4 | 12/2011 |
| FR | 2233973 A1 | 1/1975 |
| FR | 2254298 A1 | 7/1975 |
| FR | 2405062 A1 | 5/1979 |
| FR | 2405705 A1 | 5/1979 |
| FR | 2405706 A1 | 5/1979 |
| FR | 2496429 A3 | 6/1982 |
| FR | 2501032 A1 | 9/1982 |
| FR | 2501033 B1 | 10/1985 |
| FR | 2667913 A1 | 4/1992 |
| FR | 2698261 B1 | 3/1995 |
| FR | 2706763 B1 | 8/1995 |
| FR | 2739151 B1 | 11/1997 |
| FR | 2757370 A1 | 6/1998 |
| FR | 2802082 A1 | 6/2001 |
| FR | 2831792 A1 | 5/2003 |
| FR | 2890848 B1 | 11/2007 |
| GB | 580571 A | 9/1946 |
| JP | 2003509107 A | 3/2003 |
| NO | 1999061081 A1 | 12/1999 |
| RU | 2234878 C2 | 8/2004 |
| SU | 1279626 A1 | 12/1986 |
| TW | 477687 B | 3/2002 |
| WO | WO1989004150 A1 | 5/1989 |
| WO | WO1990007304 A1 | 7/1990 |
| WO | WO1996009014 A1 | 3/1996 |
| WO | WO1996019336 A1 | 6/1996 |
| WO | WO1996025892 A1 | 8/1996 |
| WO | WO1996029948 A1 | 10/1996 |
| WO | WO1997009000 A1 | 3/1997 |

(56) References Cited

FOREIGN PATENT DOCUMENTS

| | | |
|---|---|---|
| WO | WO1998034553 A1 | 8/1998 |
| WO | WO1998034556 A1 | 8/1998 |
| WO | WO1999005968 A1 | 2/1999 |
| WO | 1999025266 A1 | 5/1999 |
| WO | WO1999025266 A1 | 5/1999 |
| WO | 2000018309 A1 | 4/2000 |
| WO | 2000019264 A1 | 4/2000 |
| WO | 2000036984 A1 | 6/2000 |
| WO | 2000053110 A1 | 9/2000 |
| WO | 2000053111 A1 | 9/2000 |
| WO | 2000066012 A1 | 11/2000 |
| WO | 2001019267 A1 | 3/2001 |
| WO | 2001019268 A1 | 3/2001 |
| WO | 2001019264 A1 | 8/2001 |
| WO | 2001078615 A1 | 10/2001 |
| WO | 2001091660 A1 | 12/2001 |
| WO | 2002000127 A1 | 1/2002 |
| WO | 2002058574 A2 | 8/2002 |
| WO | 2002068009 A2 | 9/2002 |
| WO | 2002034159 A3 | 11/2002 |
| WO | 2002096309 A1 | 12/2002 |
| WO | 2003006210 A1 | 1/2003 |
| WO | 2003106110 A1 | 12/2003 |
| WO | 2004032726 A2 | 4/2004 |
| WO | 2004032751 A3 | 5/2004 |
| WO | 2004080318 A1 | 9/2004 |
| WO | 2004086990 A1 | 10/2004 |
| WO | 2004089233 A1 | 10/2004 |
| WO | 2005018471 A1 | 3/2005 |
| WO | 2005018472 A1 | 3/2005 |
| WO | 2005032386 A1 | 4/2005 |
| WO | 2005034722 A1 | 4/2005 |
| WO | 2005079685 A1 | 9/2005 |
| WO | 2005062902 A3 | 12/2005 |
| WO | 2006007965 A1 | 1/2006 |
| WO | 2006039636 A2 | 4/2006 |
| WO | 2006068775 A2 | 6/2006 |
| WO | WO2007014279 A1 | 2/2007 |
| WO | WO2007025520 A1 | 3/2007 |
| WO | WO2007041686 A1 | 4/2007 |
| WO | 2007014192 A3 | 5/2007 |
| WO | WO2007092869 A1 | 8/2007 |
| WO | WO2007130840 A1 | 11/2007 |
| WO | WO200802213 A1 | 1/2008 |
| WO | WO2008033742 A1 | 3/2008 |
| WO | WO2008064211 A1 | 5/2008 |
| WO | WO2008077137 A1 | 6/2008 |
| WO | WO2008079846 A1 | 7/2008 |
| WO | WO2008079864 A1 | 7/2008 |
| WO | WO2008116203 A1 | 12/2008 |
| WO | WO2009029908 A1 | 3/2009 |

OTHER PUBLICATIONS

Notice of Reasons for Rejection for Japanese Application No. 2016-083204, dated Dec. 25, 2017.
Decision of Rejection and Decision to Reject the Amendments for Japanese Patent Application No. 2016-083204 dated Jul. 13, 2018. English translation submitted.
Decision of Rejection for Japanese Application No. 2008-0524048, dated Oct. 30, 2011.
Office Action for U.S. Appl. No. 11/996,795, dated Nov. 21, 2012.
Office Action for U.S. Appl. No. 12/484,527, dated May 18, 2011, 10 pages.
Office Action for U.S. Appl. No. 12/484,527, dated Jan. 20, 2011, 9 pages.
DePuy brochure entitled "Every Surgeon has His or Her Own View," Stryker Numelock 11 Polyaxial Locking System, Operative Technique, Gtrauma Application, 6 pages (undated).
"Polyax Wide Freedom Surgical Technique Distal Femoral Locked Playing System," DePuy International Ltd., http://rcsed.ac.uk/fellows/Ivanresburg/classification/surgtech/depuy (2005).
Final Office Action for U.S. Appl. No. 12/069,331., dated Apr. 9, 2012.
Office Action for U.S. Appl. No. 11/996,795, dated Mar. 23, 2012.
International Preliminary Report on Patentability for International Application No. PCT/US2006/028778, dated Jan. 28, 2008, 9 pages.
Examiner's First Report on Australian Application No. 2006272646, dated Mar. 21, 2011, 4 pages.
Smith & Nephew Brochure entitled 'PERI-LOC VLP Variable-Angle Locked Plating System Distal Tibia Locking Plates,' 04 pages (Oct. 2007).
Smith & Nephew Brochure entitled 'PERI-LOC VLP Variable-Angle Locked Plating System Distal Fibula Locking Plates,' 04 pages (Oct. 2007).
Smith & Nephew Brochure entitled 'PERI-LOC VLP Variable-Angle Locked Plating System Proximal Tibia Locking Plates,' 04 pages (Oct. 2007).
Smith & Nephew Brochure entitled 'PERI•LOC VLP Variable-Angle Locked Plating System Proximal Tibia Variable-Angle Locking Plates,' 04 pages (Nov. 2007).
Smith & Nephew Brochure entitled 'PERI-LOC VLP Variable-Angle Locked Plating System Improved Torsional Fatigue Properties with Thin Locked Versus Non-Locked Plate Constructs for Fixation of Simulated Osteoporotic Distal Fibula Fractures,' 04 pages (Nov. 2007).
Winkelstabilitat, litos Unidirectional locking screw technology, Jan. 15, 2008, 5 pages http://www.litos.com/paqes/winkelsta bilitaet e.html.
"SMARTLock Locking Screw Technology," http://www.stryker.com/microimplants/products/cmf smartlock.phn, Mar. 14, 2004.
International Search Report for PCT /US2006/028778, dated Apr. 19, 2007.
"Fracture and Dislocation Compendium," Orthopaedic Trauma Association Committee for Coding and Classification, Journal of Orthopaedic Trauma, vol. 10, Suppl.,jp, v = ix, 1996.
English Abstract of JP 2002532185, Published Oct. 2, 2002.
English Abstract of ZA 200200992, Published Dec. 18, 2002, Applicant: Synthes Ag.
NCB@ Proximal Humerus Plating System, Surgical Technique, Zimmer, Inc. 2005.
Zimmer® NCB® Plating System, Zimmer, Inc. 2006.
NCB® Distal Femoral Plating System, Surgical Technique, Zimmer, Inc. 2005.
New Trauma Products from AO Development, News—No. 1, 2007.
Office Action for Japanese Application No. 2008-0524048 dated Oct. 25, 2011, 6 pages.
Office Action for U.S. Appl. No. 12/069,331 dated Aug. 23, 2011, 12 pages.
Office Action for U.S. Appl. No. 13/774,721, dated Aug. 22, 2013.
Fuchs, S., et al., "Titanium Fixative Plate System with Multidirectional Angular Stability in the Lower Leg and Foot," Trauma Berufskrankh, Mar. 2001 (Suppl 4): S447-S453, Springer-Verlag 2001, Certified English Translation Thereof.
Wolter, D., et al., "Titanium Internal Fixator for the Tibia," Trauma Berufskrankh, Mar. 2001 (Supp 2): S156-S161, Springer-Verlag 2001, Certified English Translation Thereof.
Jurgens, C., et al., "Special Indications for the Application of the Fixed Angle Internal Fixation in Femur Fractures," Trauma Berufskrankh (1999) 1 :387,391, Springer-Verlag 1999, Certified English Translation Thereof.
Fuchs, S., et al., "Clinical Experiences with a New Internal Titanium Fixator for Ventral Spondylodesis of the Cervical Spine," Trauma Berufskrankh (1999) 1 :382-386, Springer-Verlag 1999, Certified English Translation Thereof.
Kranz, H.-W., et al., "Internal Titanium Fixation of Tibial Pseudarthrosis, Malalignment, and Fractures," Trauma Berufskrankh (1999) 1 :356-360, Springer-Verlag 1999, Certified English Translation Thereof.
Bohmer, G., et al., "Ti Fix® Angularly Stable Condylar Plate," Trauma Berufskrankh (1999) 1 :351-355, Springer-Verlag 1999, Certified English Translation Thereof.
Wolter, D., et al., "Universal Internal Titanium Fixation Device," Trauma Berufskrankh (1999) 1:307-309, Springer- Verlag 1999, Certified English Translation Thereof.
Office Action for U.S. Appl. No. 13/524,506, dated Dec. 16, 1013.

(56) References Cited

OTHER PUBLICATIONS

Notice of Reasons for Rejection for Japanese Application No. 2013-037623, dated Mar. 3, 2014.
Australian Office Action in Application No. 2013202741, dated Feb. 3, 2014, 4 pages.
DePuy Orthopaedics, Inc., "Surgical Technique Distal Femoral Locked Plating System," Polyax Wide Angle Freedom (2005).
Notice of Reasons for Rejection for Japanese Application No. 2013-037623, dated Jan. 26, 2015.
Patent Examination Report No. 1 for Australian Application No. 2012271441, dated Jan. 11, 2016.
Decision of Rejection and Decision to Reject Amendments for Japanese Application No. 2013-037623, dated Nov. 30, 2015.
Office Action for U.S. Appl. No. 14/671,499, dated Jun. 2, 2016.
Office Action for U.S. Appl. No. 13/524,506, dated May 27, 2016.
Office Action for U.S. Appl. No. 14/605,651, dated Mar. 14, 2016.
Appeal Decision for Japanese Application No. 2013-144121 (Appeal No. 2016-5758}, dated Jan. 4, 2017.
Office Action for U.S. Appl. No. 14/605,651, dated Oct. 6, 2016.
Examination Report No. 1 for Standard Patent Application issued in Australian Application No. 2016200491 dated Jan. 24, 2017.
Examination Report No. 1 for Standard Patent Application issued in Australian Application No. 2016200489 dated Jan. 24, 2017.
Examination Report No. 1 for Standard Patent Application for Australian Application No. 2016200490 dated Mar. 1, 2017.

\* cited by examiner

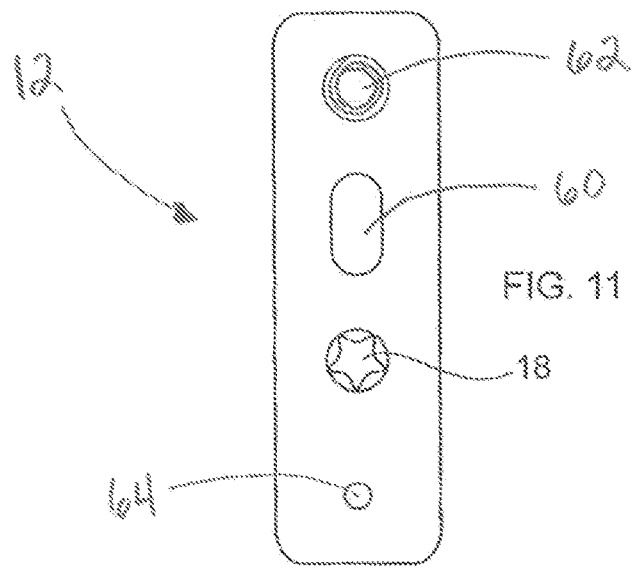
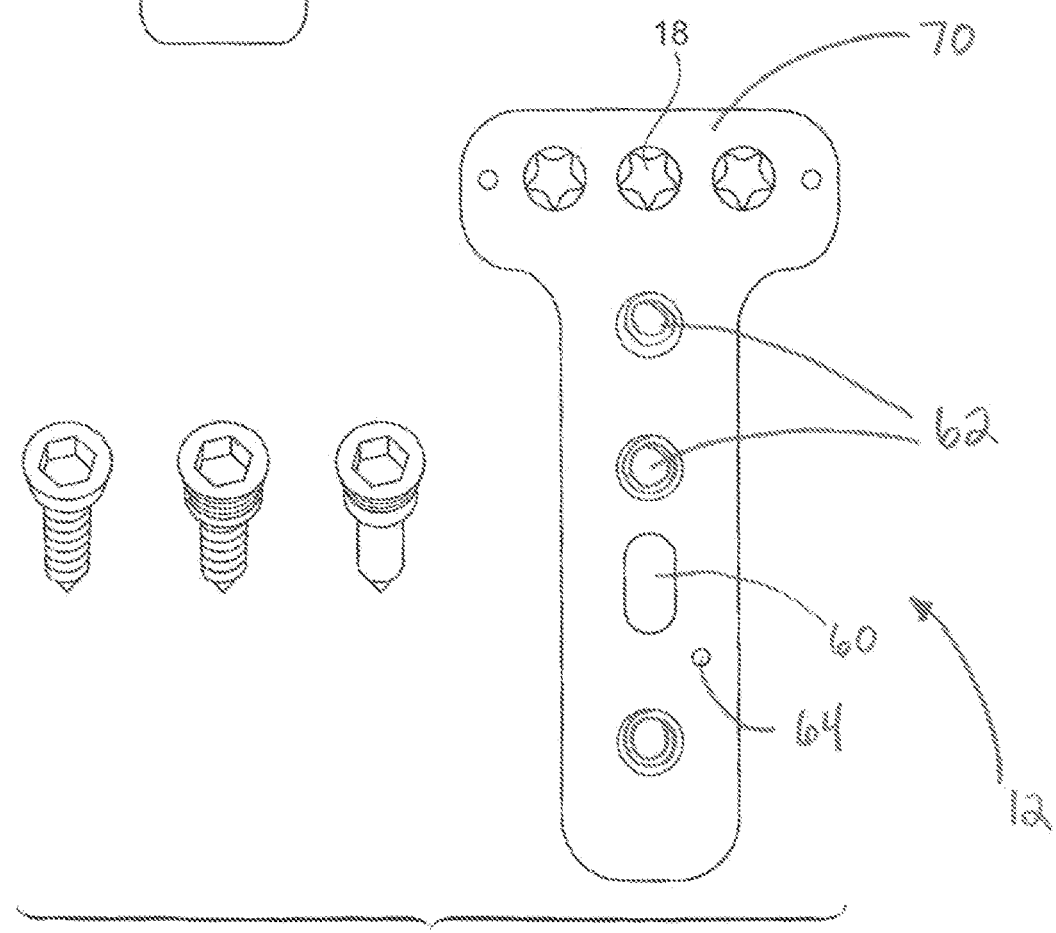
FIG. 11
FIG. 12

Partial articular (41-B)*

Partial articular (43-B)*

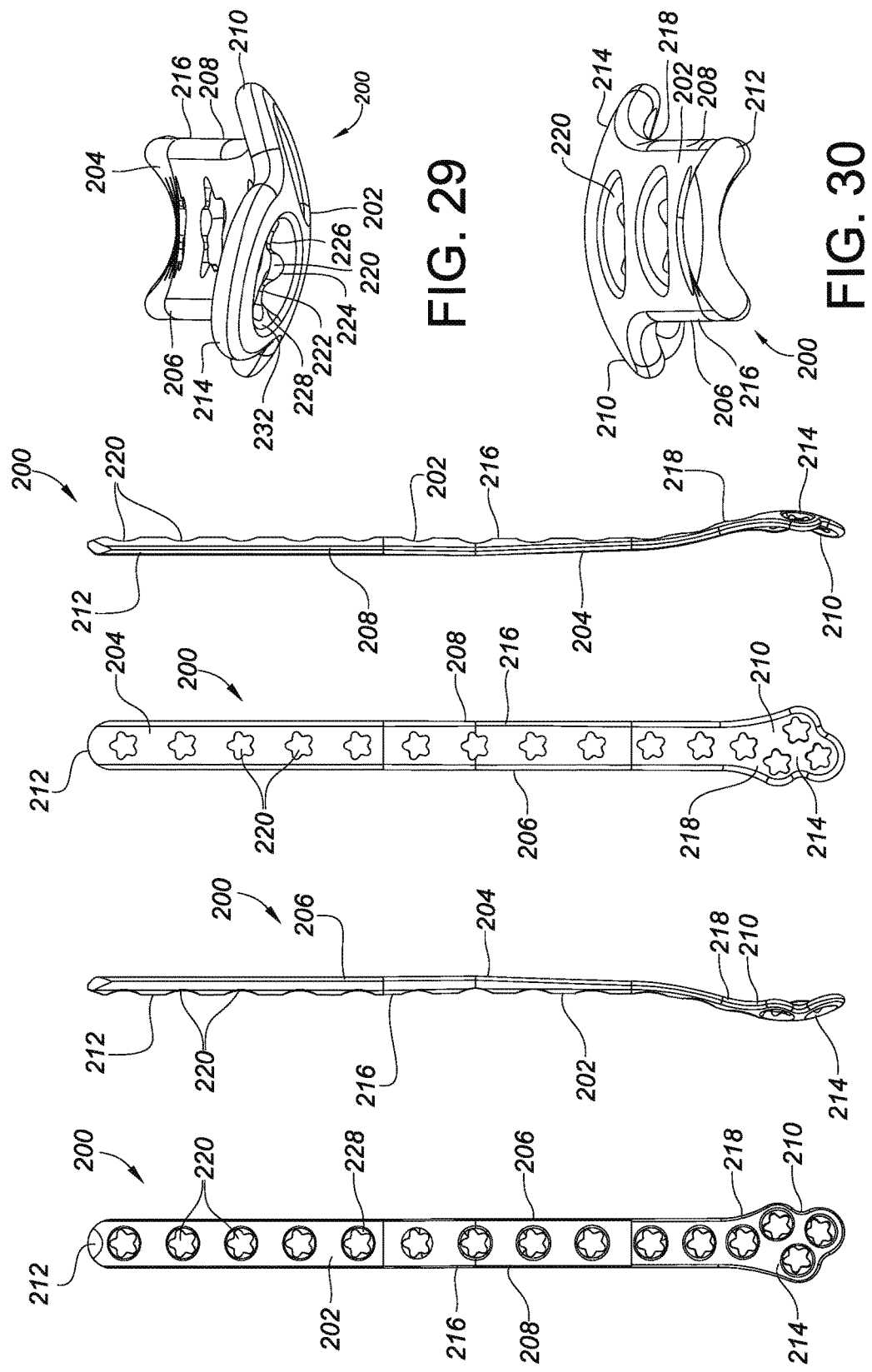

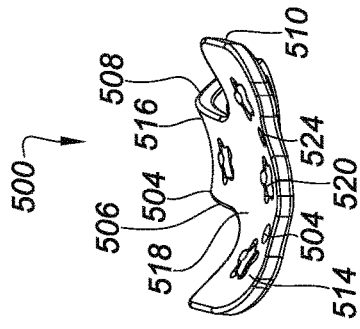
FIG. 54
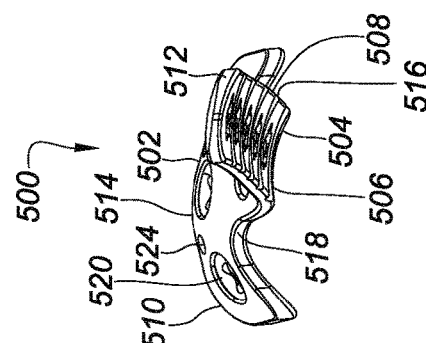
FIG. 55
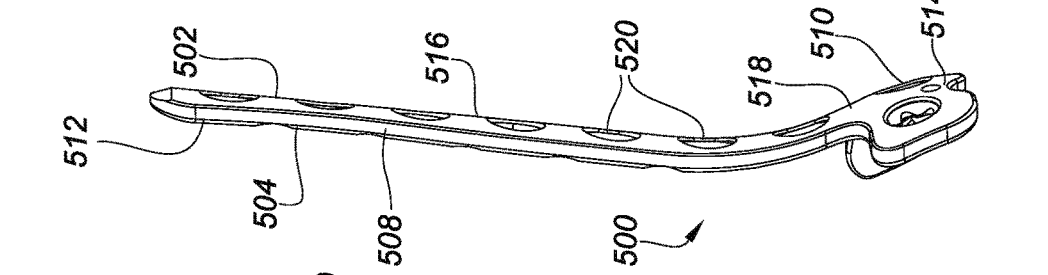
FIG. 53
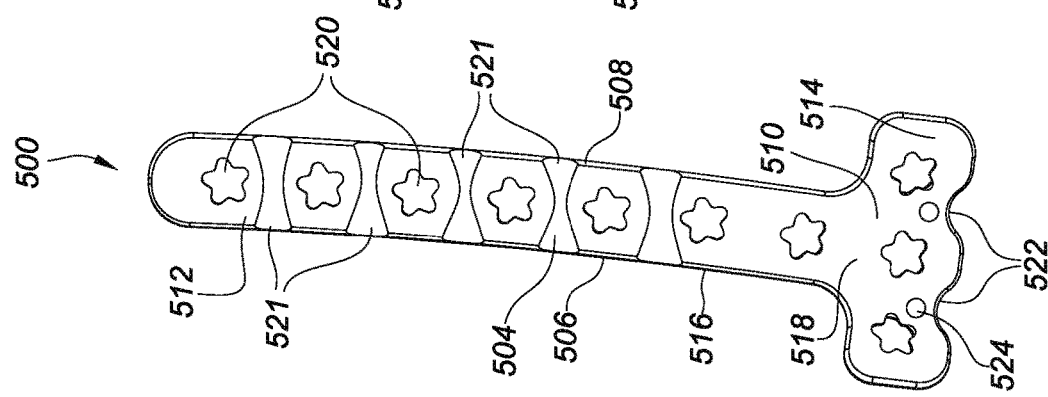
FIG. 51
FIG. 52
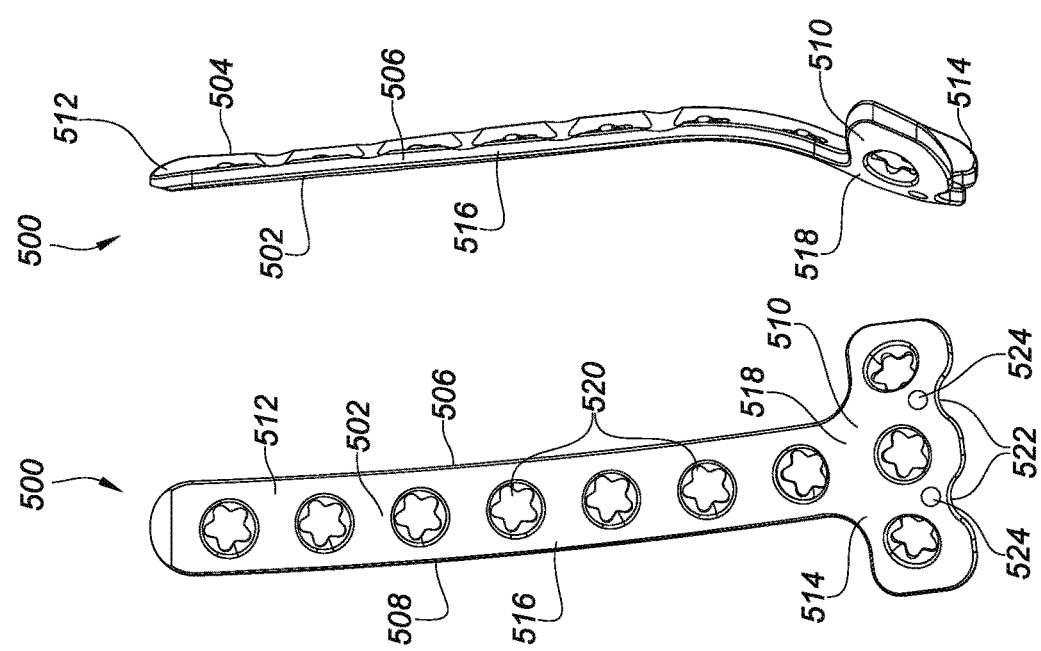
FIG. 50

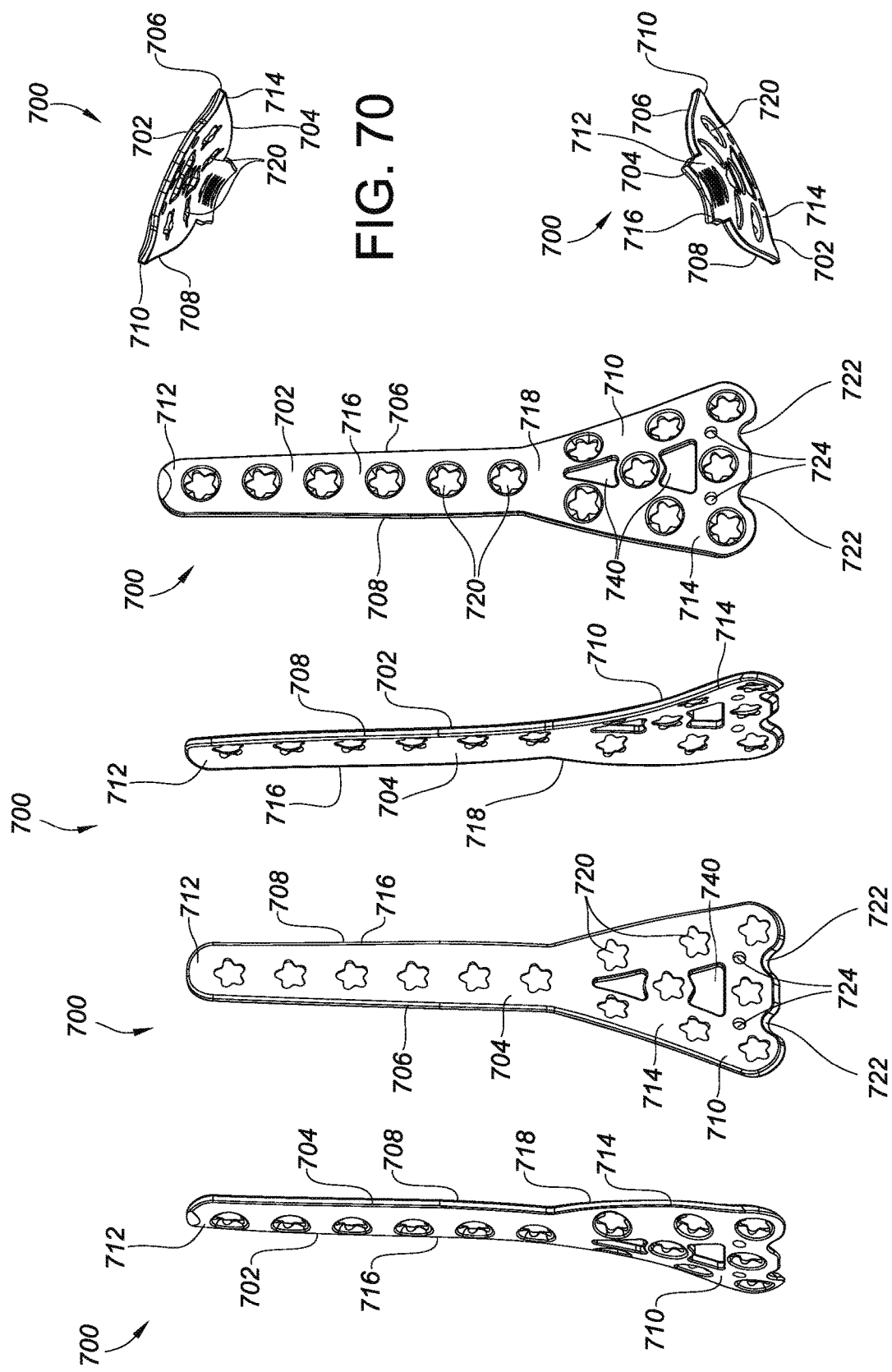

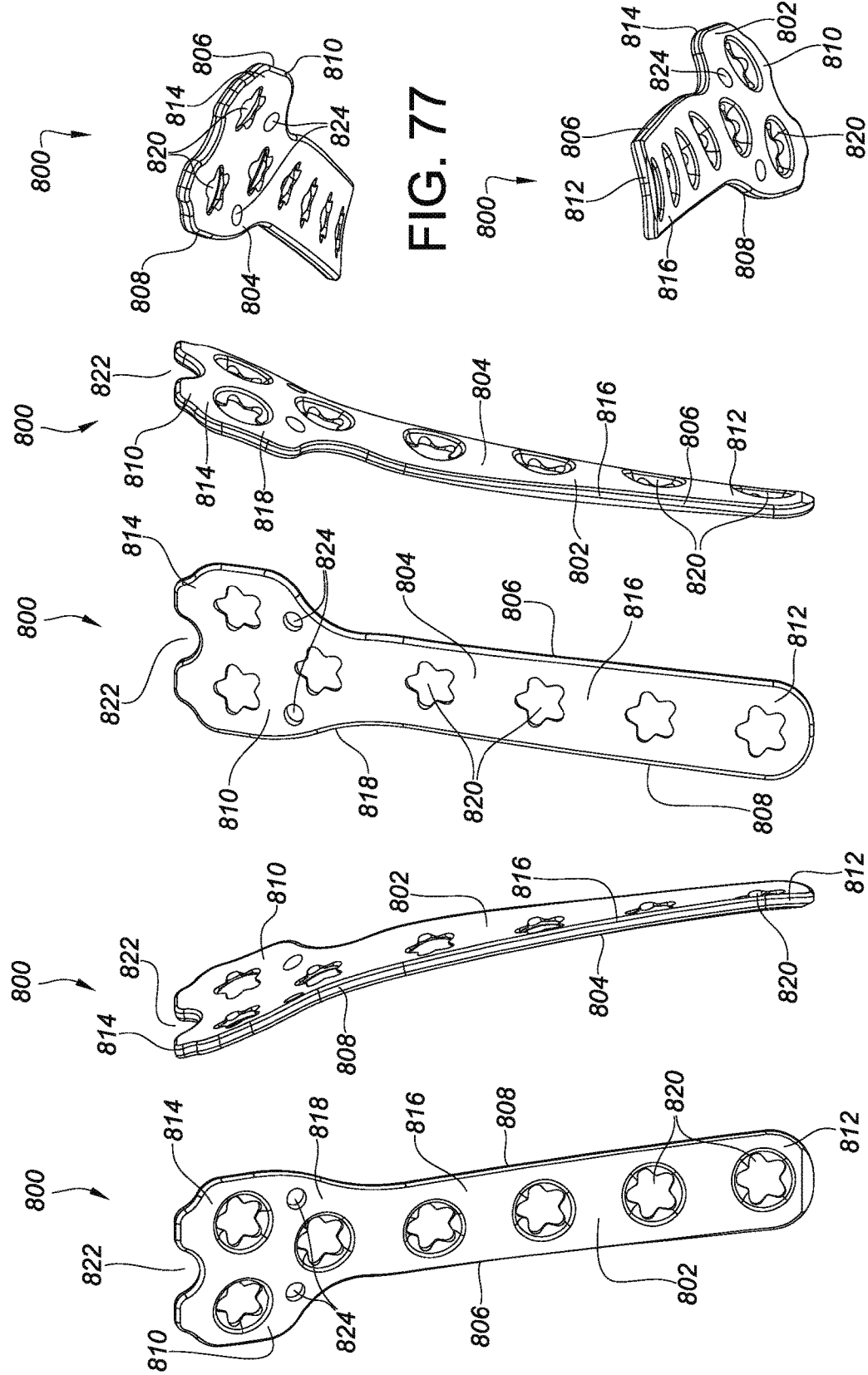

SYSTEMS AND METHODS FOR USING POLYAXIAL PLATES

CROSS-REFERENCE TO RELATED APPLICATIONS

This application is a continuation of U.S. patent application Ser. No. 15/970,779, filed May 3, 2018, which is a continuation of U.S. patent application Ser. No. 15/706,877, filed on Sep. 18, 2017, now U.S. Pat. No. 10,092,337, which is a continuation of U.S. patent application Ser. No. 14/535,573, filed on Nov. 7, 2014, now U.S. Pat. No. 9,795,424, which is a continuation of U.S. patent application Ser. No. 13/774,721, filed on Feb. 22, 2013, now U.S. Pat. No. 8,888,824, which is a continuation of U.S. patent application Ser. No. 12/069,331, filed on Feb. 8, 2008, now U.S. Pat. No. 8,382,807, which is a continuation-in-part of U.S. patent application Ser. No. 11/996,795, filed on Aug. 1, 2008, now U.S. Pat. No. 8,940,028, which is the U.S. National Phase of International Application No. PCT/US2006/028778 filed on Jul. 25, 2006, which claims the benefit of U.S. Provisional Application Ser. No. 60/702,231, filed on Jul. 25, 2005, titled "Locking Screw," the entire contents of the prior applications are hereby incorporated by reference in their entirety.

BACKGROUND

This invention relates generally to orthopedic fixation devices and bone plating systems for fracture fixation, and particularly to systems and methods for using bone plates that provide polyaxial fixation of fasteners.

Bone fractures are often repaired by securing a bone plate across the fracture. Depending upon which bone is to be treated, the bone plate may be straight or curved to match the contour of the bone for which it is designed. Bone plates may also be provided in many shapes and sizes. In cases where a bone is severely comminuted or if bone segments are missing, the use of bone plate and screw systems promotes healing of the fracture by providing a rigid fixation or support structure between the bone and the plate.

Bone plates may be secured to the bone in a number of ways. An existing solution is a plate and screw system where the screws are locked in the plate. A bone screw is threaded through an opening in the plate and into the bone. The screw is then secured to the bone plate via threads in the screw head that cooperate with threaded openings in the bone plate. This secures the plate with respect to the bone and provides rigid fixation because the relationship between the plate and screw(s) is fixed. Because the head of the locking screw interdigitates with threads in the plate, the plate and screws(s) form a stable system or construct, and the stability of the fracture can be dependent on or aided by the stiffness of the construct. Locking a screw into the plate can achieve angular and axial stability and eliminate the possibility for the screw to toggle, slide, or be dislodged, reducing the risk of postoperative loss of reduction.

However, although locking screws may reduce the incidence of loosening, they provide only one fixed angle relationship between the plate and the screw(s). The insertion angle is limited to a single direction because the threads of the head cooperate or mate with the threads of the hole in one direction only. The longitudinal axis of the screw lines up with the central axis of the hole, and no angular variation is allowed. In short, locking screws are unidirectional, limiting their use in some instances.

For example, when treating a severe fracture, fragments may be shattered and in irregular positions. Although a surgeon may wish to obtain the benefits of a locking screw and bone plate used together, the angle at which the locking screw extends from the plate at a certain opening may not be the angle that would allow the surgeon to "grab" (or seize, fix, or otherwise secure) the desired, random bone fragment. In this case, the surgeon may need to secure the plate to the bone somewhere else, or use a non-locking screw. Although non-locking screws do not lock into the plate, they can be inserted at various angles.

Specifically, non-locking screws are secured into bone in the same way that locking screws are, but they are not secured to the plate. Their heads are typically rounded where they contact the bone plate. Thus, one advantage of non-locking screws is that they can be inserted at various angles because they are not limited by the thread-to-thread contact of locking screws with the bone plate. However, if the surgeon desires the rigid stable construct of a locking screw and plate, the use of a non-locking screw to obtain the desired angular orientation is not necessarily optimal.

There have been bone plating systems developed that provide the surgeon with the option of choosing a non-locking or a locking screw. In some embodiments, these systems provide plates with some threaded holes (that may receive with either locking screws or non-locking screws) and some non-threaded holes (for non-locking screws). There are also systems that provide partially threaded slots to allow either non-locking or locking screws to be used together. Such combination slots provide surgeons with the intraoperative choice about whether to use the plate with locking screws, non-locking screws, or with a combination of both. These combination slots typically have a partially threaded opening that can receive either a compression screw or a locking screw. However, because these combination slots are only partially threaded, the locking screw(s) may not be able to maintain the fixed angular relationship between the screw(s) and plate under physiological loads. Specifically, the locking screws within the plate are only partially captured and thus only partially surrounded by threads. Under high stress and loading conditions, the slot may distort and allow the fixed angular relationship between the locking screw and plate to change. This can result in loss of fixation or loss of established intraoperative plate orientation. Moreover, the locking screw can still only be inserted at a single angle—the predetermined angle defined by the manufacturer.

Additionally, current bone plate and screw systems still limit a surgeon's ability to both (a) lock a fastener with respect to the bone plate, but still (b) allow the fastener to extend from the bone plate at various angles. Locking screws lock into the plate, but only in a single angular configuration, and non-locking screws allow various angle configurations, but they do not provide a stable construct with the plate. Accordingly, none of these options allow a surgeon to capture bone fragments that do not fall in line with the axis of the opening provided on the plate in a rigid fashion. An example of this problem is shown in FIG. 21. Thus, currently available options can still lead to malalignment and poor clinical results.

There have, however, been some attempts to provide polyaxial locking systems. For example, one effort includes providing holes that accept fixed angle locking pegs and multidirectional locking pegs, with a threaded cap inserted over the multidirectional peg to hold it into place. Such a system can be cumbersome to use because although the multidirectional peg can be inserted at any angle, the surgeon then needs to thread a small cap onto the top of the peg head and into the plate, requiring an extra step, extra time, and extra instrumentation. Such systems also fail to allow the use of non-locking members in conjunction with the locking and multidirectional pegs.

Other systems that have attempted to offer polyaxial fixation include providing a bone plate with inserts at the hole peripheries made out of a deformable material, with the remaining part of the plate made of titanium. The plate is manufactured and the inserts are then pushed into the hole peripheries and engaged in place by deformation and pressure. When screws are inserted, the inserts deform and are compressed between the edges of the holes of the plate, which holds the screws and inserts in place. Challenges with such systems are that they cannot be used with non-locking screws, the inserts do not have the strength to receive and hold a regular locking screw, (i.e., they do not provide the surgeon with options), and plates with deformable inserts are more expensive to manufacture than regular bone plates. Other attempts have failed to provide adequate locking mechanisms.

Another attempt at polyaxial fixation includes a plate with holes that have an internal jacket with recesses that extend away from the axis of the hole or into the internal jacket surface. This attempt is described in International Application WO 2005/018472, titled Bone Plate. The internal jacket surface of the plate described in that application is threaded or has ribs or protuberances. A bone screw is intended to be pulled into the hole of the plate by the internal jacket surface. If the bone screw head is threaded, when the screw in inclined, the threaded head is intended to "jump over" the pitches of the threads in the hole of the plate interrupted by the recesses, without "cutting through" them. The goal of the invention is to provide a bone plate that can have bone screws introduced at an angle that is different from the specified axis of the hole and secured into position.

It would be beneficial to provide plates and methods that combine polyaxial locking fixation with a thinner profile and enhanced bone contouring. Such plates could be useful in fixation of partial articular and/or non full body weight bearing fractures, where a more flexible plate that is more closely shaped in accordance with bone structure and that features polyaxial locking openings could provide additional options for the surgeon. Such features could, if desired, but not necessarily, provide plates that allow compression of a mid portion against bone to create a buttress effect while other portions of the plate are locked to the bone using polyaxial fixation. Such plates could also be used without buttressing effects, but in a more conventional reinforcement mode. Other features could be combined with any or all of these features.

SUMMARY

Certain embodiments of the invention provide plates for periarticular fractures or other non full body weight bearing applications that combine polyaxial fixation with a thinner profile and contouring that more closely conforms to bone. Such plates can be designed to achieve buttressing effect and/or to be used in a reinforcement mode. Other features can be combined with these. Such plates can be created for use on portions of the tibia, fibula, metatarsals, calcaneous, other ankle and foot bones, humerus, radius, ulna, spinal, maxillofacial, and other bones.

BRIEF DESCRIPTION OF THE DRAWINGS

FIGS. 11-15 show alternate shapes and types of bone plates that may be used with various embodiments of this invention.

FIG. 26 is a bottom view of the plate of FIG. 23.

FIG. 27 is a left-side elevational view of the plate of FIG. 23.

FIG. 28 is a right-side elevational view of the plate of FIG. 23.

FIG. 29 is a head-end view of the plate of FIG. 23.

FIG. 30 is a shaft end-view of the plate of FIG. 23.

FIG. 50 is a top view of the plate of FIG. 48.

FIG. 51 is a bottom view of the plate of FIG. 48.

FIG. 52 is a left-side elevational view of the plate of FIG. 48.

FIG. 53 is a right-side elevational view of the plate of FIG. 48.

FIG. 54 is a head-end view of the plate of FIG. 48.

FIG. 55 is a shaft-end view of the plate of FIG. 48.

FIG. 66 is a top view of the plate of FIG. 63.

FIG. 67 is a bottom-view of the plate of FIG. 63.

FIG. 68 is a right-side elevational view of the plate of FIG. 63.

FIG. 69 is a left-side elevational view of the plate of FIG. 63.

FIG. 70 is a head-end view of the plate of FIG. 63.

FIG. 71 is a shaft-end view of the plate of FIG. 63.

FIG. 73 is a top view of the plate of FIG. 72.

FIG. 74 is a bottom view of the plate of FIG. 72.

FIG. 75 is a right-side elevational view of the plate of FIG. 72.

FIG. 76 is a left-side elevational view of the plate of FIG. 72.

FIG. 77 is a head-end view of the plate of FIG. 72.

FIG. 78 is a shaft-end view of the plate of FIG. 72.

DETAILED DESCRIPTION

I. Plates with Polyaxial Openings Generally

Figure 1:
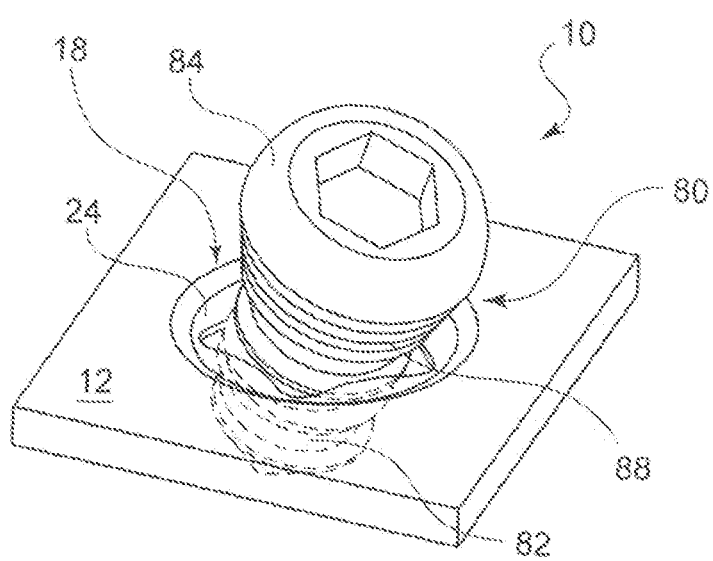
FIG. 1 shows a perspective view of a bone plate having fins according to one embodiment of the invention with a fastener inserted therein.

Embodiments of the present invention provide a bone fixation assembly that can accept and fix fasteners at a plurality of angles. A specific embodiment of a bone fixation assembly 10 is shown as a bone plate 12 and fastener 80 in FIG. 1. As shown in more detail in FIGS. 2-4, bone plate 12 has a lower surface 14 and an upper surface 16 and one or more openings 18 that extend from the lower surface 14 to the upper surface 16.

The embodiments described herein may be used in connection with any type of bone plate, non-limiting examples of which are shown in FIGS. 11-15. Plate 12 may be adapted to contact one or more of a femur, a distal tibia, a proximal tibia, a proximal humerus, a distal humerus, a clavicle, a fibula, an ulna, a radius, bones of the foot, or bones of the hand. The bone plate may be curved, contoured, straight, or flat. It may be a periarticular plate or a straight plate. An example of a straight plate in shown in FIG. 11. Plate may have a head portion that is contoured to match a particular bone surface, such as a metaphysis or diaphysis, flares out from the shaft portion, that forms an L-shape, T-shape, Y-shape, with the shaft portion, or that forms any other appropriate shape to fit the bone to be treated. An example of a T-shaped plate is shown in FIGS. 12-15, the openings on the plates in those figures are described in more detail below.

Bone plate 12 may be comprised of titanium, stainless steel, cobalt chrome, carbon composite, plastic or polymer—such as polyetheretherketone (PEEK), polyethylene, ultra high molecular weight polyethylene (UHMWPE), resorbable polylactic acid (PLA), polyglycolic acid (PGA), combinations or alloys of such materials or any other appropriate material that has sufficient strength to be secured to and hold bone, while also having sufficient biocompatibility to be implanted into a body. Although the above list of materials includes many typical materials out of which bone plates are made, it should be understood that bone plates comprised of any appropriate material are within the scope of this invention.

Figure 5:
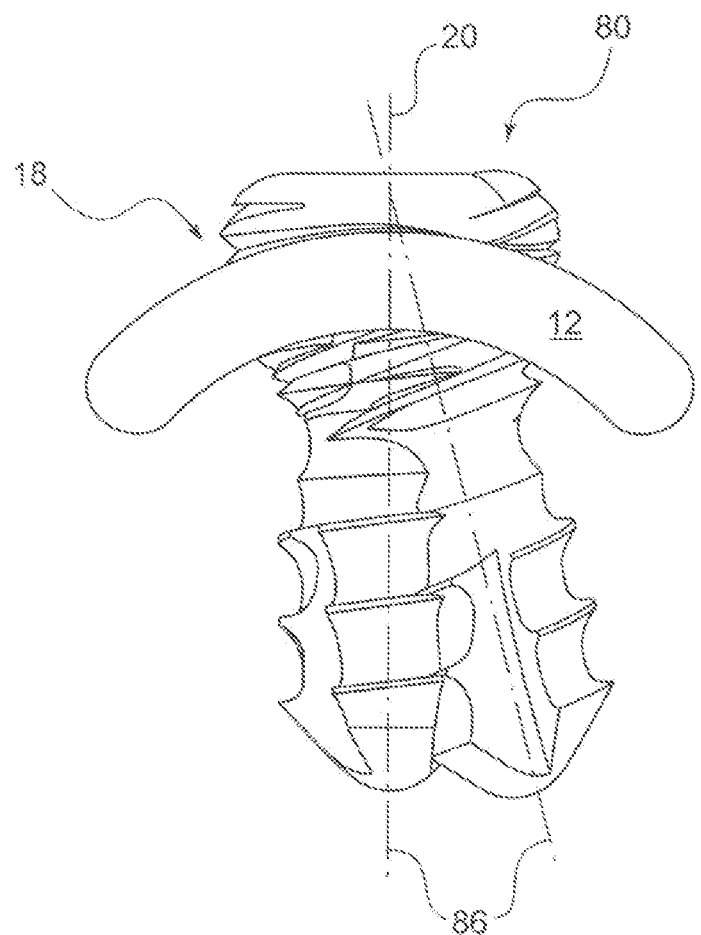
FIG. 5 shows a side perspective view of a bone plate with fasteners inserted therein to illustrate a few of the multiple angles at which the plate can receive a fastener.
Figure 6:
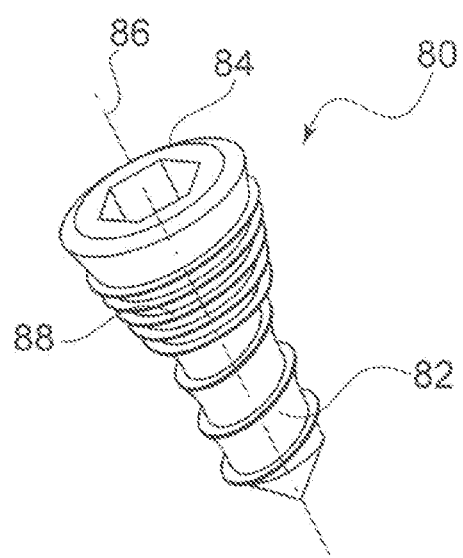
FIG. 6 shows an example of a fastener for use with various bone plates described herein.

Opening 18 of plate 12 is shown having a central axis 20, and it is adapted to receive a fastener. The fastener may be any typical, standard locking fastener or a non-locking fastener, although the embodiments described herein are intended for particular use with locking fasteners that have a series of threads on their heads. FIGS. 5-6 show examples of fastener 80 that may be used in accordance with embodiments of this invention. As shown specifically in FIG. 6, fastener 80 has a shaft 82 and a head 84. Shaft 82 may be threaded or otherwise configured to engage bone. It may be fully threaded, partially threaded, comprise a helical blade, and/or may comprise one or more tacks, deployable talons, expanding elements, or so forth. Any feature that allows shaft 82 to engage bone is considered within the scope of this invention and may be referred to generally as a "threaded shaft" for the sake of convenience. It is also possible, however, that shaft 82 is not threaded, so that fastener 80 takes the form of a peg or a pin. This alternative embodiment may be preferred in certain procedures where, for instance, the main goal is to prevent tilting of a bone segment, or in procedures where there is no concern of fastener 80 pulling out from the bone and hence no need for shaft 82 to be threaded or otherwise configured to engage bone. For the sake of reference, shaft 82 is also shown having a longitudinal axis 86. The end of shaft 82 may be a self-tapping or self-drilling tip, as shown in more detail in FIG. 5.

The head 84 of fastener 80 preferably has at least one set of threads 88. Threads 88 are typically any standard-type thread. For example, the threads 88 may be a continuous ridge or a non-continuous ridge. It may comprise a portion of a revolution, one complete revolution, multiple revolutions, a single lead, or multiple leads, or any other threads known in the art. Additionally or alternatively, head 84 of fastener 80 may include any other surface that will engage with and seat within specific features of plate (described further below). For example, head 84 may have a series of dimples, ridges, bumps, textured areas, or any other surface that can secure fastener 80 as described herein. As will be described in more detail below, threads 88 of head are adapted to engage, associate with, or otherwise cooperate with fins 24 of opening 18. In short, any type of threaded fastener head is intended for use with various embodiments of this invention.

Figure 2:
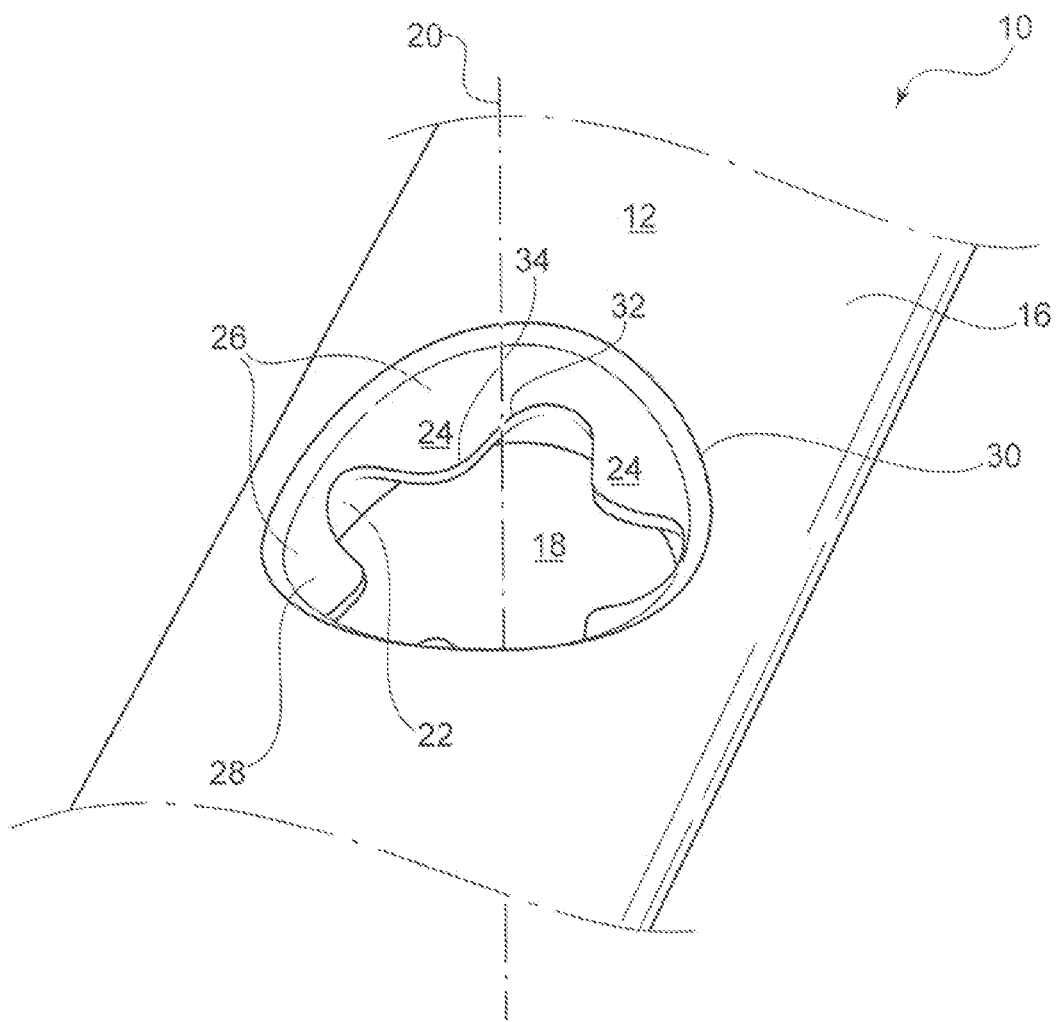
FIG. 2 shows a top perspective view of an opening in a bone plate according to one embodiment of the invention.
Figure 3:
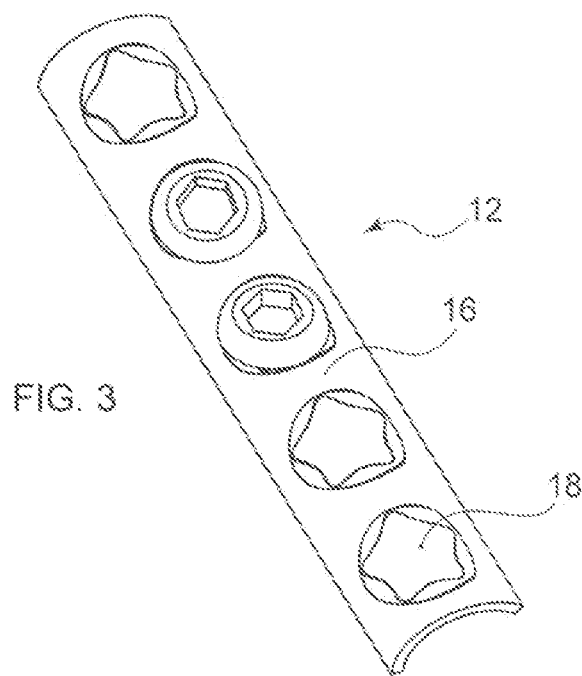
FIG. 3 shows a top view of a bone plate having multiple openings, with a fastener inserted therein.

Referring to FIG. 2, it can be seen that the embodiment shown has an opening 18 with an inner surface 22 that is defined by a series of concavely indented, inwardly protruding fins 24. Fins 24 extend into opening 18 toward central axis 20. The bases 26 of fins 24 form a concave portion 28 at or near a round circumference 30 of upper surface 16. (The term "round" circumference is intended to refer to any round shape, such as a circle, an oval, an egg-shaped circumference, or any other opening shaped to receive the head of a fastener 80.) The bases 26 of the fins 24 may all meet in substantially the same plane and then angle downwardly and inwardly at a similar angle or slope.

It bears noting that the concave portion 28 is smooth and non-threaded. In fact, there are not any threads on concave portion 28 or anywhere on inner surface 22 of opening 18. The lack of threads helps ease the manufacturing of plate 12, and allows plate be manufactured as thinly as desired.

For example, the thickness of plate 12 and the dimensions of fins 24 are typically dependent upon the pitch and threads of fastener 80. For example, a larger plate 12 for use with a larger fastener (e.g., for use on a femur bone) will likely be thicker and will have larger and thicker fins than a smaller plate (e.g., for use on a smaller bone). In specific embodiments, the fins 24 are particularly thin so that they can be moved up or down and deformed upon pressure. In some embodiments, the fins may be pressed toward the edges of the plate opening. A non-limiting exemplary range of thicknesses for fins may be from about 0.5 mm to about 5 mm, although larger and smaller sizes are possible. In theory, the fins 24 are intended to fit between crimps on the threadform of fastener 80, as shown in FIG. 1.

Providing a non-threaded inner surface 22 also allows the fastener 80 to be inserted into opening 18 at any desired angle, because there are not any threads to interfere with the desired angle, as illustrated by FIG. 5. The fins 24 are intended to slightly bend, deflect or deform in order to secure the fastener 80 in place in opening 18. Fins 24 actually engage threads 88 or other surface of fastener 10.

Figure 8:
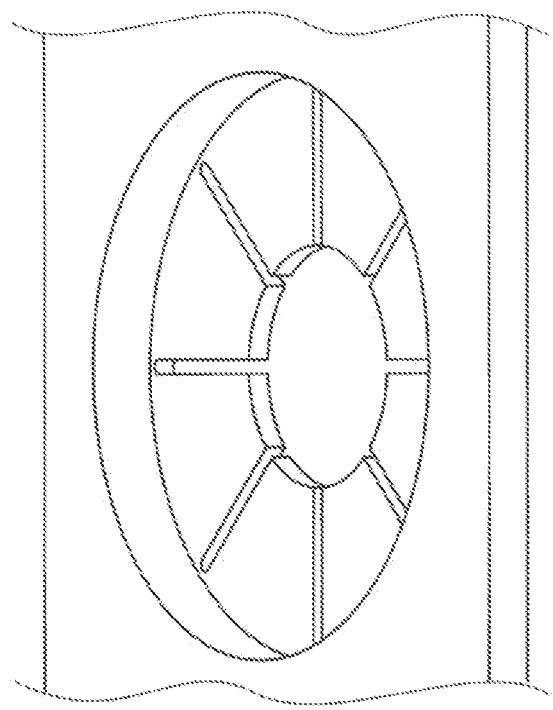
FIG. 8 shows a perspective view of the bone plate of FIG. 7.
Figure 7:
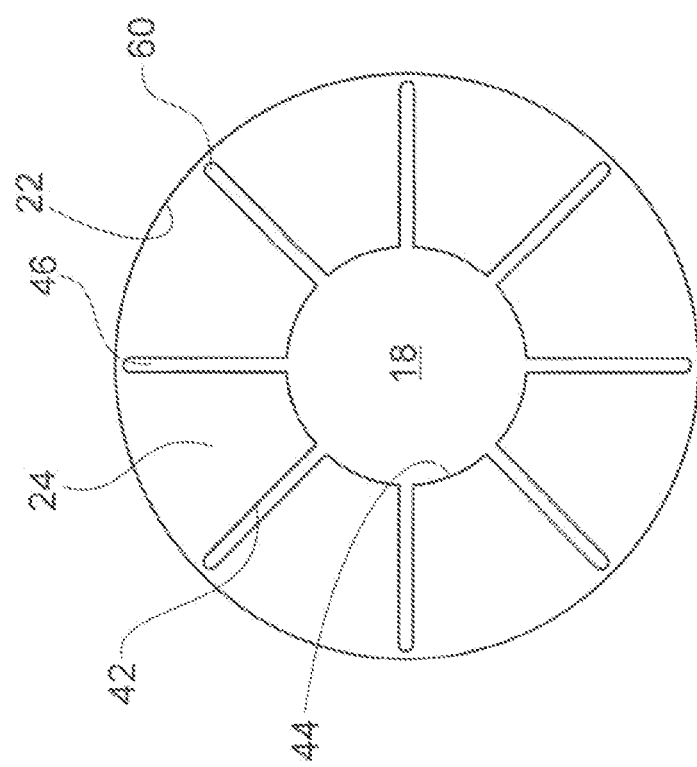
FIG. 7 shows a top plan view of an alternate embodiment of an opening in a bone plate.

Referring back to FIG. 2, in the embodiment shown, as fins 24 extend toward central axis 20, they taper to form tapered sides 32. The fins end at rounded tip 34, although tips 34 can be pointed, square, rectangular, or any other appropriate configuration. For example, as shown in FIGS. 7 and 8, fins 24 may have straight edges or sides 42 and straight ends 44. This embodiment shows fins 24 that are partially rectangular-shaped. The openings 46 between fins 24 are slit-shaped.

Figure 10:
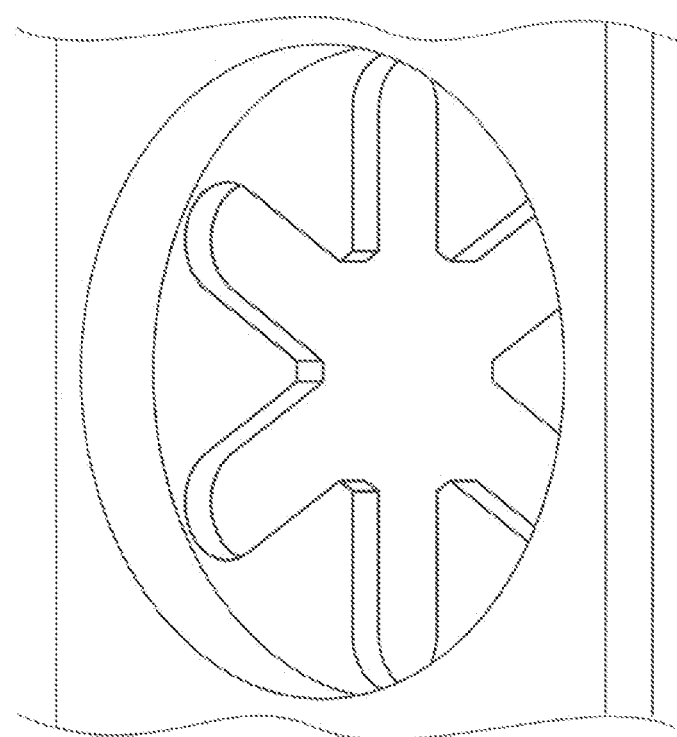
FIG. 10 shows a perspective view of the bone plate of FIG. 9.
Figure 9:
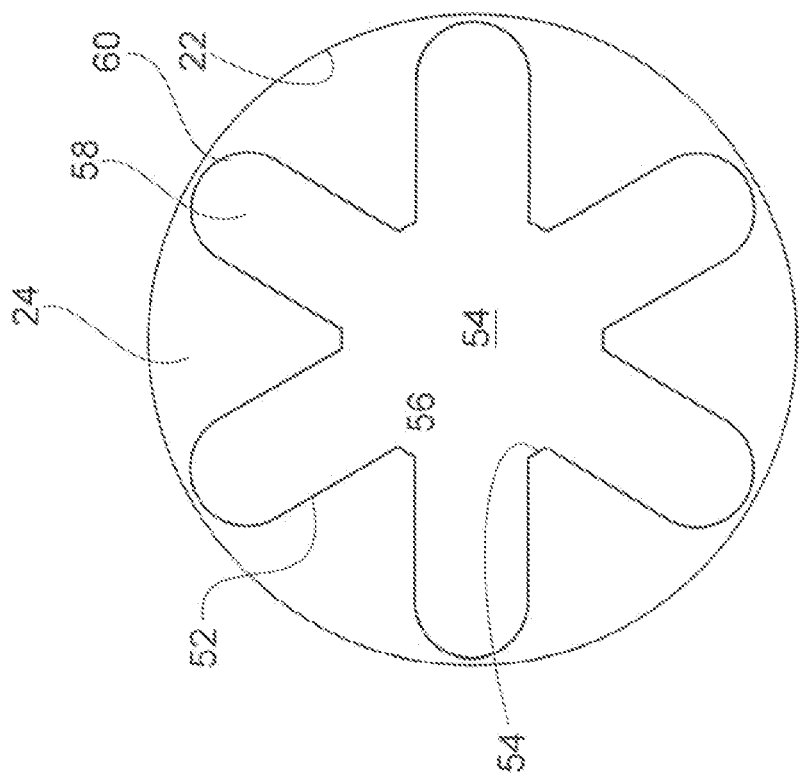
FIG. 9 shows a top plan view of a further embodiment of an opening in a bone plate.
Figure 15:
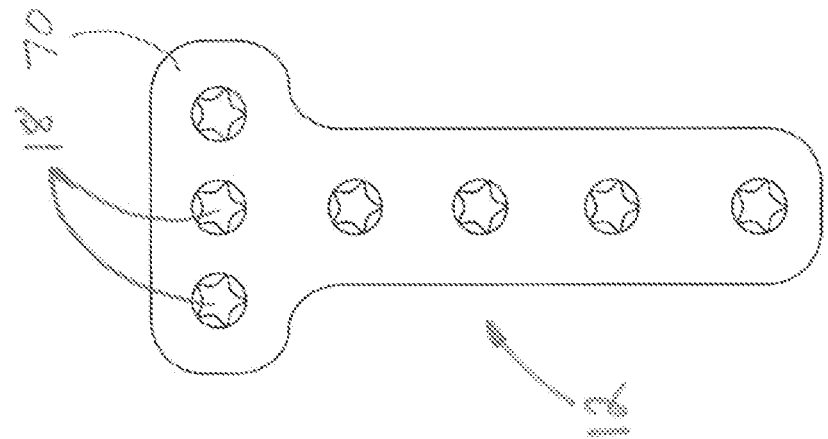
Figure 14:
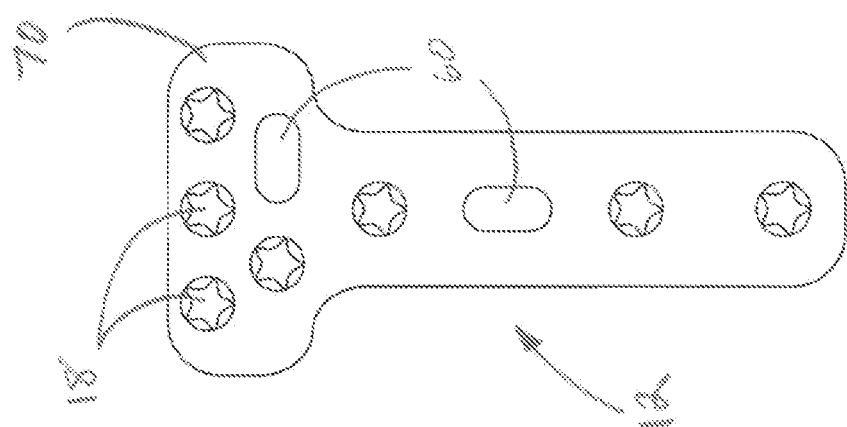
Figure 13:
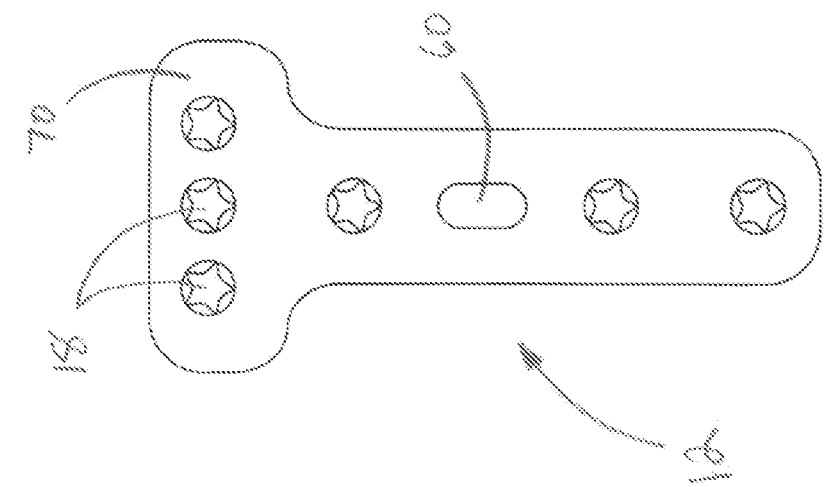

An alternate embodiment is shown in FIGS. 9 and 10, which illustrate fins 24 with a more triangular shape. In this embodiment, fins 24 are shown having sides 52 that taper inwardly and edges 54 that are flat and small, forming the apex area 56 where sides 52 come to an end. Openings 58 between fins 24 are more elongated than openings 46. Both sets of openings 46, 58 in these alternate embodiments are shown having rounded backs 60, where they meet inner surface 22 of opening 18. It should be understood however, that these are merely examples of fin 24 shapes and openings 46, 58 and that any appropriate shapes are possible and considered within the scope of this invention. Non-limiting examples include trapezoidal, square, round, circular, triangular (with a pointed tip instead of apex area 56), and any other possible option.

Figure 4:
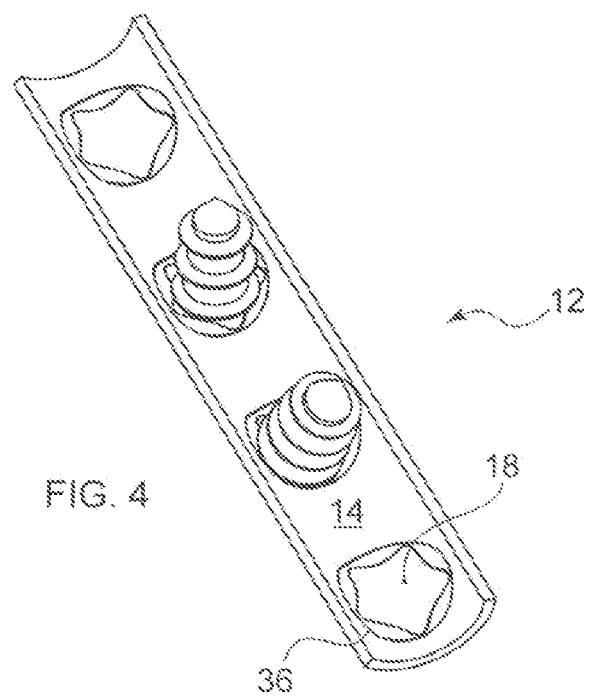
FIG. 4 shows an underneath view of the bone plate of FIG. 3.

As shown in FIG. 4, a second circumference 36 at the lower or underneath surface 14 of plate 12 may appear to be more jagged than the round circumference 30 at the upper surface 16 due to the fins 24 forming a portion of lower surface 14. The circumference can appear almost "flower-like"—each fin 24 appears to form a petal of the circumference. Alternatively, for the embodiments of FIGS. 7-10, the second circumference will appear similar to the shape created by fins 24.

Although the figures show an opening 18 with about five to eight fins 24, it should be understood that any number of fins 24 is considered within the scope of this invention. For example, there may be two or three fins, or ten or twenty or more fins 24, depending upon the plate for which the opening 18 is intended for use.

The primary purpose of fins 24 is to grasp one or more threads 88 of a threaded head fastener in order to secure the fastener in place in the bone plate 12, but a desired angle. For example, as opposed to threaded openings (which engage the threads of the head of the fastener in one way only, limiting the surgeon's ability to angle the fastener as desired), the fins 24 of this embodiment are still intended to secure the threads of the head of fastener in place, but at any angle. As the fastener is inserted, its threads start to engage the fins 24, as shown in FIG. 1. As discussed above, the fins 24 may be very thin so that as the head threads 88 start to grab fins 24, the fins 24 may move up or down as appropriate to engage the threads 88 and secure the fastener 80. In short, the threads 88 engage fins 24 (or fit in between fins 24). In most cases, this movement of fins 24 is a permanent deformation, so that the fins cannot flex back and allow the fastener to work its way out.

As discussed above, finned openings 18 may be provided on all types of bone plates, examples of which are shown in FIGS. 11-15. FIG. 11 shows a specific example of an opening 18 with fins 24 (referred to as a finned opening 18), a smooth opening 60, a threaded opening 62, and a provisional pin opening 64. Other options are holes that can be used with either a threaded or non-threaded fastener, as well as combination slots. It should be understood that these various types of openings may be used on any types of bone plates, in any combination and in any size, examples of which are shown in FIGS. 12-15. FIG. 12 shows a plurality of finned openings 18 in the head 70 of bone plate 12. This may help achieve better fixation of a fractured bone, because the fastener can be inserted at various angles to capture "renegade" or random bone fragments that have split from the bone during fracture, but still secure the bone fragments to the plate. For example, if a wrist bone is broken, there will be numerous fragments that may shatter in various directions. The plates 12 with finned openings 18 described herein can be used to place a fastener 80—at various angles in order to capture the renegade fragments that would otherwise not be secured to a bone plate using only a locking or a non-locking fastener. It should additionally be understood that other types of openings (in addition to or instead of finned openings 18) may be present in the head 70, as well as elsewhere on plate 12.

As previously mentioned, fastener 80 may be any typical fastener, made out of any appropriate material. It will typically have a bore for receiving a driver in order to secure fastener into bone and into plate 12. The receiving bore may be any size and shape, for example, it may have a hexagonal configuration to receive a corresponding hexagonal driver, a Phillips screw head, a flat-head, a star configuration, Torx, or any other appropriate configuration that can cooperate with a driver to place fastener.

Turning now to the methods of implantation, the surgeon accesses the surgical site of interest, which can be an internal site at which a bone fracture is located that requires stabilization to ensure proper healing. The fracture may be reduced with conventional forceps and guides (which are known to those in the art), and a bone plate of appropriate size and shape is placed over the fracture site. In some instances, the bone plate may be temporarily secured to the bone using provisional fixation pins. In the bone plates shown in FIGS. 11 and 12, provisional fixation pins may be used through either the provisional pin openings, or any other opening (threaded or non-threaded or finned) in the plate. Provisional fixation provides for temporarily securing the bone plate to the bone before placing fixation screws through the bone plate, so that one can be certain the bone plate is properly positioned before placing bone screws for permanent fixation of the bone plate to the bone. Moreover, with provisional fixation, x-rays can be taken of the bone plate/construct without excess instruments in the field of view.

Once the plate 12 is secured at a desired location in relation to the fracture (typically using one or more provisional fixation pins, although any other appropriate method may be used), the surgeon then identifies an insertion angle, or the direction along which fastener 80 is to be inserted through a selected opening 18 and driven into bone material. If bone plate 12 includes more than one opening, as shown in the figures, the surgeon also selects the specific opening to be used. After selecting the desired insertion angle and opening, the surgeon inserts shaft fastener 80 through opening 18 until the tip contacts bone material. In some cases, a hole may need to be drilled or tapped into the bone along the insertion angle to facilitate the initial tapping or insertion of fastener 80. The surgeon then uses an appropriate driving tool in the receiving bore of head 84 to manipulate the fastener 80 into place.

Because fastener 10 may be inserted at angles other than the aligned with the central axis 20 of the opening 18, as shown in FIG. 5, fastener 80 may be used to grab or secure bone fragments that are out of line with the traditional angle at which a locking screw would normally be inserted. The surgeon may need to toggle or maneuver the fastener 80 in order to secure and draw in displaced bone fragments.

Once the bone fragment is secured, the fastener 80 is ready to be secured to the plate 12. As fastener 80 is driven further into bone, it is also drawn further into plate 12. As threads 88 of fastener head 84 begin to contact fins 24, the fins are allowed to engage within the threads to hold the fastener 80 in place in the desired angle, even angles that are other than in line with the central axis 20. The action of engagement between fins 24 and threads 88 rigidly affixes fastener 80 to the bone plate 12 at the desired insertion angle. In some embodiments, the surgeon may then use traditional locking and/or non-locking screws in other openings on plate. This can help further secure the bone plate to the bone fracture if needed. One advantage of opening 18 is that it is adapted to receive any one of the potential fasteners that may be used with plate 12.

In some instances, once all fasteners and/or screws are placed, the surgeon may place covers over the unused openings, particularly if there are any unused openings that cross the fracture in order to strengthen the plate 12. Additionally or alternatively, the surgeon may use bone graft material, bone cement, bone void filler, and any other material to help heal the bone.

Figure 16:
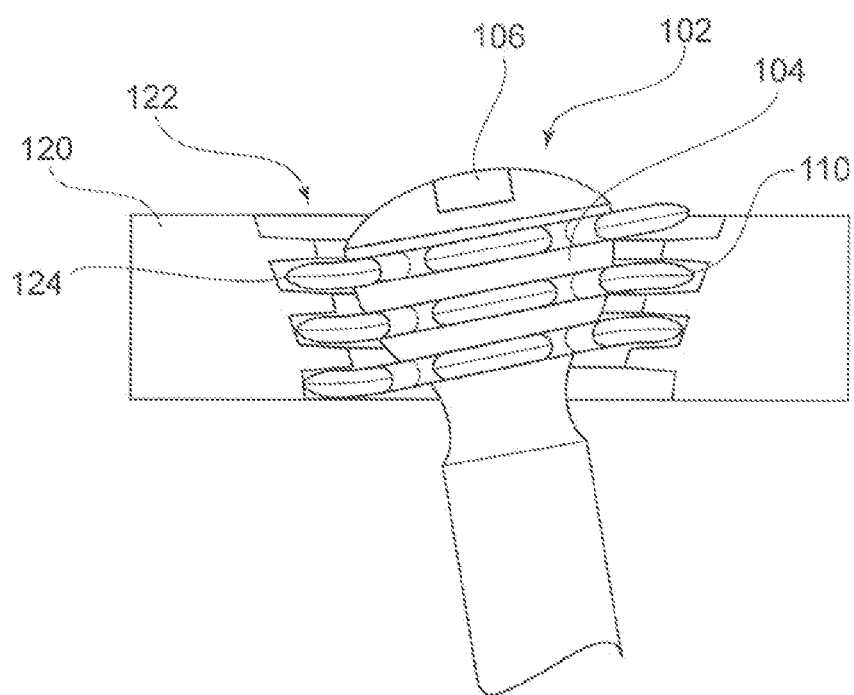
FIG. 16 shows a cross-section view of an alternate embodiment having a finned fastener in place in a bone plate.
Figure 17:
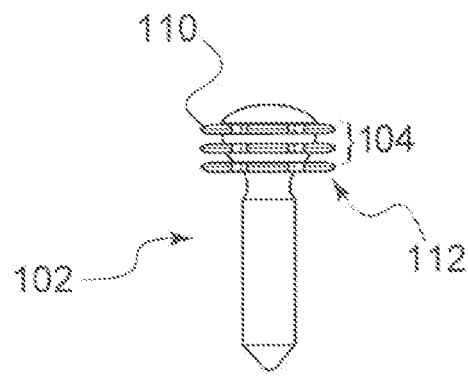
FIG. 17 shows a side perspective view of a fastener having a finned head according to one embodiment of the invention.
Figure 18:
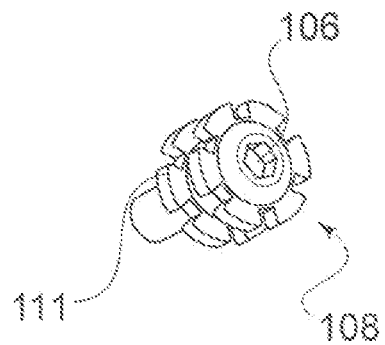
FIG. 18 shows a top perspective view of the fastener of FIG. 17.

An alternate embodiment of a fixation assembly is shown in FIGS. 16-18. These figures show a fastener 102 with a finned head 104. Specifically, the finned head 104 comprises a receiving bore 106 at its upper portion 108 and at least one set of extending fins 110 around the main portion 112 of the head 104. Fins 110 are shown as being square or trapezoidally-shaped with tapered edges, although they may be any other shape, such as rounded, oval, rectangular, curved, rhomboid, diamond-shaped, triangular or any other appropriate shape. The edges 111 of fins 110 may taper inwardly, outwardly, or be about parallel with one another. Fins 110 may be provided in a single row around head 104 or layered in multiple rows as shown. If layered in multiple rows, each individual fin 110 may be directly above another fin (so the top of the fastener 100 looks like that shown in FIG. 18). Alternatively, each individual fin 110 in a lower layer may be offset from a fin in a higher layer. The number of fins 24 in a set may also vary from about two or three up to any desired number that can fit on main portion 112 of head 104. As with the fins 24 of opening 18 described above, the fins 110 are preferably quite thin, the thickness varying depending upon the use of fastener and plate. For example, a larger fastener 102 for use with a larger plate (e.g., for use on a femur bone) will likely have larger and thicker fins 110 than a smaller fastener (e.g., for use on a smaller bone). In specific embodiments, the fins 110 are particularly thin so that they can be moved up or down or compressed upon pressure. A non-limiting exemplary range of thicknesses for fins may be from about 0.5 mm to about 5 mm, although larger and smaller sizes are possible. In theory, the fins 110 are intended to fit between the threadform of plate. Fastener may also have a shaft 114 that is threaded or unthreaded, as described above with respect to fastener 80.

Figure 19:
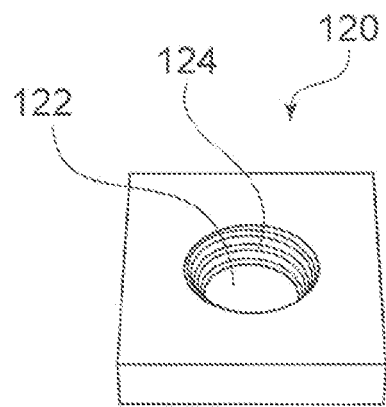
FIG. 19 shows a top perspective view of a bone plate that may be used to receive the fastener of FIGS. 17 and 18.
Figure 20:
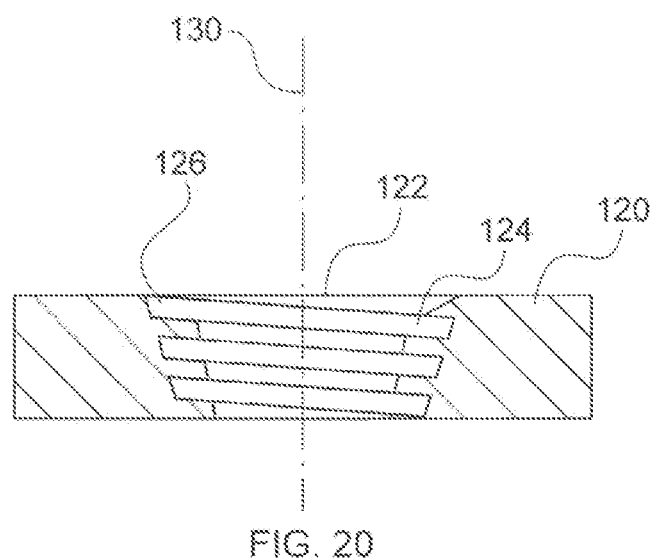
FIG. 20 shows a cross-section of the threads of the plate of FIG. 19.

Fastener 102 may be used with any bone plate that has a threaded opening. Any of the examples shown in the figures described above may be used with fastener 102. One option of a specific bone plate that can be used with fastener 110 is shown in FIG. 19. This bone plate 120 has Acme threads 124 that have a more rectangular shape than the pointed, sharp threads that are typically used in bone plates. As shown in FIG. 20, opening 122 has threads 124 that end at their edges 126 in a rectangular shape. Providing a rectangular shape with a flatter edge 126 allows a larger channel for the fins 110 to engage. In an even more specific embodiment, the threads 124 may be angled at about 15-20 degrees off of the central axis 130 of opening 122, and even more specifically, at about 18 degrees off of the central axis 130.

An example of the method of use is similar to that describe above. As fastener 102 is being inserted into bone plate 120 (although it should be understood that any traditional bone plate may used; Acme threads are not a requirement), the fins 110 are intended to engage threads of the plate and, much like the fins of the bone plate described above, fins 110 are very thin so that as the threads of plate 120 start to grab the fins 110, the fins 110 may move up or down as appropriate to engage the threads of plate and secure the fastener 102 in place, as shown in FIG. 16. In most cases, this movement of fins 110 is a permanent deformation, so that the fins cannot flex back and allow the fastener to work its way out.

II. Low Profile Plates

Generally

Figure 22A:
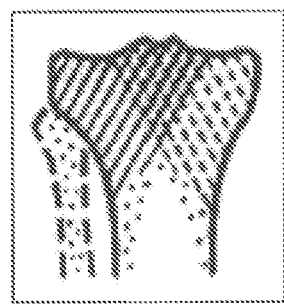
FIGS. 22a and 22b are schematic drawings which show types of fractures that can be treated with plates according to certain embodiments of the invention.
Figure 22B:
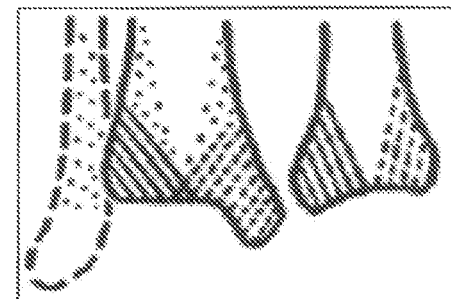
Figure 23:
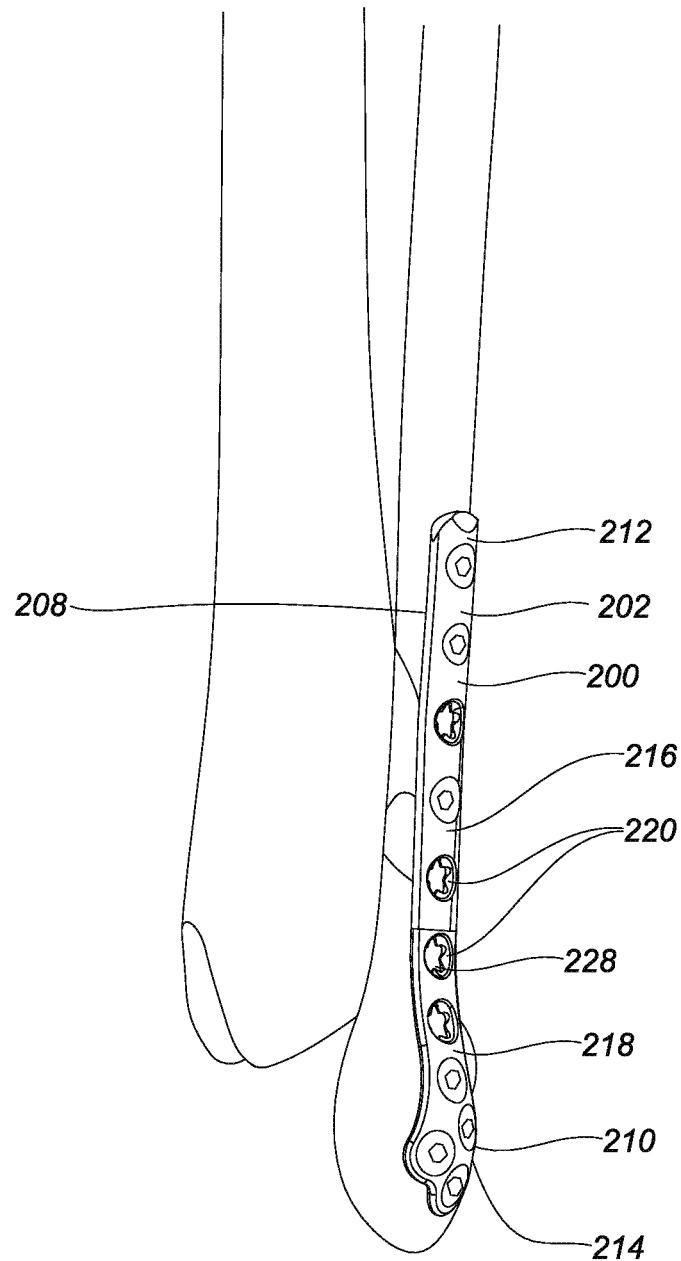
FIG. 23 is a posterior view of a portion of a tibia and fibula with an installed lateral distal fibula plate according to one embodiment of the invention.

FIGS. 23-89 show a number of low profile plates in accordance with certain embodiments of the invention. In general, such low profile plates can be used to treat partial articular fractures of the distal and proximal tibia such as those shown in FIGS. 22a and 22b and classified as AO/OTA Fracture classification type B. Such plates can also be used to treat such fractures in other bones, including, for example, portions of the metatarsals, calcaneous, other ankle and foot bones, humerus, radius, ulna, spinal, maxillofacial, and other bones. A tubular plate as shown in FIGS. 79-84 can be used to treat fractures, nonunions and osteotomies of the medial malleolus, fibula, distal ulna, olecranon, calcaneus, and metatarsals, among other bones.

Certain embodiments of such low profile plates are particularly useful in connection with periarticular fractures and fractures that do not bear full body weight. They are generally contraindicated for treatment of AO/OTA fracture classification types A and C, as well as fractures with extreme metaphyseal, comminution or dissociation of the articular segment from the bone shaft. Such low profile plates, subject to these limitations, can also be used in connection with osteopenic bone.

Generally, certain embodiments of such low profile plates can feature thicknesses of approximately 2 mm or less. Other thicknesses are possible. This thin or low profile acts together with the contouring of the plates, any desired edge treatment and screw-head shape to minimize wear of or effect on soft tissue surrounding the installed plates. The thin profile also acts in combination with the dimensions of the plate to provide a structure that is generally more flexible than conventional bone plates and thus particularly suitable for low profile, bone contouring, non-full body weight or physiological load bearing fixation in metaphyseal areas of bones such as, for example without limitation, tibia and fibula.

Figure 21A:
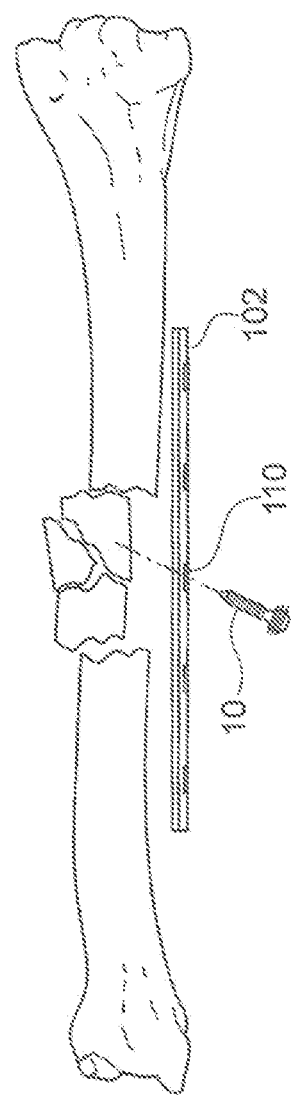
FIG. 21a shows an example of a fracture that may be treated with various embodiments of the invention.
Figure 21B:
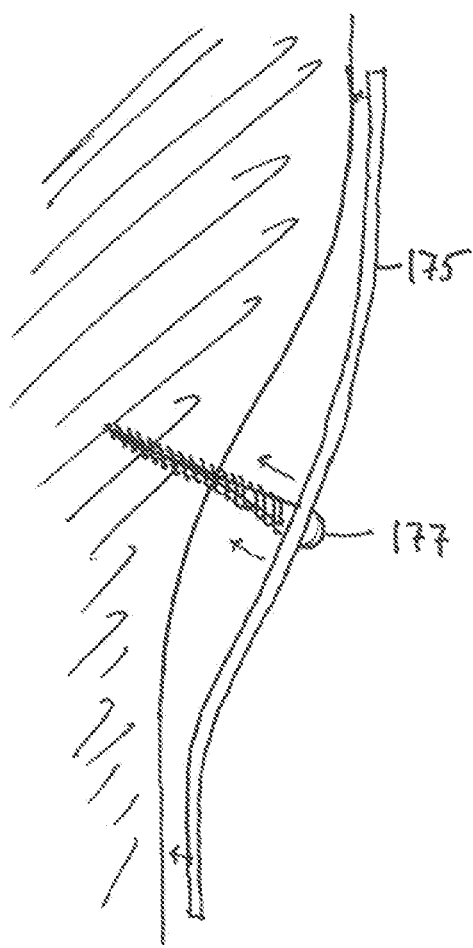
FIG. 21b is a schematic diagram that shows aspects of a buttressing effect achieved by certain plates according to certain embodiments of the invention.

These structural and material characteristics of some embodiments of such low profile plates can also provide plates which can be applied to achieve a buttress effect, whereby mid portions of the plate are compressed against bone using one or more cortex, compression or osteopenic screws and thereafter fixation is accomplished with polyaxial locking screws using polyaxial openings that can accept locking screws polyaxially. FIG. 21B schematically illustrates aspects of this buttressing effect. It shows a plate 175 that is not precisely shaped according to bone contour; rather, in one or more areas such as near the midportion of the plate 175, there is a gap between the plate 175 and the bone. When a compression screw 177 is inserted and torqued into the bone, the screw 177 pulls the plate 175 toward the bone or compresses the plate 175 on the bone. Flexibility or "springiness" of the plate 175, particularly in low profile plates according to certain embodiments of the invention, causes portions of the plate 175 located more toward the ends to bear against the bone or bone fragments in such a way that stabilization of the fracture is enhanced. The buttressing effect is assisted by insertion of locking screws into polyaxial openings of the plate to help create a more integral bone/plate construct for better stabilization, particularly in periarticular fractures. Certain low profile plates according to certain embodiments of the invention can be applied to bone in a reinforcement mode, rather than the buttress mode.

Low profile plates according to certain embodiments of the invention are particularly well suited to challenges presented by partial articular fractures. Factors such as intra-articular fracture extension, fracture pattern instability, and inadequate soft tissue coverage are addressed by plates according to certain embodiments of the invention that are preferably both versatile and comprehensive in their approach to fracture fixation. Traditional locked plating systems can enhance fracture stability through predetermined screw trajectories and precise plate position on bone. The enhanced stability can, however, reduce intraoperative versatility with respect to plate and screw placement. However, polyaxial locked low profile plates according to certain embodiments of the invention offer a greater degree of freedom relative to final implant position in connection with partial articular fractures and other fractures. According to certain embodiments, locking screws that feature heads with threads on their periphery, such as for example, conventional locking screws, can be inserted and retained in polyaxial openings in the plate up to 15 degrees in any direction and require no additional implants or procedural steps to ensure definitive locking. Low profile fixation in areas where implant prominence is a chief concern is accomplished by minimizing plate thickness near the joint without compromising needed implant strength, and minimizing screw head protrusion beyond the plate exterior surface in a way that would irritate surrounding tissue.

Accordingly, low profile plates according to certain embodiments of the invention take advantage of three features:
 (1) Polyaxial locking;
 (2) Low profile; and
 (3) Enhanced plate contouring.

According to certain embodiments, tabbed openings include a number of separate tabs, preferably but not necessarily five, that engage with threads of the locking screw head to form a fixed angle construct. Structure of tabs depends on a number of factors including thickness of plate, desired use of the plate, materials, types of screws contemplated for the plate, and other factors. Locking screws can be angled and locked up to 15 degrees in any direction, allowing for the creation of customized, multi-directional locked plating constructs. Preferably, each opening can accept 3.5 mm cortex, 3.5 mm locking and/or 5.0 mm osteopenia screws. Other types of screws may be used in connection with such openings, including other compression, cortex, locking, and/or osteopenia screws. Other types of polyaxial openings can also be used, as disclosed for example in Section I above. Preferably, openings are formed such that a locking screw can be withdrawn and reinserted a multiple number of times, including in different directions, without losing substantial angular retention of the screw by the plate.

The low profile feature ensures low profile fracture fixation in areas of minimal soft tissue coverage such as periarticular zones. Preferably, all screws also have a low head profile further to reduce potential for soft tissue irritation in these sensitive areas. Preferably, the thickness of such plates is approximately 2 mm or less.

Enhanced plate contouring not only minimizes prominence of the plate and therefore reduces potential for soft tissue irritation, but also facilitates fracture reduction and stabilization by allowing, if desired, mid portions of the plates to be compressed to bone to achieve buttressing effect. This effect helps, among other things, to resist torque and bending during fracture healing. Once securely fixed in place using such compression techniques, the plate produces a buttress effect to the fracture site to help prevent loss of reduction and enhance overall fracture fixation. Achieving buttressing effect is not necessary, however; the plates can also be installed in a reinforcement mode. Contouring also allows additional screw convergence in metaphyseal areas of bone.

Low profile plates according to certain embodiments of the invention are preferably made from ASTM F 139 Implantable Stainless Steel material or equivalent. Other suitable materials include titanium, titanium alloy, or any other bio compatible material which allows plates to perform satisfactorily with polyaxial locking, low profile and enhanced plate contouring features of embodiments of the invention. Indentations or undercuts, shown for example with numeral 521 in FIG. 51, can be formed in the interior surfaces of any such plates, including those for the tibia or fibula disclosed below, where desired to increase flexibility at certain locations; such indentations can be oriented perpendicular to the length of the plates or as otherwise desired.

Various types of openings can be used in low profile plates according to certain embodiments of the invention, including embodiments of plates disclosed below. Such openings can include, for example, tabbed openings as disclosed below, other polyaxial openings that are intended to receive and retain a locking screw at multiple angles, conventional threaded openings, conventional nonthreaded openings, slots, openings as disclosed in U.S. Pat. No. Re. 31628 reissued Jul. 10, 1984 to Allgower, et al., and/or openings as disclosed in U.S. Pat. No. 6,322,562 issued Nov. 27, 2001 to Wolter. U.S. Pat. No. Re. 31628 and U.S. Pat. No. 6,322,562 are herein incorporated by reference.

Following is a discussion of examples of certain low profile plates that incorporate these principles and that can be used in areas of the lower leg. Low profile plates according to embodiments of the invention can be used in other bones, as discussed above, but the following are nonlimiting examples.

Lateral Distal Fibula Plates

FIG. 23 is a posterior view of distal portions of a tibia and fibula with a lateral distal fibula locking plate according to one embodiment of the invention installed on the fibula. Generally, plate 200 also contains a head 214, a generally elongated shaft 216 and a transition portion 218 which generally connects the head 214 and shaft 216. Plate 200 includes an exterior surface 202, a bone contacting or partially bone contacting interior surface 204, a left edge 206, a right edge 208, a head end 210 and a shaft end 212. Exterior surface 202 may be generally convex, flat, or shaped as otherwise desired. Interior surface 204 may be generally concave, flat, or shaped as otherwise desired. Interior surface 204 can contain one or more indentations or undercuts which traverse across the interior surface 204 to modify flexibility of the plate, reduce bone contact, or other purposes.

Plate 200 is shaped to lie along the lateral aspect of the distal fibula and includes a cluster of tabbed openings 220 in the head through which screws can penetrate portions of the lateral malleolus. The transition portion 218 angles laterally, or toward the exterior surface 202, proceeding from shaft 216 to head 214. The head 214 is preferably cupped to conform to portions of the lateral malleolus. The shaft 216 is preferably shaped according to a traditional ⅓ tubular plate conventionally used to treat fibula fractures. Edges can be rounded and the shaft end 212 is preferably chamfered to facilitate percutaneous insertion.

Figure 25B:
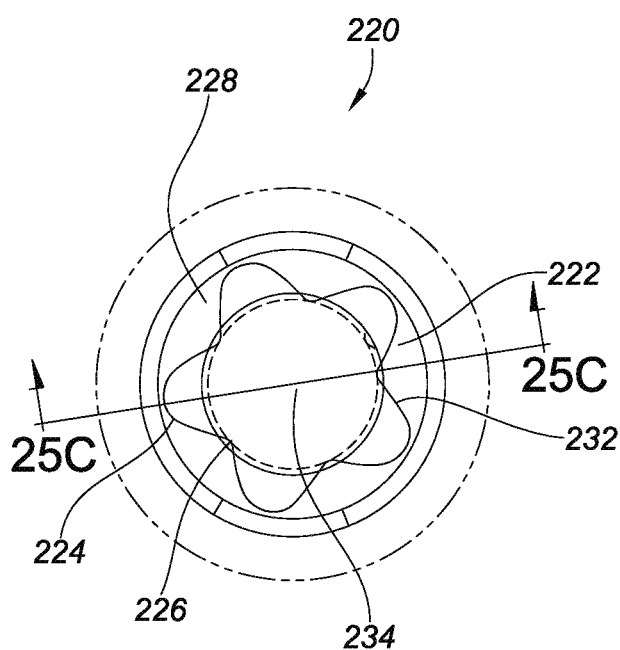
FIGS. 25b and c are a top plan view and a cross sectional view, respectively, of a tabbed opening according to one embodiment of the invention, as found for example in the plate of FIG. 23.
Figure 25C:
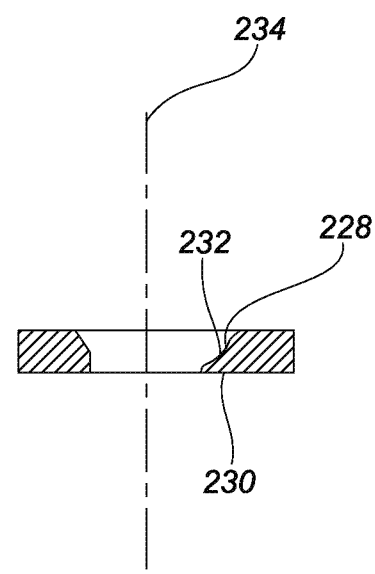
FIG. 25a is a top view of the plate of FIG. 23.

FIGS. 25b and 25c show detail relating to tabbed openings 220 that can be formed in plate 200. The plan view of FIG. 25b shows a tabbed opening 220 containing five tabs 222 and valleys 224. More or fewer tabs 222 can be used. Tabs 222 can but need not have an extremity 226 which can be but need not be of constant radius. Similarly, valleys 224 can if desired feature a constant radius. In cross section, as shown in FIG. 25c, the tabs 222 feature a concave or dished outer surface 228 and an inner surface 230 that can conform to the shape of the interior surface 204 of plate 200. Tab outer surfaces 228, as can be appreciated with reference to FIGS. 25b and 25c, together with portions of the opening 220 radially outward of valleys 224, form a dished compression screw receiving surface 232 that can be dished or otherwise formed to receive the head of a compression, cortex or osteopenic screws, or other suitable screw that can act to impart compression on a bone plate as it is rotated into the bone. Preferably as shown in FIG. 25c, but not necessarily, receiving surface 232 features a constant cross sectional radius. The particular structure shown in FIG. 25c allows opening 220 to receive and retain or lock relative to the plate in angularity 3.5 mm locking screws at orientations or angles up to 15 degrees in any direction from axial. That structure also allows openings 220 to receive 3.5 mm cortex and/or 5.0 mm osteopenia screws for compressing mid portions of plates according to embodiments of the invention against bone for buttress effect.

Preferably, the axis 234 of opening 220 is normal to a tangent formed at the center of the opening to the interior surface 204 of plate 200. Axis 234 could also be oriented normal to a tangent at the center of opening 220 to exterior surface 202 of the plate. Axis 234 could also be normal to or angulated with respect to either exterior surface 202 or interior surface 204 or any other desired structure on plate 200.

Preferably, tab inner surfaces 230 are flush with the interior bone contacting surface 204 of plate 200. Tab inner surfaces 230 do not need to be flush in that manner, however; they could be planar and/or recessed from interior bone contacting surface 204 if desired.

In operation, tab extremities 226 engage or cooperate with threads in locking screws, such as for example by interdigitating with the threads, or inserting themselves between the threads and deflecting, to allow a locking screw to be inserted at a desired angle, and the tabs 222 then to retain the screw at that angle or in that orientation or substantially that orientation relative to the plate 200.

Other types of polyaxial openings 220, such those disclosed for example in Section I above, can also be used for plate 200 in accordance with embodiments of the invention. Additionally, plate 200 can contain other types of threaded or nonthreaded openings and/or slots as discussed above in this document.

Figure 24A:
FIGS. 24a and 24b are radiographs showing an installed plate according to FIG. 23 and the bone in which it is installed.
Figure 24B:
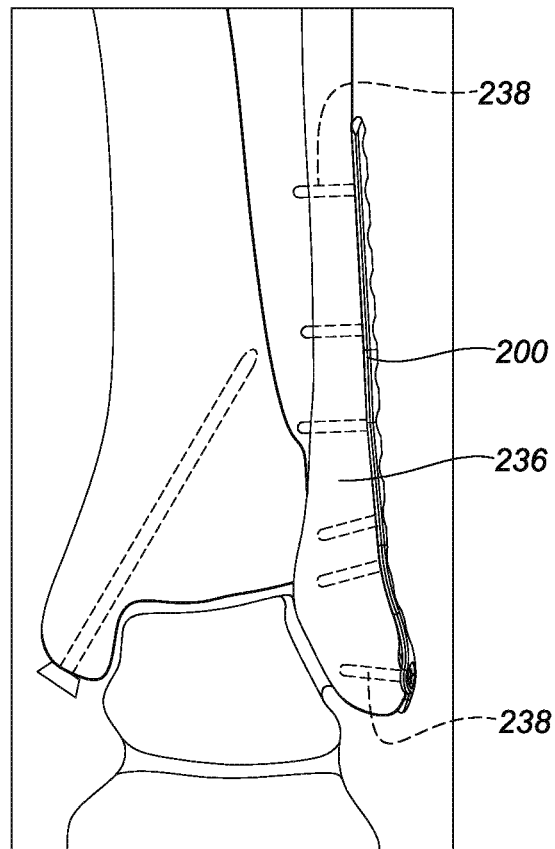

FIG. 24b shows a lateral distal fibula plate 200 with a cortex or compression screw 236 inserted to compress mid portions of plate 200 against the fibula to achieve buttressing effect. Two locking screws 238 fix the plate 200 to the fibula proximal to the cortex screw 236 and three locking screws 238 fix portions of plate 200 distal to cortex screw 236 to portions of the lateral malleolus or distal portions of the fibula. FIGS. 25a and 26-30 show various views of plate 200.

The particular plate 200 shown in FIG. 23 features a thickness of 0.067 inches plus or minus 0.005 inches (1.7 mm plus or minus 0.127 mm), but other thicknesses could be used, preferably approximately 2 mm or less. Plate 200 is preferably machined from ASTM F 139 Implantable Stainless Steel material, but other materials as discussed above could be used. Plate 200 is preferably machined from the material, but could be punched, forged, cast, made according to any combination, or as otherwise desired.

Posterolateral Distal Fibula Plates

FIGS. 31-38 show a posterolateral distal fibula plate according to one embodiment of the invention. Plate 300 includes an exterior surface 302, a bone contacting or partially bone contacting interior surface 304, a left edge 306, a right edge 308, a head end 310 and a shaft end 312. Exterior surface 302 may be generally convex, flat, or shaped as otherwise desired. Interior surface 304 may be generally concave, flat, or shaped as otherwise desired. Interior surface 304 can contain one or more indentations or undercuts which traverse across the interior surface 304 to modify flexibility of the plate, reduce bone contact, or other purposes.

Preferably more toward the head end 310 than the shaft end 312, a number of scallops 314 can be formed in the lateral facing edge of plate 300 as installed. A rounded corner 311 can be formed at the right edge 308/head end 310 intersection, and elsewhere as desired. Scallops 314 provide space in which a syndesmotic screw 316 can be inserted without undue interference by plate 300. Scallops 314 can be any desired shape. Plate 300 is otherwise generally in the shape of a ⅓ tubular conventional fibular plate, with a twist added to the head-end portion 310. The twist is preferably but not necessarily 8 degrees in an axial direction (counterclockwise proceeding toward head end 310 in the plate 300 shown in the drawings). The twist is provided to help avoid the peroneal nerve when the plate 300 is applied to the fibula.

Figure 31:
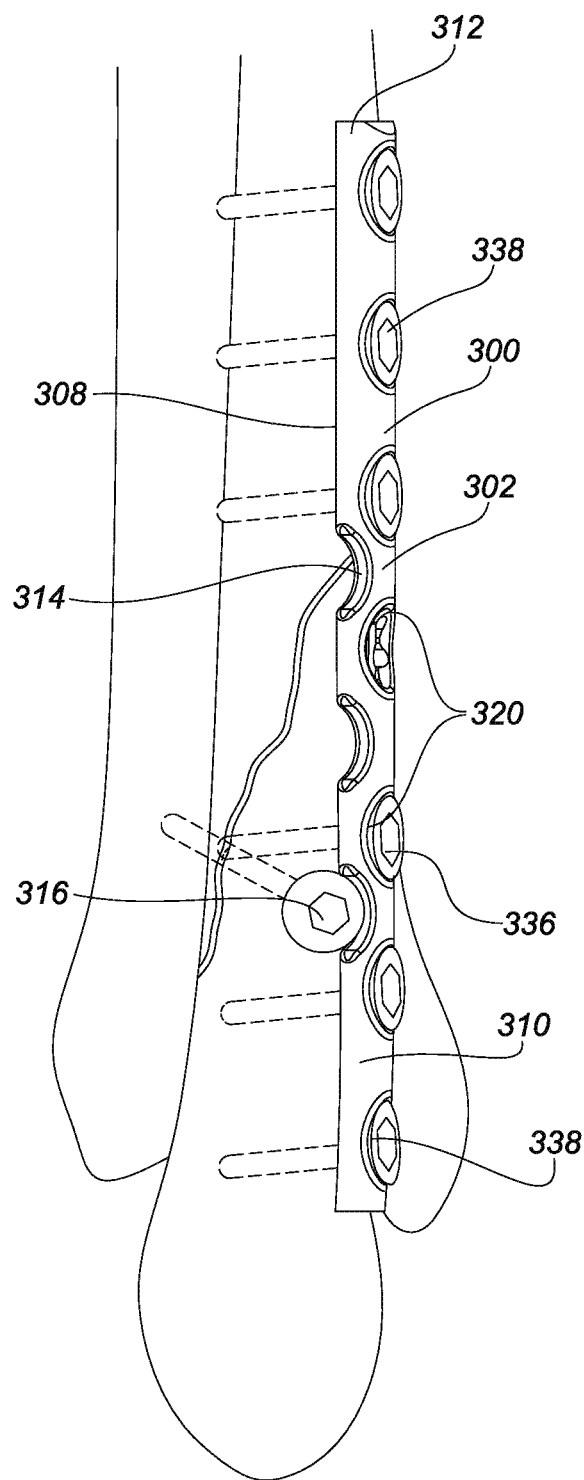
FIG. 31 is a lateral view of portions of a tibia and fibula with an installed posterolateral distal fibula plate according to an embodiment of the invention.

FIG. 31 shows a compression screw 336 inserted in the third opening 320 from distal. Two locking screws 338 are inserted on the distal side of the fracture and syndesmotic screw 316. A compression screw 336 is inserted at the proximal end of the plate 300 and two locking screws 338 are inserted in the next two openings 320.

Plate 300 preferably features polyaxial openings 320 as disclosed in connection with openings 220 of plate 200, and a thickness as disclosed in connection with plate 200. It is preferably formed of the material and by the techniques disclosed in connection with plate 200. Additionally, plate 300 can contain other types of threaded or nonthreaded openings and/or slots as discussed above in this document.

Figure 32A:
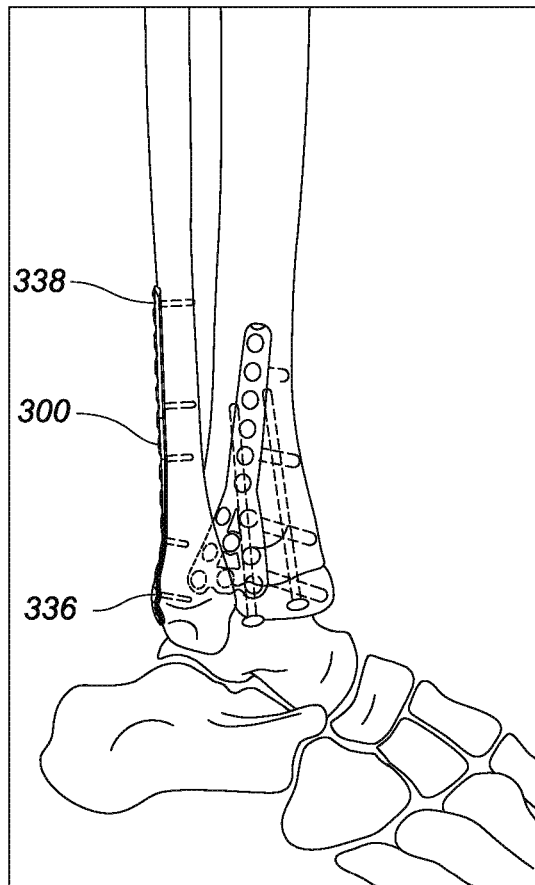
FIGS. 32a and 32b are radiographs of an installed plate of FIG. 31 and the bone in which it is installed.
Figure 32B:
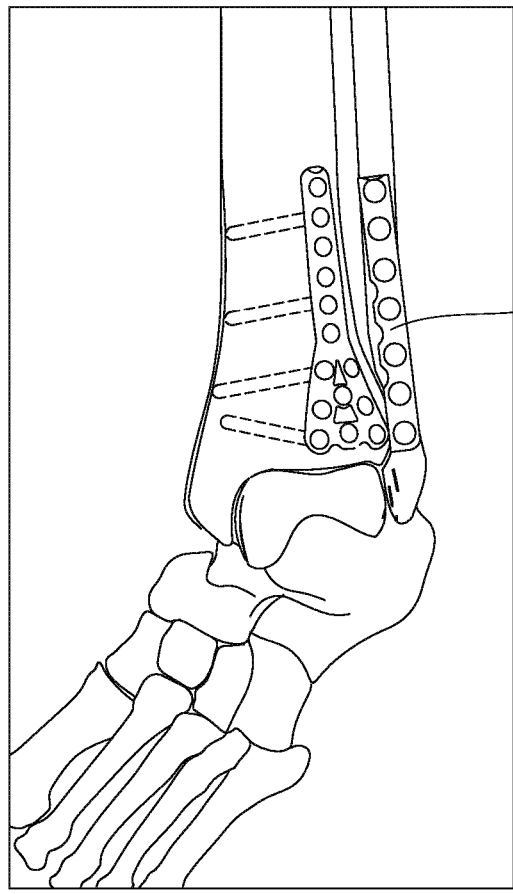
Figure 33:
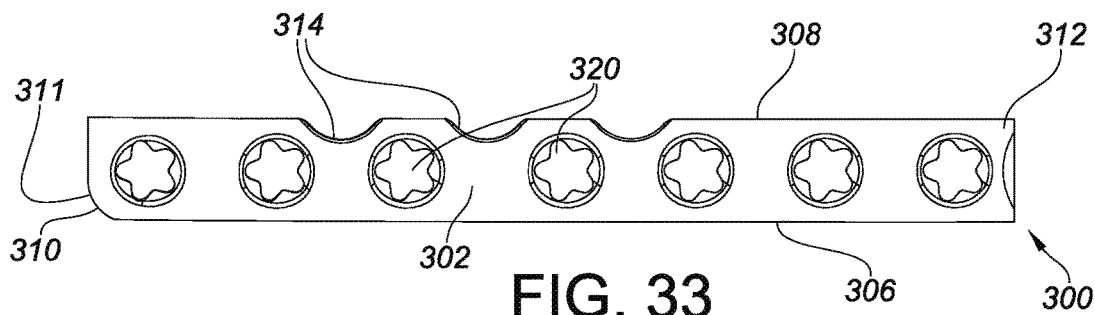
FIG. 33 is a top view of the plate of FIG. 31.
Figure 35:
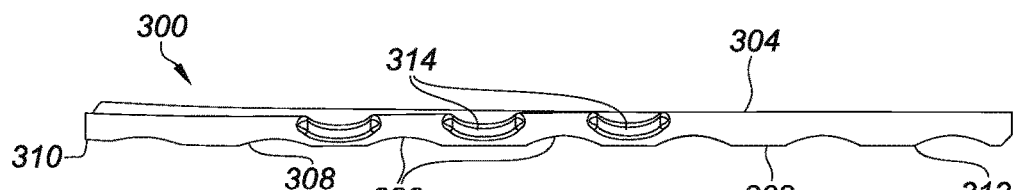
FIG. 35 is a right-side elevational view of the plate of FIG. 31.
Figure 34:
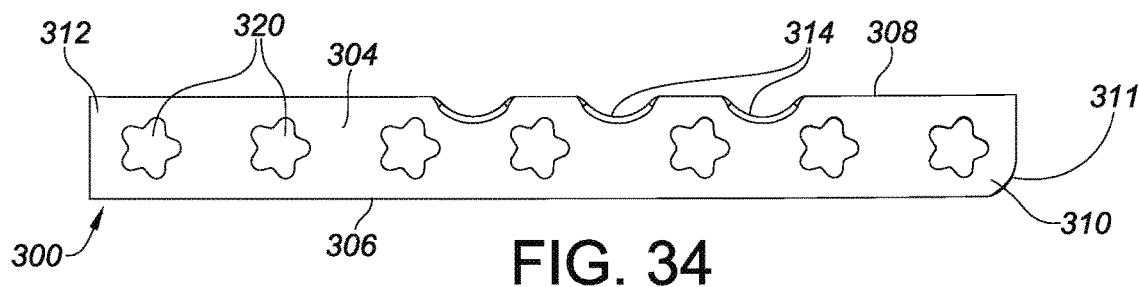
FIG. 34 is a bottom view of the plate of FIG. 31.
Figure 36:
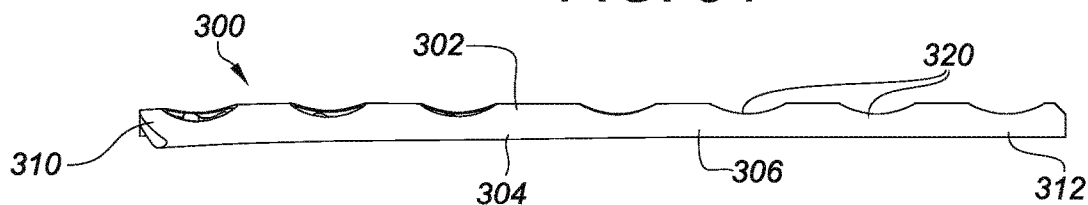
FIG. 36 is a left-side elevational view of the plate of FIG. 31.
Figure 37:
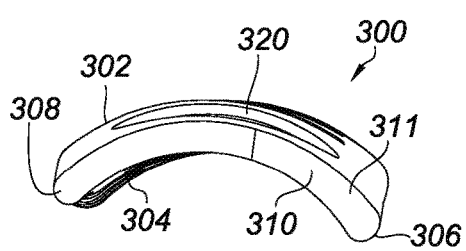
FIG. 37 is a head-end view of the plate of FIG. 31.
Figure 38:
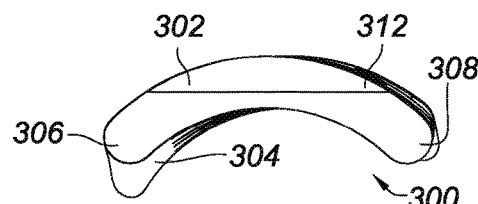
FIG. 38 is a shaft-end view of the plate of FIG. 31.

FIG. 32b is a radiograph showing plate 300 applied to bone.

FIGS. 33-38 show various views of the plate 300.

Lateral Proximal Tibia Plates

Figure 39:
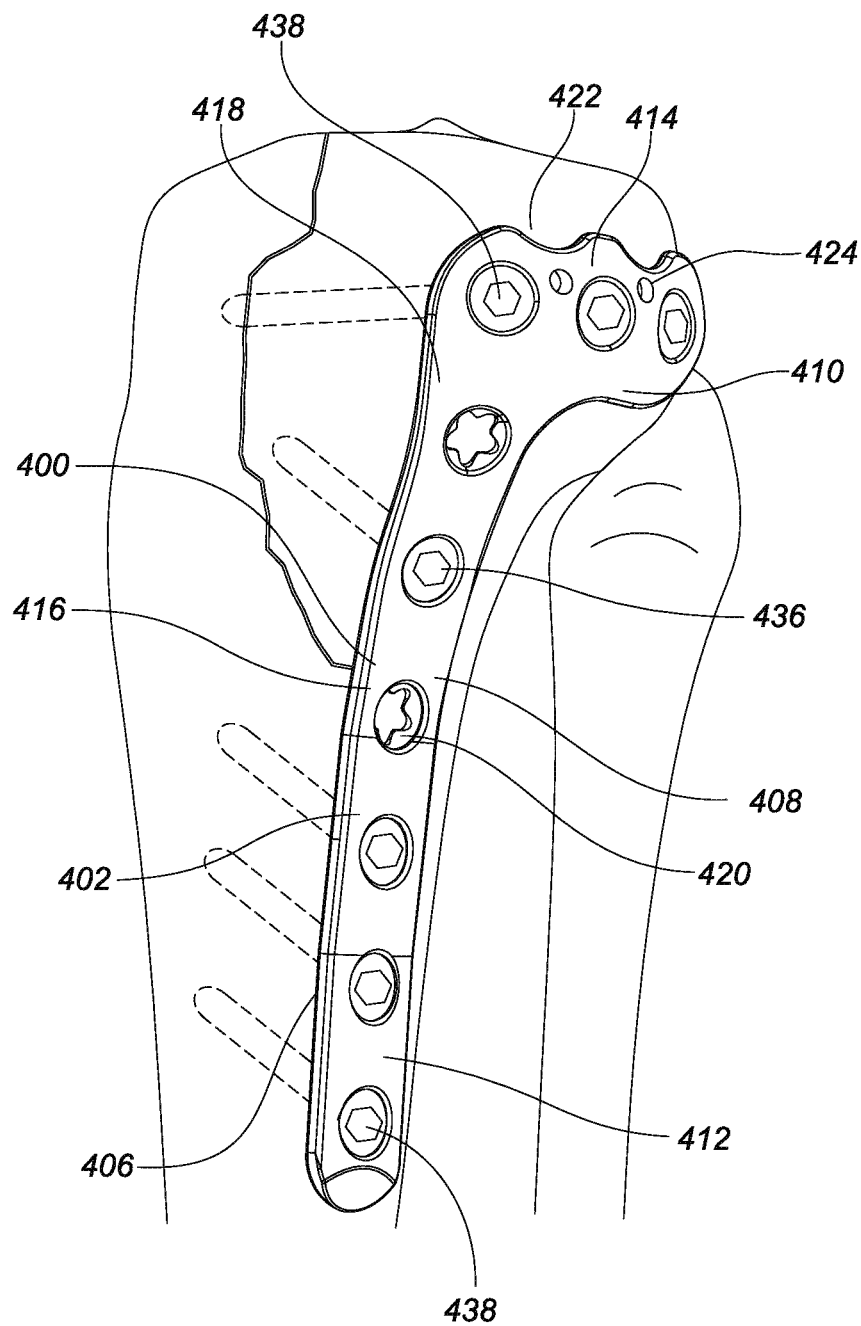
FIG. 39 is a posterior view of portions of a tibia and fibula with an installed lateral proximal tibia plate according to one embodiment of the invention.

FIG. 39 is a posterior view of portions of a tibia and fibula with an installed lateral proximal tibia plate according to one embodiment of the invention. Plate 400 includes an exterior surface 402, a bone contacting or partially bone contacting interior surface 404, a left edge 406, a right edge 408, a head end 410, and a shaft end 412. Exterior surface 402 may be generally convex, flat, or shaped as otherwise desired. Interior surface 404 may be generally concave, flat, or shaped as otherwise desired. Interior surface 404 can contain one or more indentations or undercuts which traverse across the interior surface 404 to modify flexibility of the plate, reduce bone contact, or other purposes. The plate 400 is generally "L" shaped, the foot of the "L" forming the head 414 that is ultimately installed adjacent the lateral condyle of the tibia. A transition 418 transitions to a shaft 416 that preferably features a chamfered end.

The plate 400 lies along the lateral aspect of the proximal tibia. A five degree posterior tilt in the transition section 418 aligns opening 420 with the contour of the lateral tibial condyle. Plate coverage extending down the shaft 416 is enhanced by imparting a three degree sagittal twist (counterclockwise, proceeding toward head 414 in the plate 400 shown in the drawings) in the plate's proximal segment, which can include transition portion 418. Head portion 414 forms a concavity that conforms to the convexity of the lateral condyle. The head end 414 preferably features one or more scallops 422 to accommodate lag or rafter screws that can be used to reinforce the articular surfaces of the tibia. Scallops 422, if used, can be formed of any desired shape generally to help alleviate interference between plate 400 and the lag screws. The plate preferably does not conform precisely flush to the diaphyseal/metaphyseal transition of the tibia; the non correspondence allows compression or mid portions of plate 400 against bone for buttressing effect.

FIG. 39 shows a compression screw 436 across the fracture, with the head 414 receiving three locking screws 438 and the shaft 416 receiving three locking screws 438 on the other side of the fracture from the head 414.

Figure 40:
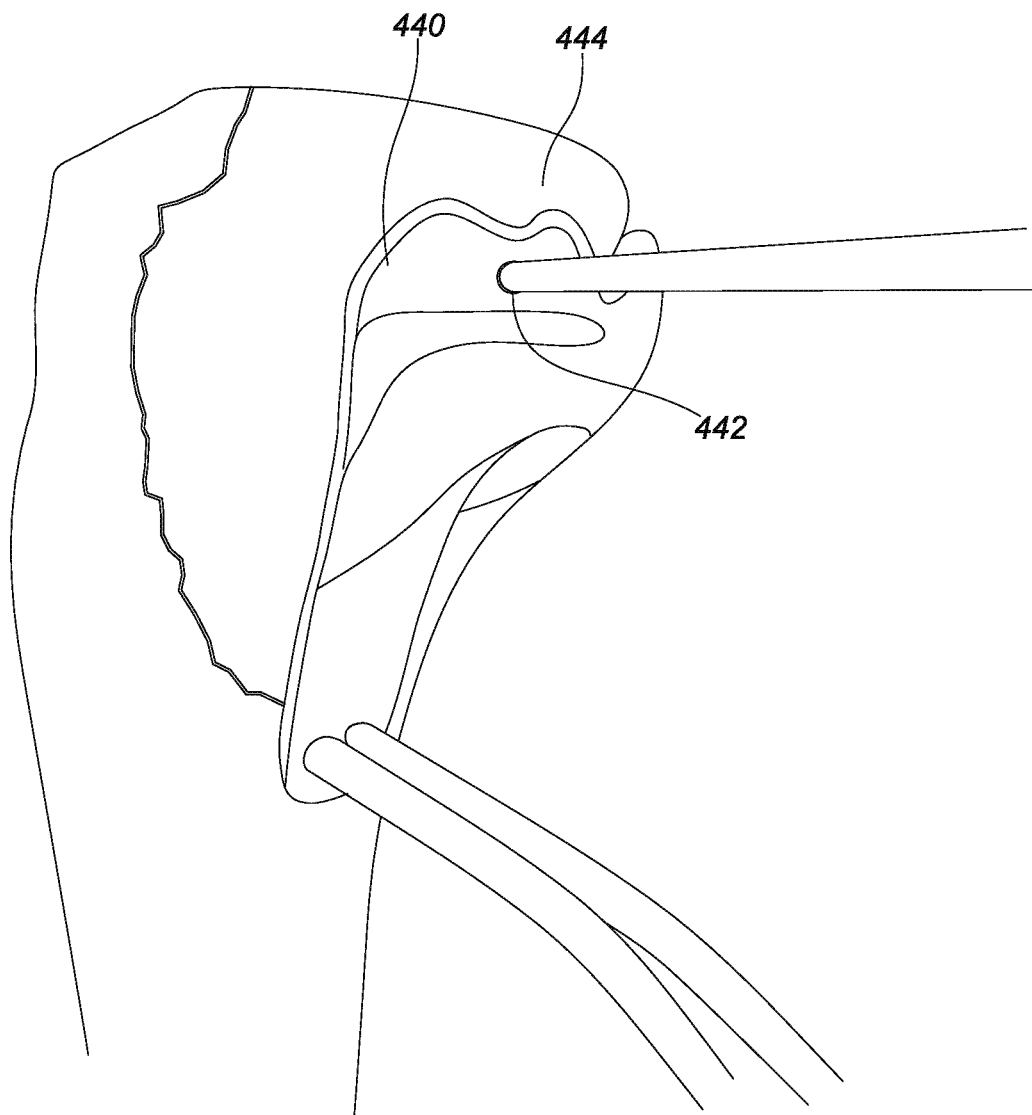
FIG. 40 is a posterior view of portions of a tibia with a lateral proximal tibial guide according to one embodiment of the invention.

Provisional openings 424 can be included in head 414 to accept K-wires or other structure for temporary placement of the plate 400 on bone, for provisional fixation of bone elements, and/or for visualization of screw trajectory as desired. Such openings 424 are also potentially useful in connection with guide 440 shown in FIG. 40 that allows visualization of plate position and provides a template for independent lag screw placement relative to scallops 422 of plate 400. K-wires can be inserted through the two proximal holes 442 to aid in provisional fixation and fracture reduction, together with such visualization. The guide 440 can be removed over the K-wires and the plate 400 applied over the K-wires if desired.

Plate 400 preferably features polyaxial openings 420 as disclosed in connection with openings 220 of plate 200, and a thickness as disclosed in connection with plate 200. It is preferably formed of the material and by the techniques disclosed in connection with plate 200. Additionally, plate 400 can contain other types of threaded or nonthreaded openings and/or slots as disclosed in this document.

Figure 41A:
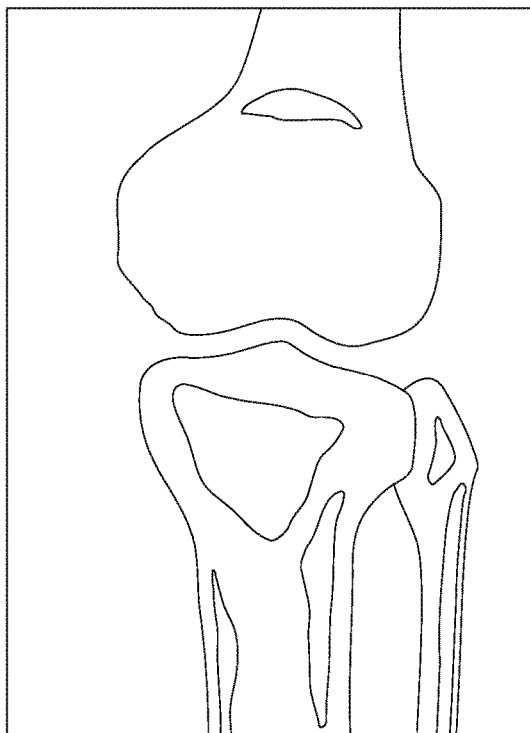
FIGS. 41a and 41b are radiographs showing an installed plate of FIG. 39 and the bone in which it is installed.
Figure 41B:
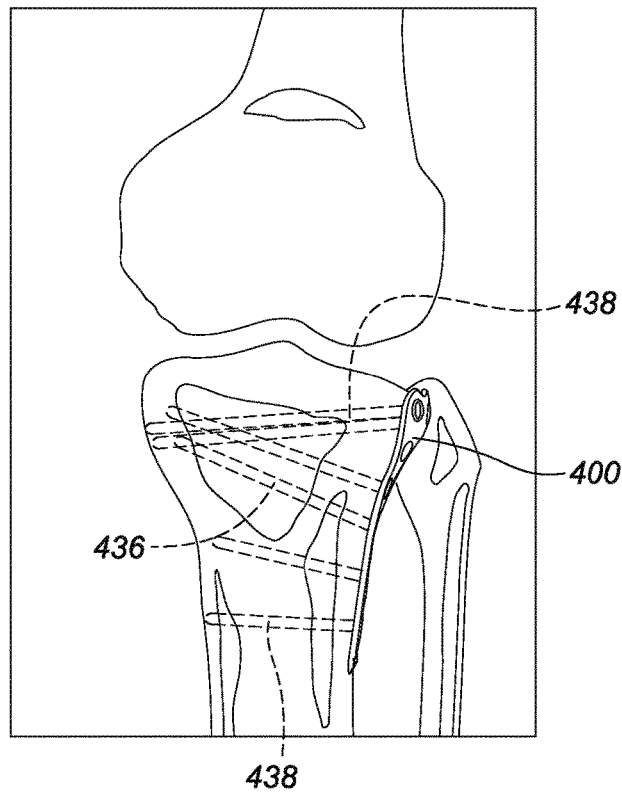
Figure 42:
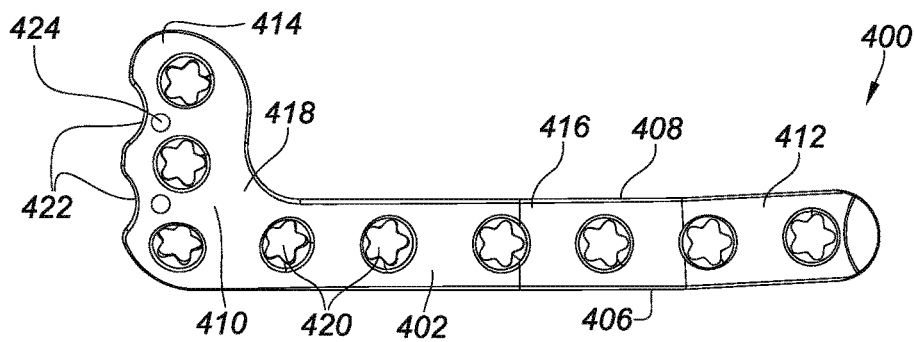
FIG. 42 is a top view of the plate of FIG. 39.
Figure 45:
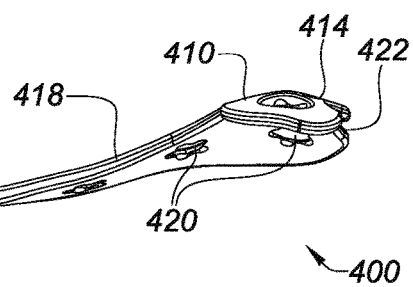
FIG. 45 is a right-side elevational view of the plate of FIG. 39.
Figure 43:
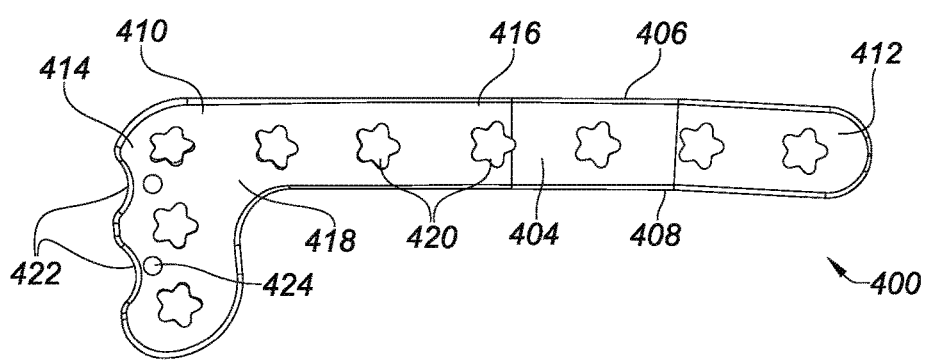
FIG. 43 is a bottom view of the plate of FIG. 39.
Figure 44:
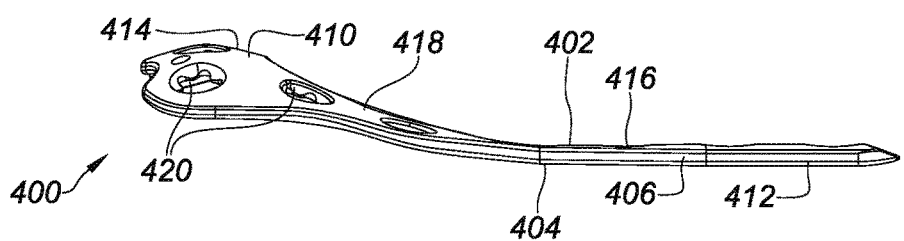
FIG. 44 is a left-side elevational view of the plate of FIG. 39.
Figure 46:
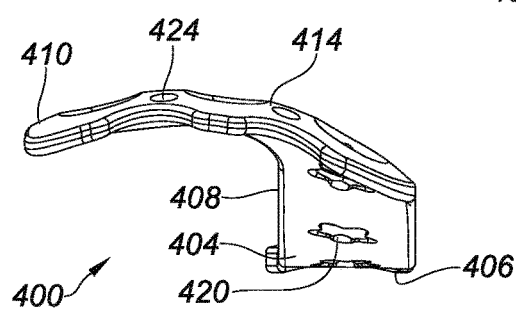
FIG. 46 is a head-end view of the plate of FIG. 39.
Figure 47:
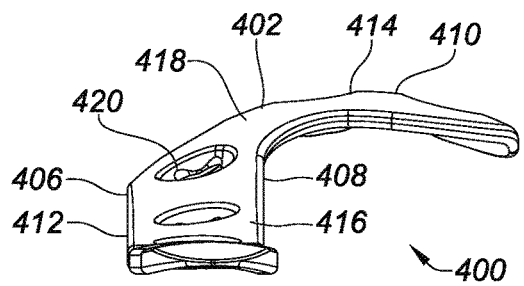
FIG. 47 is a shaft-end view of the plate of FIG. 39.

FIG. 41*b* is a radiograph of an installed lateral proximal tibia plate 400. FIGS. 42-47 show various views of plate 400.

Posteromedial Proximal Tibia Plates

Figure 48:
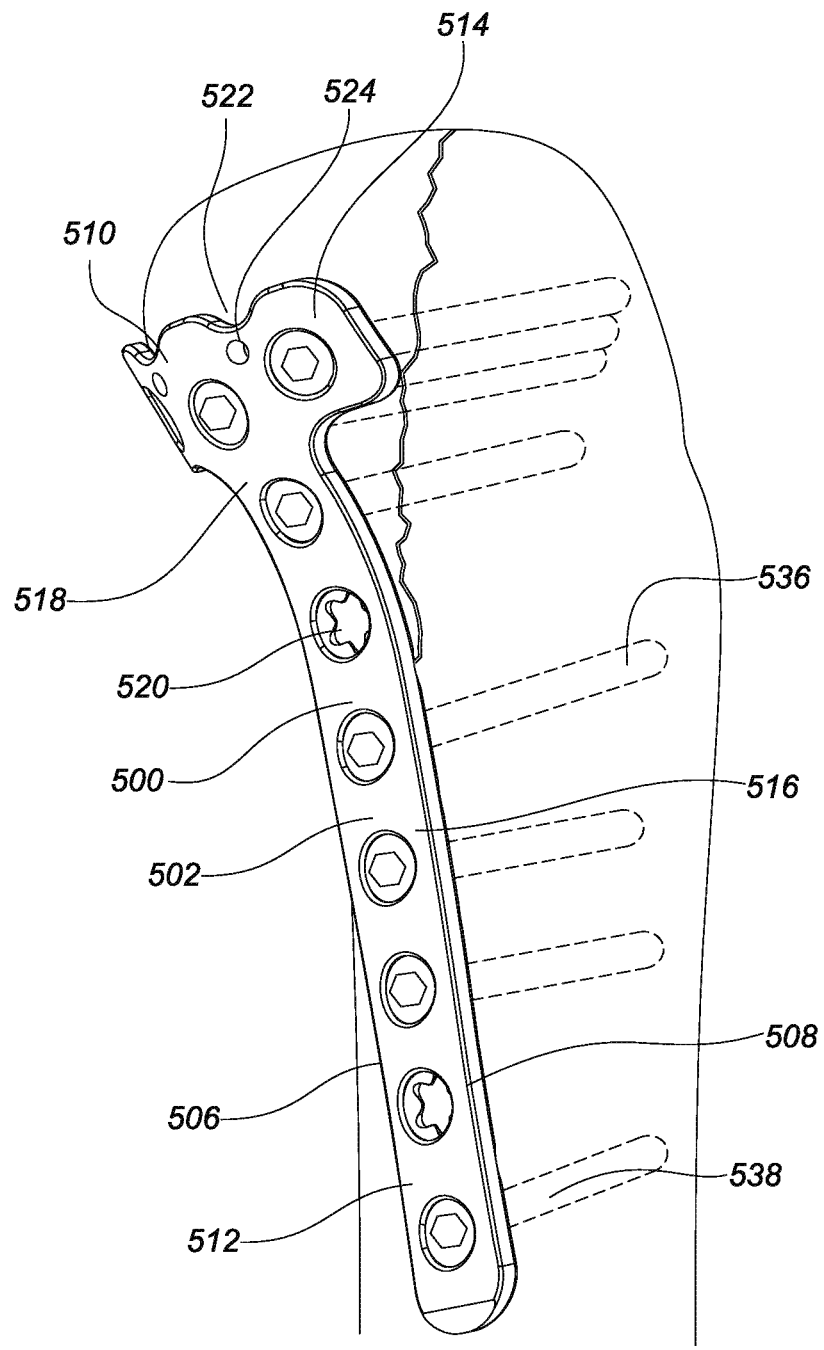
FIG. 48 is a medial view of portions of a tibia with an installed posteromedial proximal tibial plate according to one embodiment of the invention.

FIG. 48 is a medial view of portions of a tibia with a posteromedial proximal tibia plate according to an embodiment of the invention installed. Plate 500 includes an exterior surface 502, a bone contacting or partially bone contacting interior surface 504, a left edge 506, a right edge 508, a head end 510 and a shaft end 512. Exterior surface 502 may be generally convex, flat, or shaped as otherwise desired. Interior surface 504 may be generally concave, flat, or shaped as otherwise desired. Interior surface 504 can contain one or more indentations or undercuts (shown as numeral 521) which traverse across the interior surface 504 to modify flexibility of the plate, reduce bone contact, or other purposes. Head 514 generally forms the top of a "T" with respect to shaft 516. A transition portion 518 imparts a posterior angle in plan view, or medial angle in side view, proceeding from shaft 516 to head 514. Additionally, an axial twist (counterclockwise proceeding to head 514 in the plate 500 shown in the drawings) allows the head 514 to conform more closely to the medial condyle. The head 514 forms a concavity that generally conforms to the convexity of the medial condyle.

Head end 510 preferably includes scallops 522 for purposes of accommodating lag screws as disclosed in connection with plates 400. Plate 500 can also contain provisional openings 524 as disclosed in connection with plates 400 to accommodate K-wire or other provisional fixators for purposes of visualization of screw trajectory, provisional fixation and as otherwise desired. Shaft end 512 preferably features a chamfered portion for percutaneous insertion.

Figure 49A:
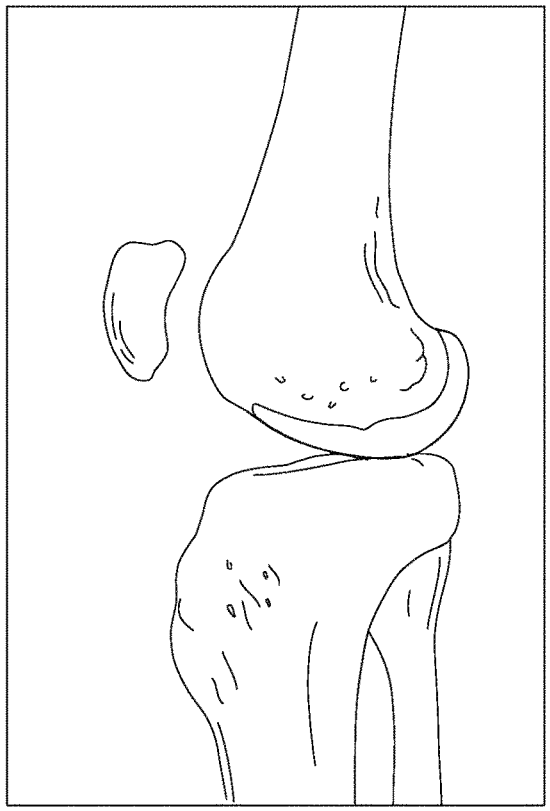
FIGS. 49a and 49b are radiographs of the plate of FIG. 48 and the bone in which it is installed.
Figure 49B:
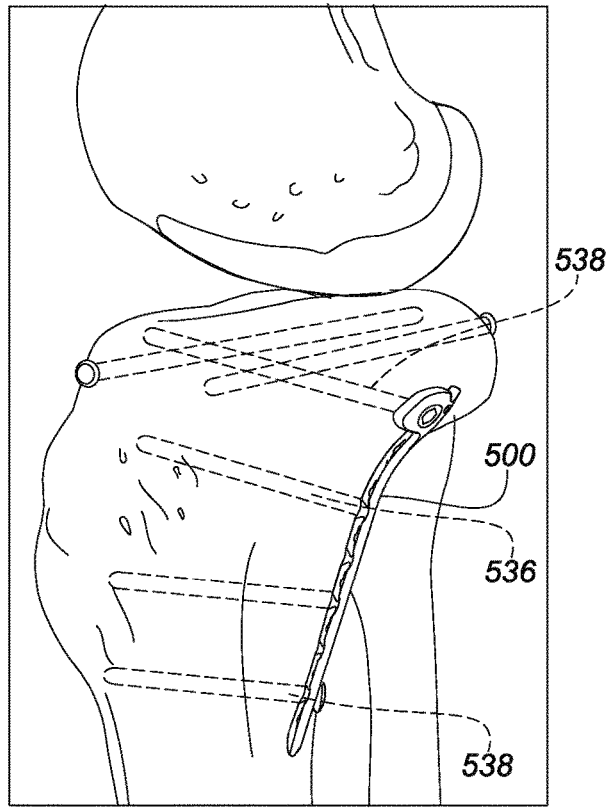

FIG. 49*b* is a radiograph that shows a compression screw 536 inserted through an opening 520 across the fracture. Three locking screws 538 are inserted through the head and four locking screws 538 are inserted along the shaft. FIGS. 50-55 show various views of plate 500.

Plate 500 preferably features polyaxial openings 520 as disclosed in connection with openings 220 of plate 200, and a thickness as disclosed in connection with plate 200. It is preferably formed of the material and by the techniques disclosed in connection with plate 200. Additionally, plate 500 can include other threaded or nonthreaded openings and/or slots as disclosed in this document.

Medial Distal Tibia Plates

Figure 56:
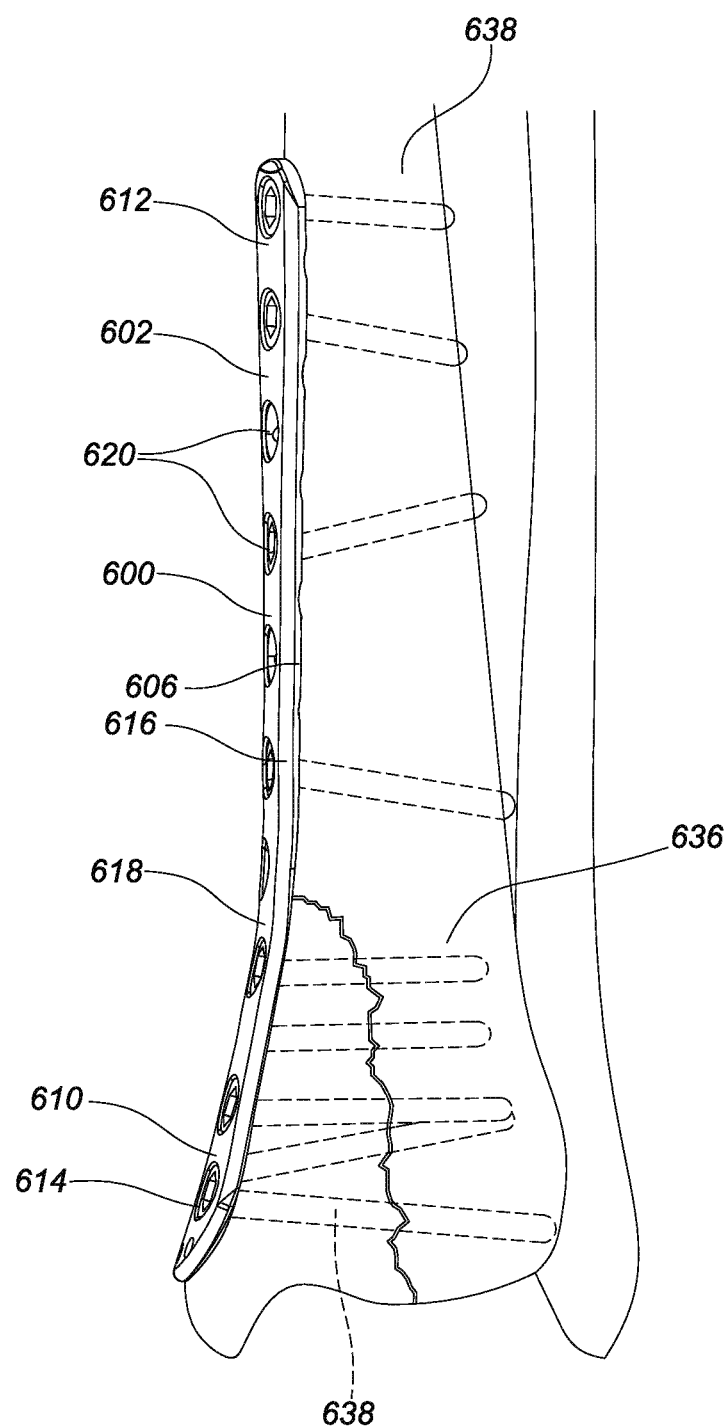
FIG. 56 is a view of portions of a tibia and fibula with an installed medial distal tibia plate according to one embodiment of the invention.
Figure 61:
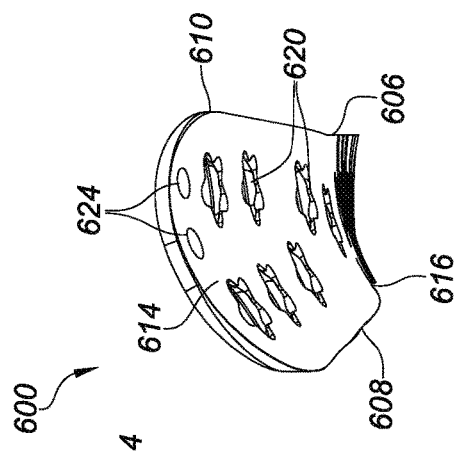
FIG. 61 is a head-end view of the plate of FIG. 56.
Figure 62:
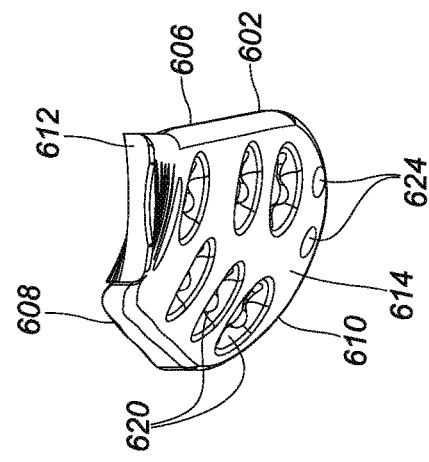
FIG. 62 is a shaft-end view of the plate of FIG. 56.
Figure 59:
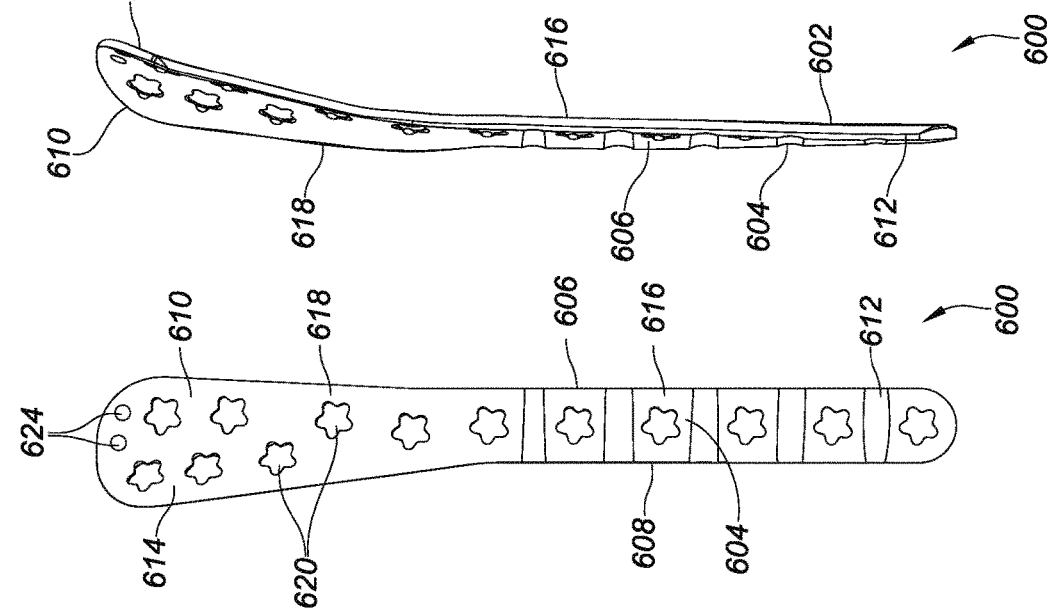
FIG. 59 is a left-side elevational view of the plate of FIG. 56.
Figure 58:
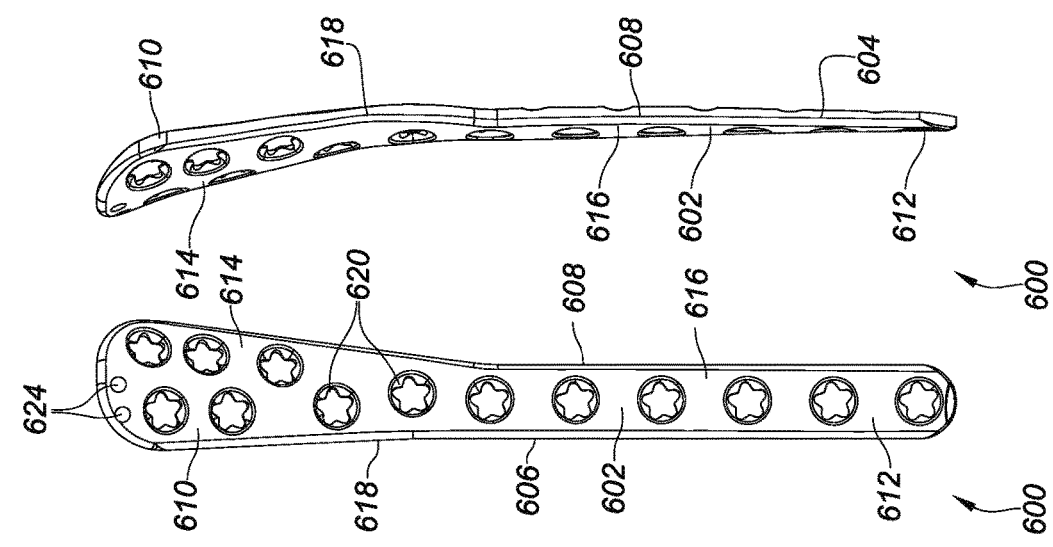
FIG. 58 is a bottom view of the plate of FIG. 56.
Figure 60:
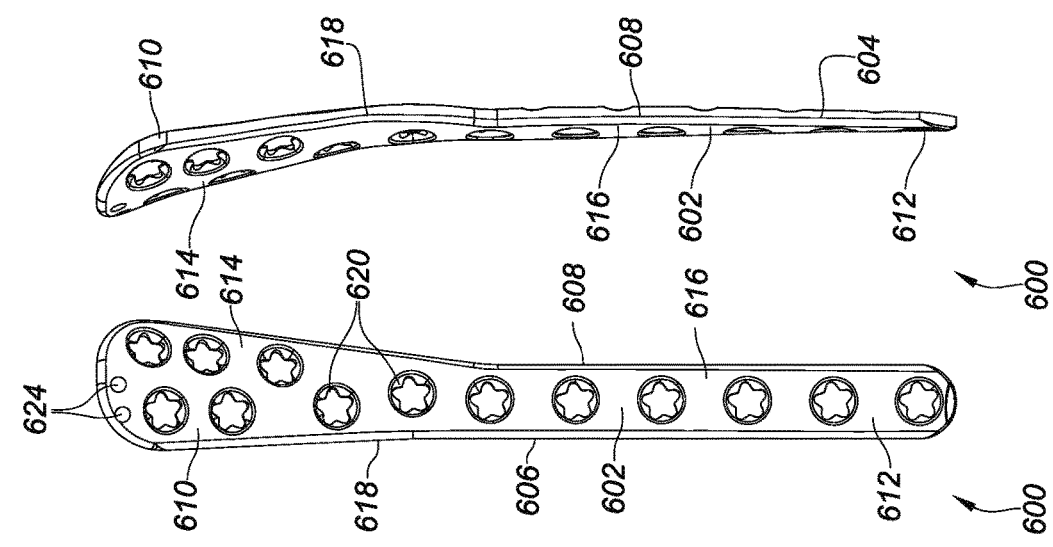
FIG. 60 is a right-side elevational view of the plate of FIG. 56.
Figure 57:
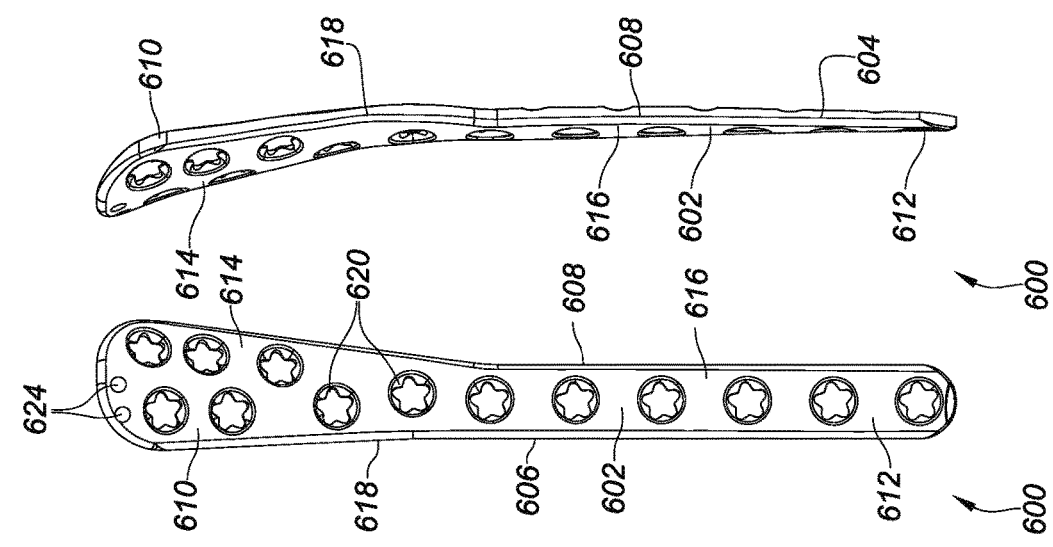
FIG. 57 is a top view of the plate of FIG. 56.

FIG. 56 is an anterior view of distal portions of a tibia and fibula with a medial distal tibia plate 600 according to an embodiment of the invention installed. Plate 600 includes an exterior surface 602, a bone contacting or partially bone contacting interior surface 604, a left edge 606, a right edge 608, a head end 610 and a shaft end 612. Exterior surface 602 may be generally convex, flat, or shaped as otherwise desired. Interior surface 604 may be generally concave, flat, or shaped as otherwise desired. Interior surface 604 can contain one or more indentations or undercuts which traverse across the interior surface 604 to modify flexibility of the plate, reduce bone contact, or other purposes. The shaft 616 transitions to a transition portion 618 which flares to form a head 614 that is flared and generally cupped to accommodate portions of the medial malleolus or distal tibia. The concavity on the interior surface 604 of head 614 allows openings 620 to be oriented so that screws 638 can converge in metaphyseal portions of the tibia. The distalmost openings 620 are preferably positioned just superior to the plafond. The plate 600 features a sagittal twist in at least the transition portion 618 (clockwise proceeding toward head 614). The openings 620 in head 614 are preferably staggered to allow for a greater concentration of locking screws 638 into the metaphyseal portion of the tibia, and also for those screws to converge for additional fixation benefits. FIG. 56 shows a compression screw 636 placed across the fracture with locking screws 638 inserted proximal to the fracture and other locking screws 638 through the head 614.

Provisional openings 624 as discussed in connection with plate 400 can be used. Plate 600 preferably features polyaxial openings 620 as disclosed in connection with openings 220 of plate 200, and a thickness as disclosed in connection with plate 200. It is preferably formed of the material and by the techniques disclosed in connection with plate 200. Additionally, plate 600 can contain other types of threaded or nonthreaded holes and/or slots as disclosed in this document.

FIGS. 57-62 show various views of plate 600 that make more apparent, among other things, the cupped shape of the head 614 and the sagittal twist.

Anterior Distal Tibia Plates

Figure 63:
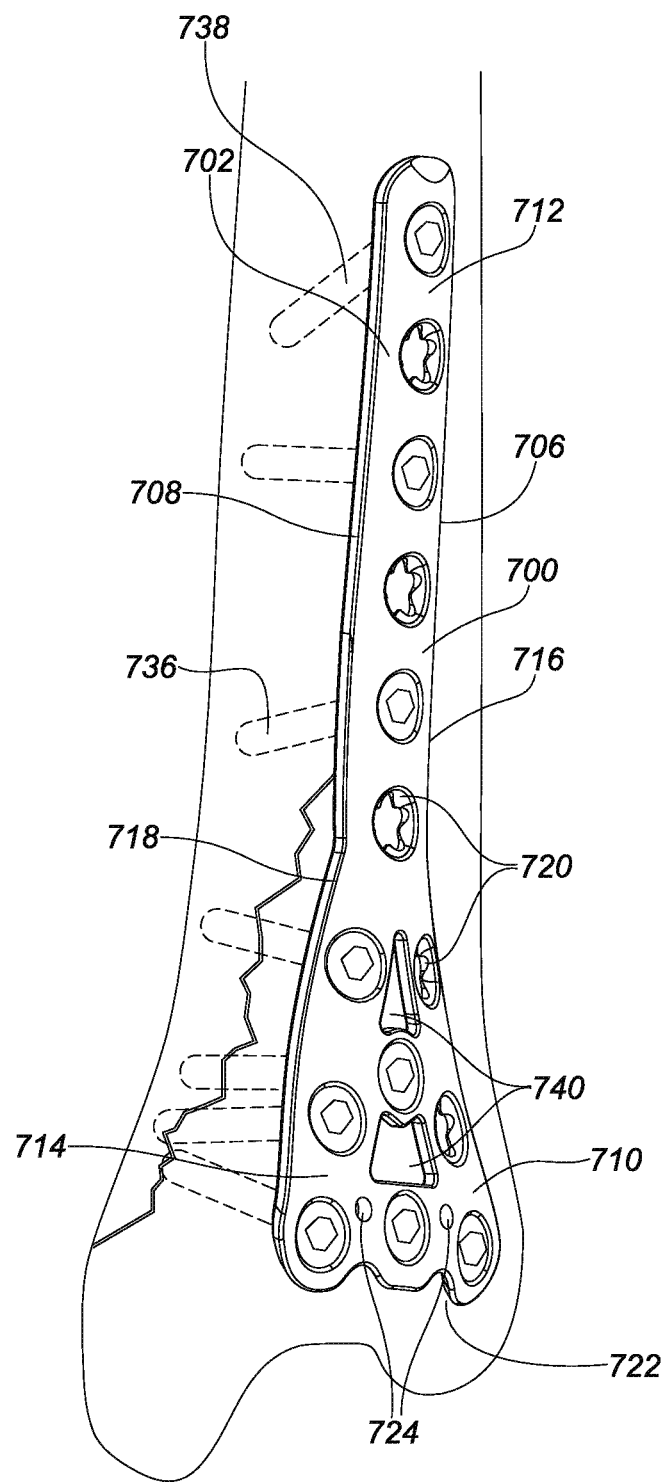
FIG. 63 is an anterior view of a portion of a tibia with an installed anterior distal tibial plate according to one embodiment of the invention.

FIG. 63 shows an anterior view of distal portions of a tibia with an anterior distal tibia plate 700 according to one embodiment of the invention installed. Plate 700 includes an exterior surface 702, a bone contacting or partially bone contacting interior surface 704, a left edge 706, a right edge 708, a head end 710 and a shaft end 712. Exterior surface 702 may be generally convex, flat, or shaped as otherwise desired. Interior surface 704 may be generally concave, flat, or shaped as otherwise desired. Interior surface 704 can contain one or more indentations or undercuts which traverse across the interior surface 704 to modify flexibility of the plate, reduce bone contact, or other purposes. The shaft 716 transitions to a transition portion 718 that angulates anteriorally as does, preferably, head 714, with respect to shaft 716. The transition 718 and head 714 form a delta shape to accommodate fixation into the metaphyseal portion of distal tibia. Material may be removed or omitted to form windows 740 which can be shaped as desired. Windows 740 can help with respect to bone loss and also provide additional opportunities for fixation. Head 714 features a generally concave inner surface 704 to accommodate the general convex shape of the anterior distal tibia. Head end 710 can include one or more scallops 722 that can be formed to allow plate 400 to accommodate or minimally interfere with placement of lag screws or other fixation screws. Provisional openings 724 can be provided as discussed in connection with plate 400. Preferably, the shaft end 712 features a chamfer for percutaneous insertion.

Plate 700 preferably features polyaxial openings 720 as disclosed in connection with openings 220 of plate 200, and a thickness as disclosed in connection with plate 200. It is preferably formed of the material and by the techniques disclosed in connection with plate 200. Additionally, plate 700 can contain other types of threaded or nonthreaded openings and/or slots as disclosed in this document.

Figure 64:
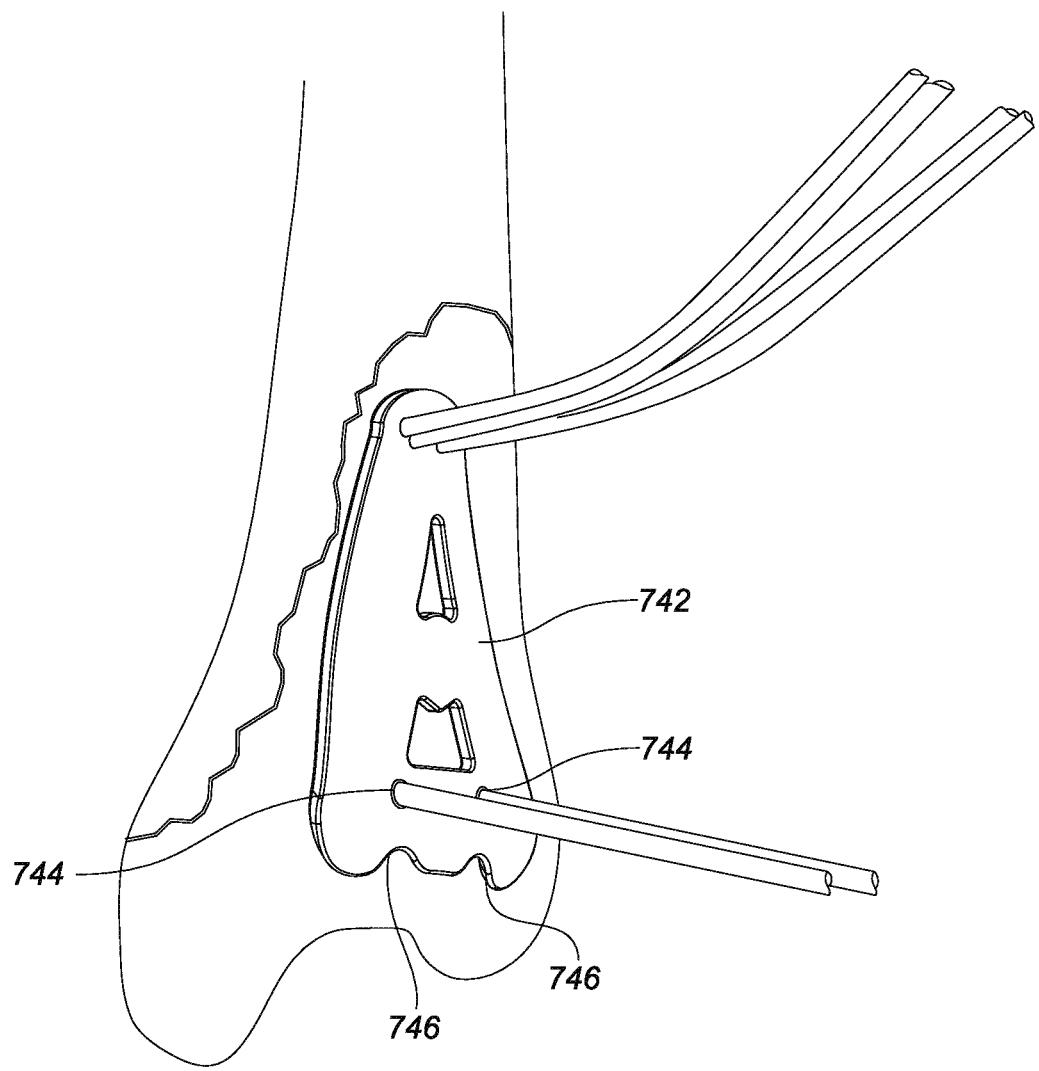
FIG. 64 is an anterior view of a portion of a tibia with an anterior distal tibial guide according to one embodiment of the invention.

FIG. 64 shows an anterior distal tibia positioning guide 742 for use during installation of plate 700. Guide 742 can feature provisional openings 744 and scallops 746 such as the kinds disclosed in connection with guide 440 disclosed above. Guide 744 can allow visualization of plate 700 position and provide a template for independent lag screw placement in the distal tibia relative to scallops 722 in plate 700. K-wires can be inserted through the two distal provisional holes 744 to aid with provisional fixation and fracture reduction. The guide 742 can be removed over the K-wires and the selected plate 700 then applied over them.

Figure 65A:
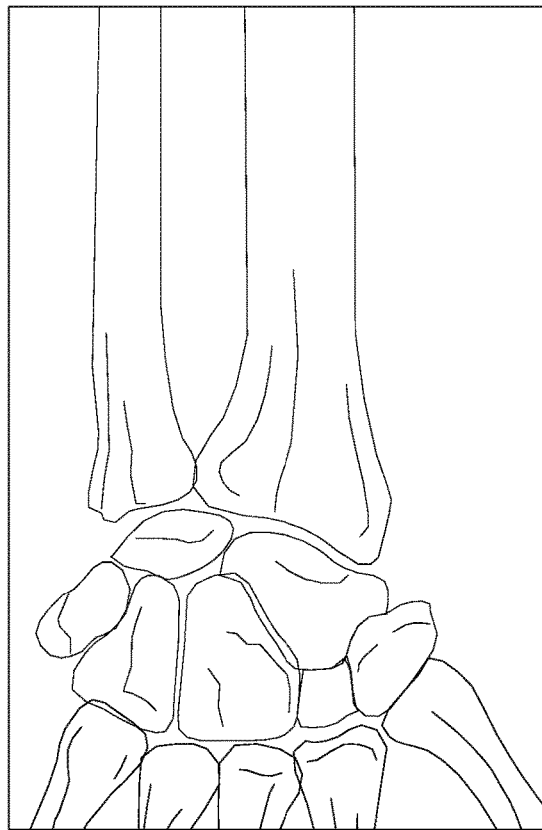
FIGS. 65a and 65b are radiographs of the anterior distal tibia plate of FIG. 63 and the bone in which it is installed.
Figure 65B:
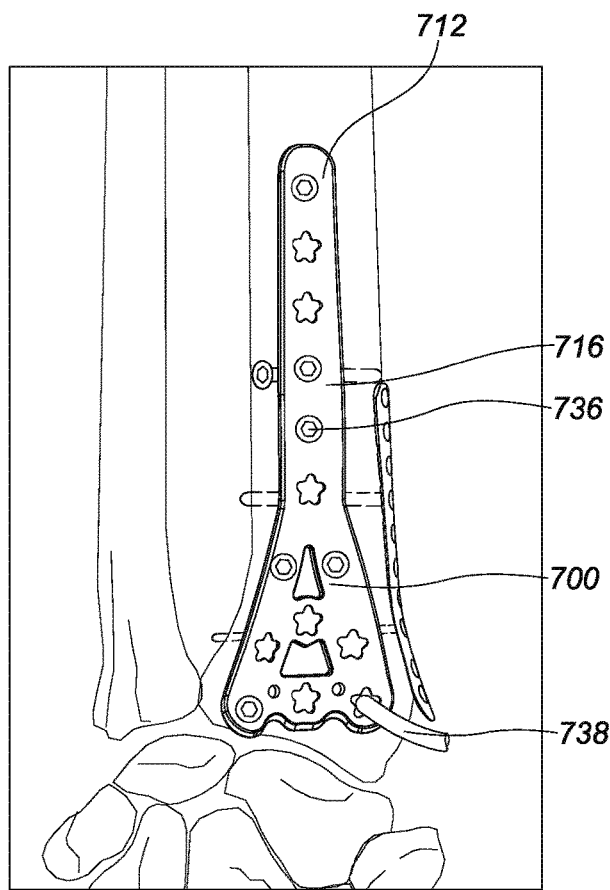

FIG. 65b is a radiograph that shows a plate 700 installed on a tibia. FIGS. 66-71 show various views of plate 700.

Posterior Distal Tibia Plates

Figure 72:
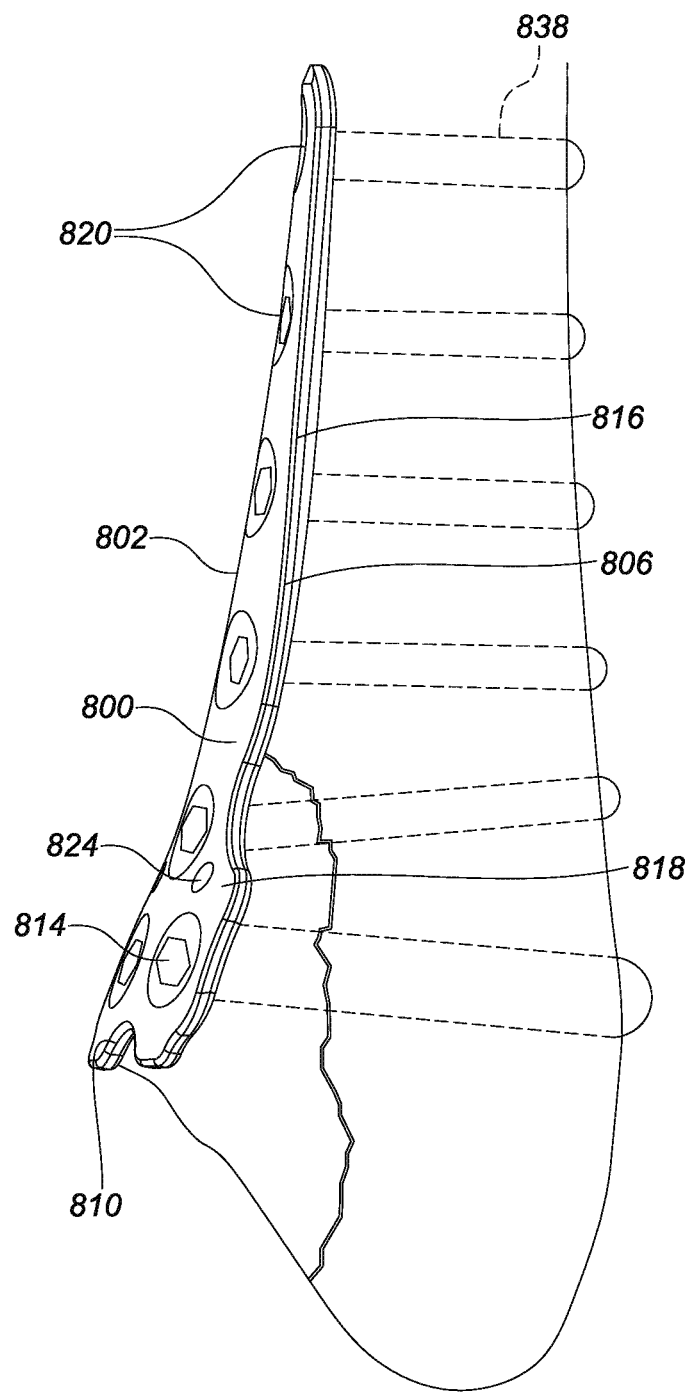
FIG. 72 is a medial view of a portion of a tibia with an installed posterior distal tibia plate according to one embodiment of the invention.
Figure 79:
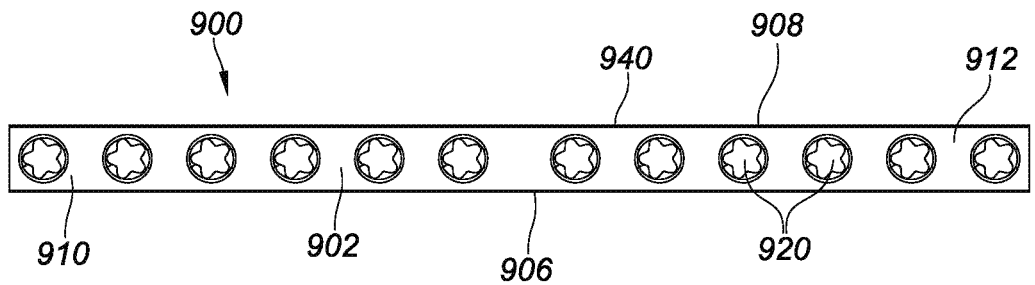
FIG. 79 is a top view of a tubular plate according to one embodiment of the invention.
Figure 82:
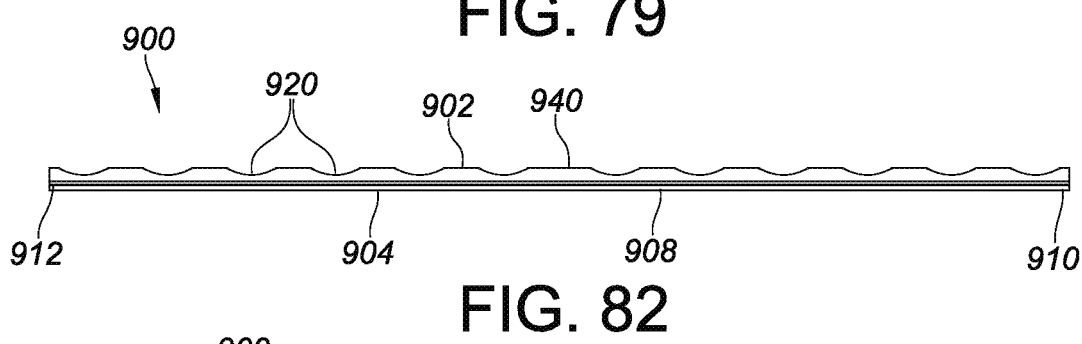
FIG. 82 is a right-side elevational view of the plate of FIG. 79.
Figure 80:
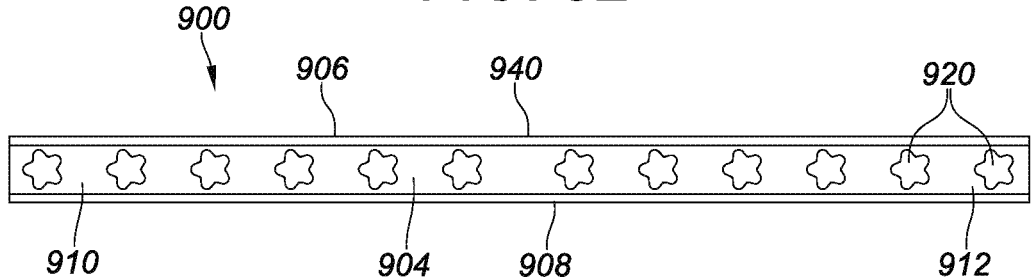
FIG. 80 is a bottom view of the plate of FIG. 79.
Figure 81:
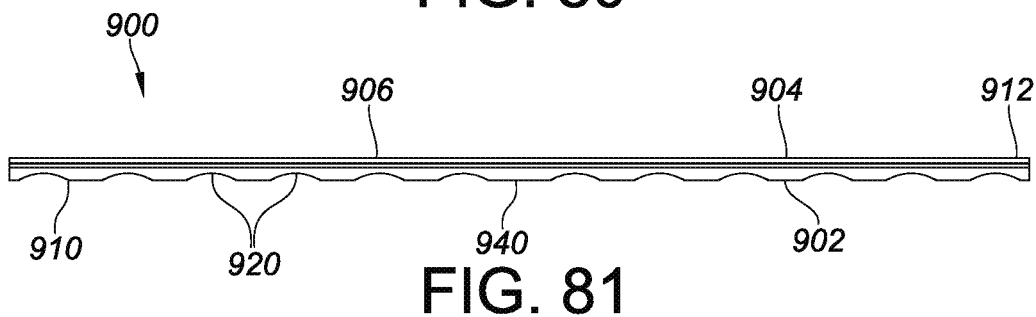
FIG. 81 is a left-side elevational view of the plate of FIG. 79.
Figure 83:
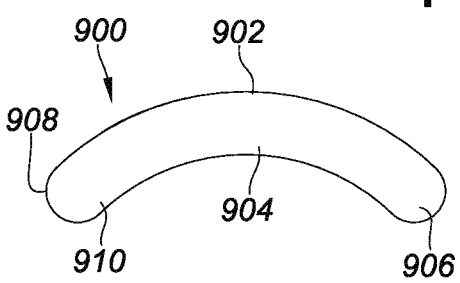
FIG. 83 is a head-end view of the plate of FIG. 79.
Figure 84:
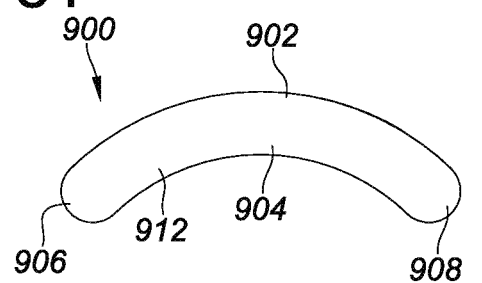
FIG. 84 is a shaft-end view of the plate of FIG. 79.

FIG. 72 is a medial view of a distal portion of a tibia with a posterior distal tibia plate 800 according to one embodiment of the invention installed. Plate 800 includes an exterior surface 802, a bone contacting or partially bone contacting interior surface 804, a left edge 806, a right edge 808, a head end 810 and a shaft end 812. Exterior surface 802 may be generally convex, flat, or shaped as otherwise desired. Interior surface 804 may be generally concave, flat, or shaped as otherwise desired. Interior surface 804 can contain one or more indentations or undercuts which traverse across the interior surface 804 to modify flexibility of the plate, reduce bone contact, or other purposes. Plate 800 is shaped generally to fit the posterior aspect of the distal tibia with head end 810 resting just superior to the tibial plafond. The shaft 816 transitions in transition area 818 to an enlarged head 814, so that the transition 818 and the head 814 accommodate three openings 820. The shaft 816 and transition 818 feature a coronal axial twist (counterclockwise proceeding toward the head in the plate shown in the drawings) to allow conformance to the bone. The transition portion 818 and head 814 also angle posteriorly relative to the shaft 816, as shown in FIG. 72. Plate 800 can include one or more scallops 822, which may be formed as disclosed in connection with plate 400, to accommodate and minimize interference with lag screws in the metaphyseal area of the tibia. Provisional openings 824 can be used as disclosed in connection with plate 400.

Plate 800 preferably features polyaxial openings 820 as disclosed in connection with openings 220 of plate 200, and a thickness as disclosed in connection with plate 200. It is preferably formed of the material and by the technique disclosed in connection with plate 200. Additionally, plate 800 can contain other types of threaded or nonthreaded openings and/or slots as disclosed in this document.

FIGS. 73-78 show various views of plate 800.

Linear Plates

FIGS. 79-84 show a low profile linear plate 900 in accordance with an embodiment of the invention. Plate 900 includes an exterior surface 902, a bone contacting or partially bone contacting interior surface 904, a left edge 906, a right edge 908, a first end 910, and another end 912. Exterior surface 902 may be generally convex, flat, or shaped as otherwise desired. Interior surface 904 may be generally concave, flat, or shaped as otherwise desired. Interior surface 904 can contain one or more indentations or undercuts which traverse across the interior surface 904 to modify flexibility of the plate, reduce bone contact, or other purposes. The plate contains multiple tabbed openings 920 each of which can accept a compression or osteopenic screw 936 or a locking screw 938. Plate 900 also includes a mid portion 940 without a tabbed opening 920, to accommodate greater bending moments located in this area of plate 900. Such a plate 900 can be seen installed on bone in the radiograph shown in FIG. 65b. The linear plate can include scallops along either or both edges as described above, as well as provisional holes and indentations on the interior surface, and/or other features as desired.

Plate 900 preferably features polyaxial openings 920 as disclosed in connection with openings 220 of plate 200, and a thickness as disclosed in connection with plate 200. It is preferably formed of the material and by the techniques disclosed in connection with plate 200. Additionally, plate 900 can contain other types of threaded or nonthreaded holes and/or slots as disclosed in this document.

Low Profile Plates with Slotted Head

Figure 85A:
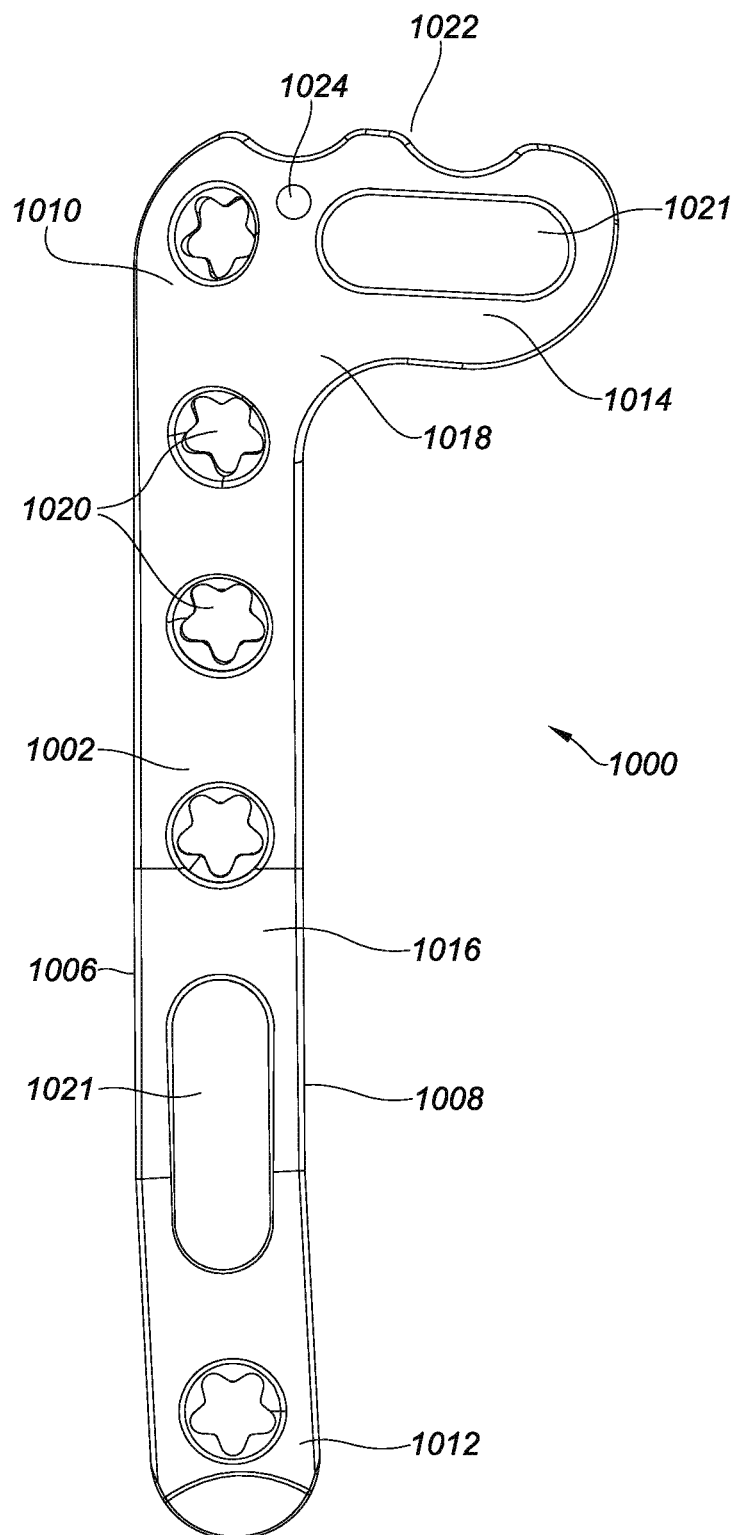
FIGS. 85a and b are views of low profile lateral proximal tibial plates according to one embodiment of the invention with slots or elongated openings.
Figure 85B:
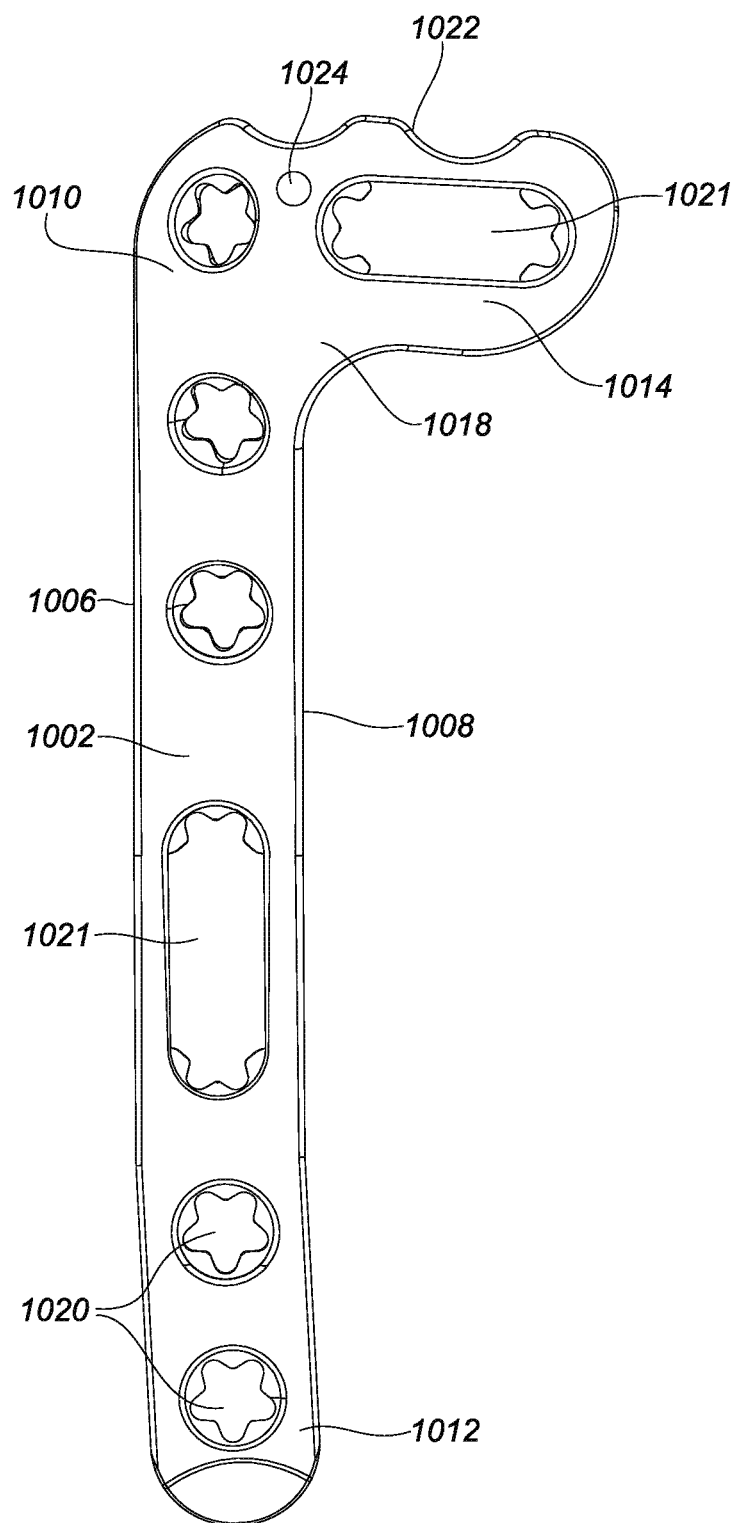

FIGS. 85a and 85b show a low profile plate 1000 with one or more slots 1021 in addition to polyaxial openings 1020 in accordance with an embodiment of this invention. Plate 1000 can be any of the low profile plates disclosed above or any other low profile plate as desired, for any bone, which features the polyaxial openings, low profile and enhanced coutouring features according to embodiments of the invention. FIGS. 85a and 85b show, for purposes of illustration, a modified lateral proximal tibial plate 1000 similar to plate 400, but with a slot or elongated opening in head 1014. Plate 1000 includes an exterior surface 1002, a bone contacting or partially bone contacting interior surface 1004, a left edge 1006, a right edge 1008, a head end 1010, and a shaft end 1012. Exterior surface 1002 may be generally convex, flat, or shaped as otherwise desired. Interior surface 1004 may be generally concave, flat, or shaped as otherwise desired. Interior surface 1004 can contain one or more indentations or undercuts which traverse across the interior surface 1004 to modify flexibility of the plate, reduce bone contact, or other purposes. The head 1014 contains, in this particular embodiment, an elongated opening or slot 1021 which can be partially tabbed or otherwise fitted with polyaxial screw retention structure as shown in FIG. 85b or without tabs or such structure as shown in FIG. 85a. The slot 1021 allows additional flexibility in placement of fixation screws, whether locking in ends of the slot 1021 shown in FIG. 85b, or compression screws which can be inserted in slots 1021 of either plates 1000 shown in FIG. 85a or 85b. Accordingly, a slot 1021 as shown in FIG. 85b, regardless of which plate it may be used on, can accept either cortex, compression, osteopenic screws 1036 or locking screws 1038. Such a slot 1021 can also be formed in the shaft if desired, as shown in FIGS. 85a and b. Scallops 1022 and/or provisional openings 1024 can be included as disclosed above in connection with plate 400.

Plate 1000 preferably features polyaxial openings 1020 as disclosed in connection with openings 220 of plate 200, and a thickness as disclosed in connection with plate 200. It is preferably formed of the material and by the technique disclosed in connection with plate 200.

Spinal Low Profile Plates

Figure 86:
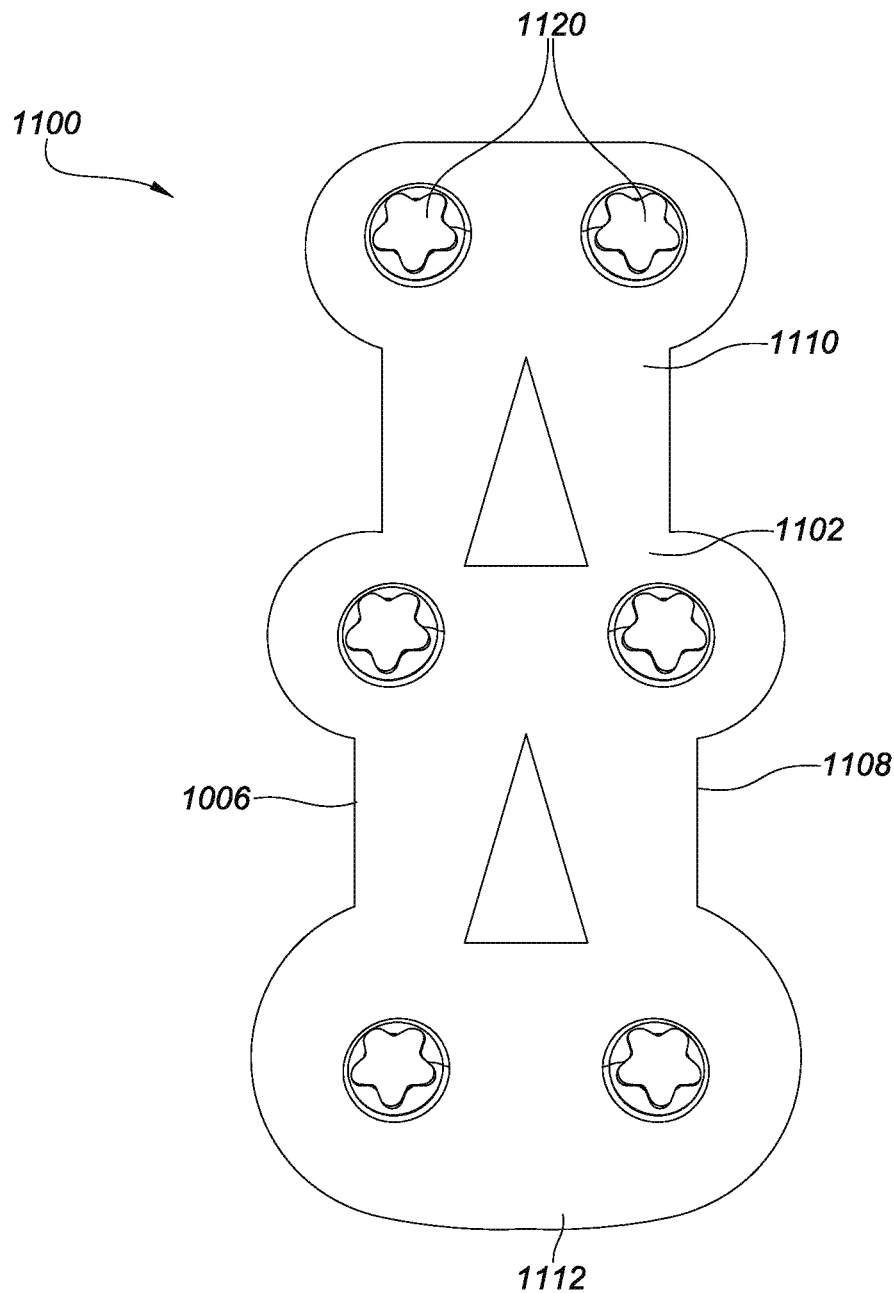
FIG. 86 is a view of a low profile spine plate according to one embodiment of the invention.

FIG. 86 shows a low profile spine plate 1100 in accordance with one embodiment of the invention. Plate 1100 can be shaped like a conventional spine plate and can include an exterior surface 1102, an interior surface 1104, a left edge 1106, a right edge 1108, a first end 1110, and another end 1112. The plate can contain polyaxial openings 1120 which can be formed as disclosed in connection with openings 220 of plates 200. Plate 1100 can have a thickness as disclosed in connection with plate 200, or thinner if desired. Plate 1100 can be formed using materials and techniques as disclosed in connection with plate 200.

Uniaxial/Polyaxial Low Profile Plates

Figure 87:
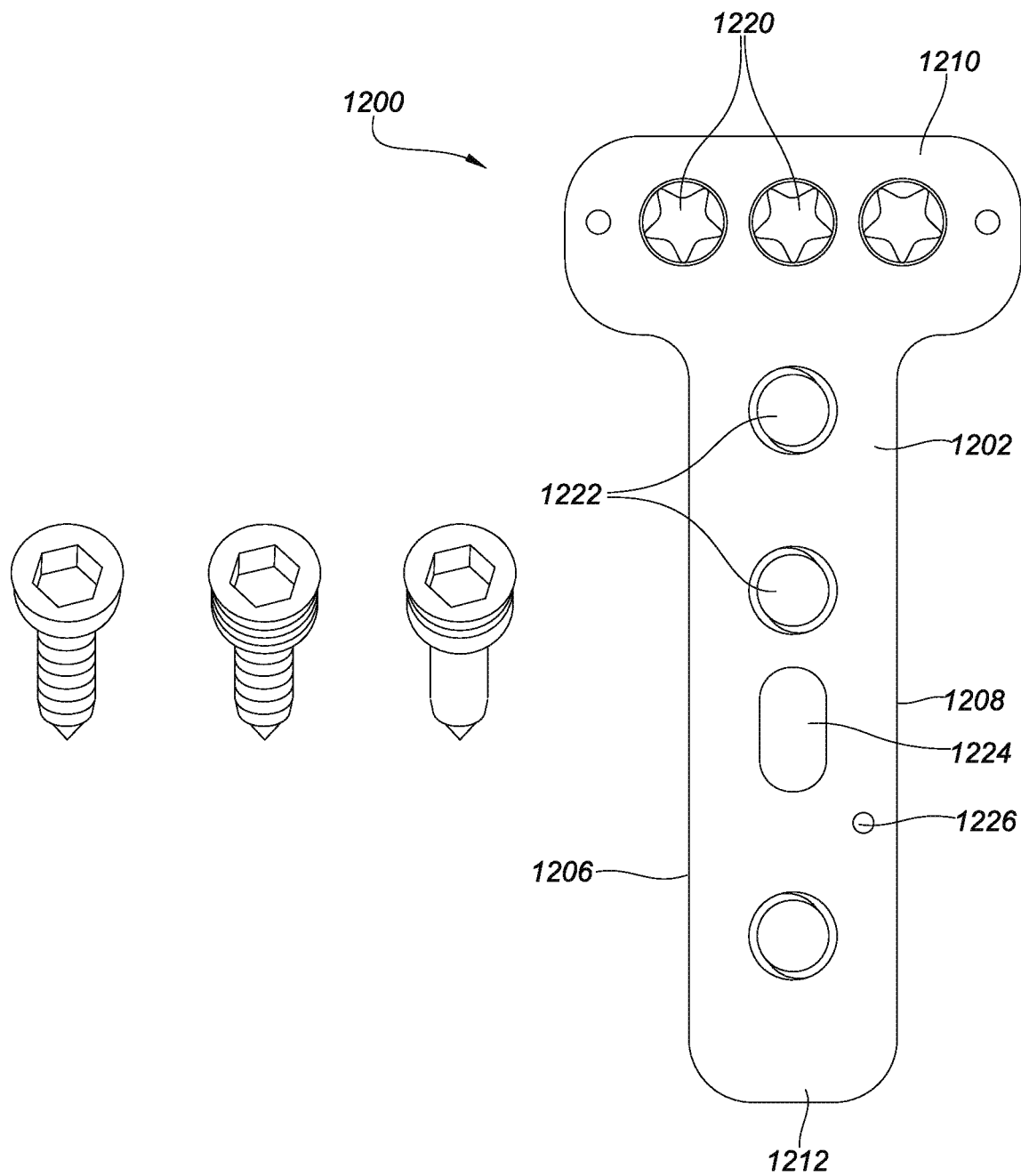
FIG. 87 is a view of a low profile plate according to one embodiment of the invention that has multiple types of openings.

FIG. 87 shows a low profile plate 1200 according to another embodiment of the invention. Plate 1200 is generally like that shown in FIG. 12, except that it can be formed with a thickness as disclosed in connection with plate 200, it can contain polyaxial openings 1220 as disclosed in connection with plate 200, and it has enhanced bone contouring in accordance with embodiments of the invention. Plate 1200 includes an exterior surface 1202, an interior surface 1204, a left edge 1206, a right edge 1208, a first end 1210 and a second end 1212. Exterior surface 1202 may be generally convex, flat, or shaped as otherwise desired. Interior surface 1204 may be generally concave, flat, or shaped as otherwise desired. Interior surface 1204 can contain one or more indentations or undercuts which traverse across the interior surface 1204 to modify flexibility of the plate, reduce bone contact, or other purposes. Plate 1200 may be any of the plates disclosed above or any other desired low profile plate for any bone which features at least one polyaxial opening 1220 as disclosed above in connection with plate 200, and the low profile and enhanced contouring features of embodiments of the invention. Openings 1220 can be formed in the head, shaft, or any other desired portion of a plate. The plate 1200 can also, if desired, contain one or more conventionally threaded openings 1222 at any desired location, such as where locking functionality is needed but polyaxial locking functionality is not needed. Plate 1200 can also contain one or more slots or elongated openings 1224 at any desired location. The slots can be either partially conventionally threaded or tabbed as disclosed in connection with the slots 1021 of FIGS. 85a and 85b. One or more provisional openings 1126 can also be included if desired. Conventionally threaded openings 1222 can accept compression screws, locking screws, or locking pegs as shown in FIG. 12. Plate 1200 can be formed using materials and techniques as disclosed in connection with plate 200.

Low Profile Plates with Slotted Shaft

Figure 88A:
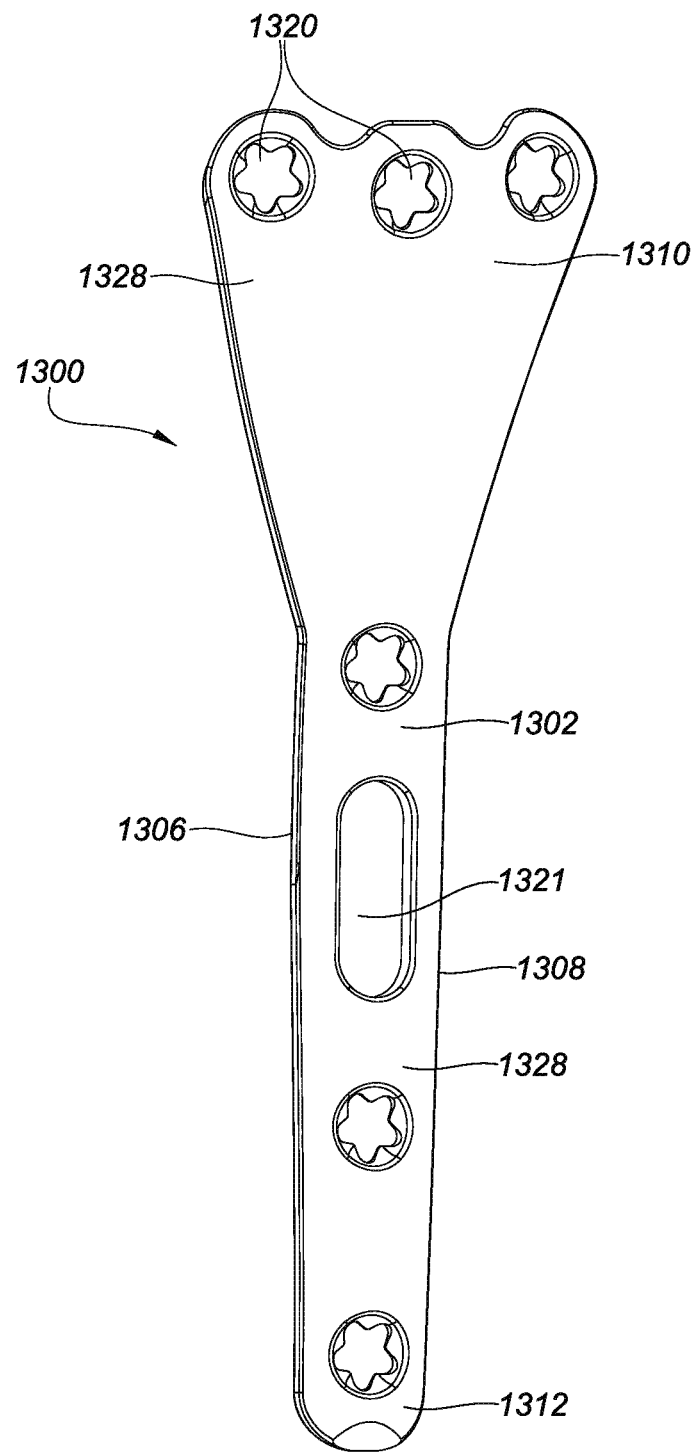
FIGS. 88a and b are views of low profile plates according to one embodiment of the invention that have a slot or elongated opening in the shaft.
Figure 88B:
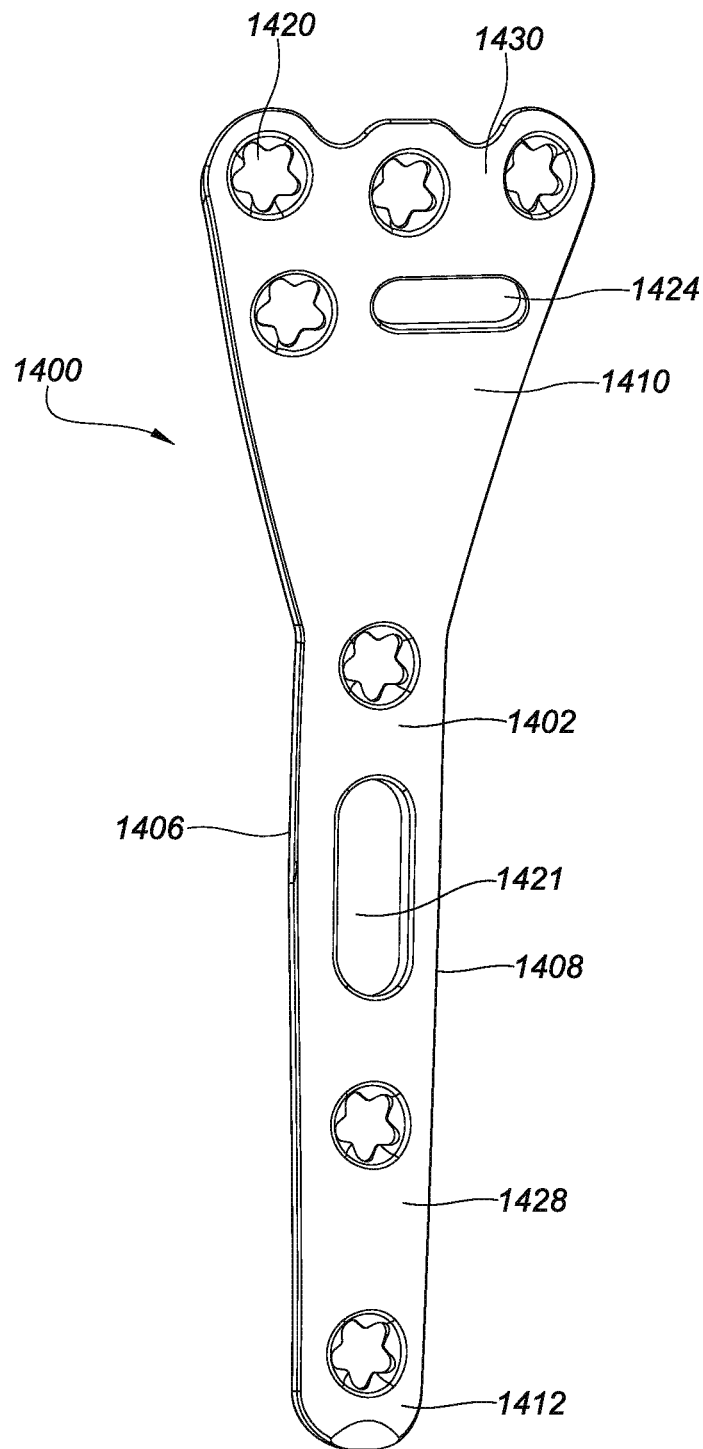

FIGS. 88a and 88b show low profile plates according to an embodiment of the invention that include at least one slot 1321 in the shaft. Plate 1300, shown in FIG. 88a, which can take the shape of any of the low profile plates disclosed in this document, or other low profile shape as desired, for any desired bone surface, includes an exterior surface 1302, an interior surface 1304, a left edge 1306, a right edge 1308, a first end 1310, and a second end 1312. Exterior surface 1302 may be generally convex, flat, or shaped as otherwise desired. Interior surface 1304 may be generally concave, flat, or shaped as otherwise desired. Interior surface 1304 can contain one or more indentations or undercuts which traverse across the interior surface 1304 to modify flexibility of the plate, reduce bone contact, or other purposes. Polyaxial openings 1320 can be formed as disclosed in connection with openings 220 of plate 200. A slot 1321 is included mid plate such as in shaft 1328. The slot 1321 allows additional flexibility in fixation, and can be configured as disclosed in connection with slots 1021 of plate 1000, to accept cortex, compression, osteopenic, locking or other screws.

Plate 1400, shown in FIG. 88b, which can take the shape of any of the low profile plates disclosed in this document, or other low profile shape as desired, for any desired bone surface, includes an exterior surface 1402, an interior surface 1404, a left edge 1406, a right edge 1408, a first end 1410, and a second end 1412. Exterior surface 1402 may be generally convex, flat, or shaped as otherwise desired. Interior surface 1404 may be generally concave, flat, or shaped as otherwise desired. Interior surface 1404 can contain one or more indentations or undercuts which traverse across the interior surface 1404 to modify flexibility of the plate, reduce bone contact, or other purposes. Polyaxial openings 1420 can be formed as disclosed in connection with openings 220 of plate 200. A slot 1424 is included mid plate such as in shaft 1428. The slot 1324 allows additional flexibility in fixation, and can be configured as disclosed in connection with slots 1021 of plate 1000, to accept cortex, compression, osteopenic, locking or other screws. FIG. 88b shows that a slot 1424 can also be included in a head portion 1430 of the plate 1400. Provisional openings, scallops, and other features can also be included in plates such as plates 1300, 1400, if desired. Plates 1300, 1400 can be formed using materials and techniques disclosed in connection with plate 200.

Partial Low Profile Polyaxial Plates

Figure 89A:
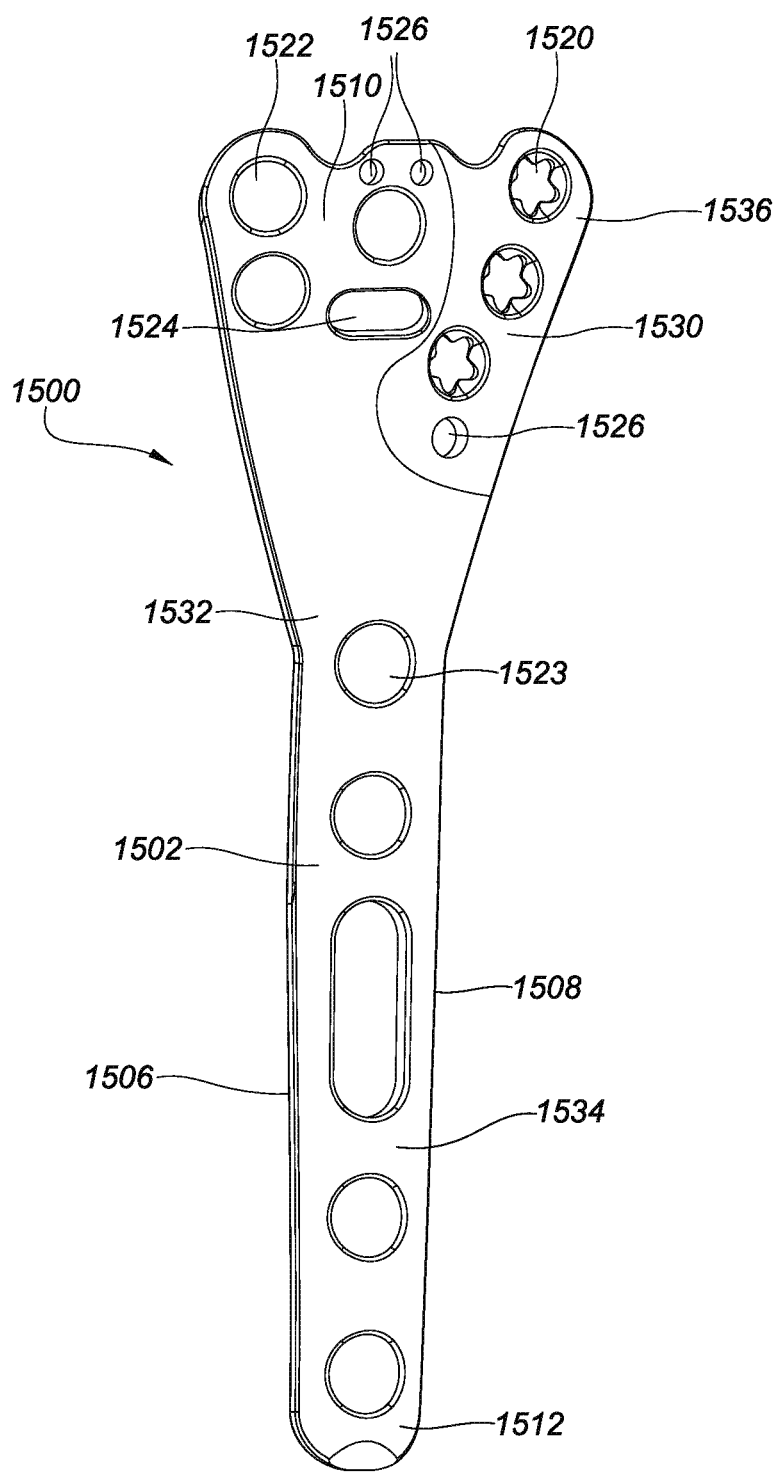
FIGS. 89a, b and c are views of partial low profil—partial physiological load bearing plates according to one embodiment of the invention.
Figures 89B, 89C:
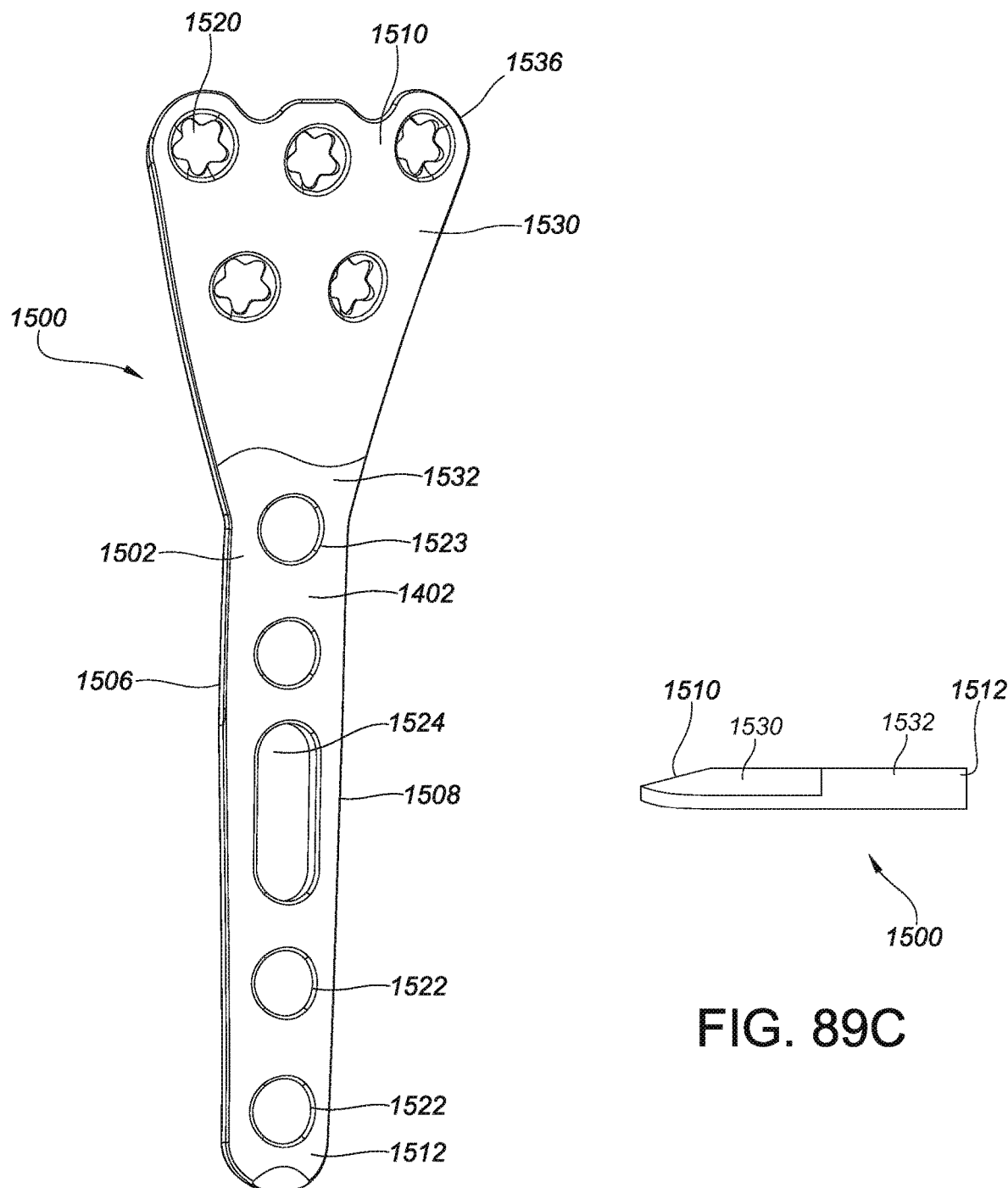

FIGS. 89a and 89b show partial low profile/partial load-bearing plates 1500 according to an embodiment of the invention. Plate 1500 can be shaped as is conventional for a load-bearing plate for any desired bone, or as otherwise desired. Plate 1500 includes an exterior surface 1502, an interior surface 1504, a left edge 1506, a right edge 1508, a head end 1510, and a shaft end 1512. Exterior surface 1502 may be generally convex, flat, or shaped as otherwise desired. Interior surface 1504 may be generally concave, flat, or shaped as otherwise desired. Interior surface 1504 can contain one or more indentations or undercuts which traverse across the interior surface 1504 to modify flexibility of the plate, reduce bone contact, or other purposes. Plate 1500 can contain a low profile section 1530 as disclosed in this document, with thickness as disclosed in connection with plate 200, and polyaxial openings 1520 formed as disclosed for openings 220 in plates 200. Any portion of the plate 1500, including low profile section 1530, load-bearing section 1532 or both, can include one or more provisional openings 1526. Load-bearing portion 1532 can include, as desired, any combination of conventionally threaded openings 1522, non-threaded openings 1523, and conventionally non-threaded, partially threaded or partially-polyaxially locking structured slots 1524. Slots 1524 can be included in the shaft portion 1534 and/or, if desired, in head 1536. The particular plate 1500 shown in FIG. 89a includes in its head 1536 a low profile section adapted to accommodate a metaphyseal portion of a bone. A portion of the head 1536 of plate 1500 of FIG. 89a is shown in cross section in FIG. 89c. Plate 1500 shown in FIG. 89b is similar in concept to that shown in FIG. 89a except that the entire head 1536 is formed as a low profile plate in accordance with embodiments of the invention, while the shaft 1534 is formed as a load-bearing section. In these plates 1500, the load-bearing sections 1532 and the low profile sections 1530 can be demarcated as desired to carry out fixation that allows at least part of the plate to bear physiologic loads such as body weight and another part of the plate 1500 to operate in accordance with the low profile principles disclosed in this document.

Installation of Low Profile Plates

Low profile plates according to certain embodiments of the invention can be installed as follows. They can be used in connection with intramedullary nails, external fixators and/or other devices, wherein the nail or other structure absorbs body load, and the plate is used primarily to buttress fragments, stabilize the fracture and otherwise assist in treatment.

A C-arm can be used for fluoroscopy, including preferably arranged to show the AP plane from lateral positioning. X-rays can be taken ahead of time and an acetate or other template can be provided that allows selection of plate and screw sizes. An incision is made and the plate can be inserted percutaneously or as otherwise desired. Fluoroscopy may be used to ensure that the plate is correctly located. Portions of the metaphyseal area can be opened as desired for reduction of the fracture, access, and other purposes. Wires, forceps and other conventional instruments, components, and techniques can be used to restore and reduce the joint. Provisional fixation holes can be used for K-wires to assist in this process, to provisionally fix the plate to bone, to fix bone fragments and perform reduction, and/or to visualize screw trajectory as desired.

A non-locking screw, such as a cortex, compression or osteopenic screw, can be inserted in one of the openings in the mid portion of the plate to compress that portion against bone to enhance or achieve buttressing effect. The plate can be installed without such compression to perform reinforcement if desired. Drill guides such as those disclosed in PCT/US2007/085210 filed Nov. 20, 2007, which claims priority to U.S. Ser. No. 60/866,665 filed Nov. 21, 2006, both owned by the owner of this document, can be employed as desired. Preferably, two or three holes are filled with locking screws below the fracture and two or three above, although more or fewer holes can be used. The length or orientation of screws can be changed multiple times, such as up to three, with tabbed openings such as those disclosed above in connection with FIGS. 25b and c. Torque can be applied using conventional torque limiters, which are preferably set not to exceed 1.7 Newton-meters or 16 inch pounds. Alternatively, locking screws can be hand torqued for final torquing. Wound closure follows conventional technique.

The foregoing description of exemplary embodiments of the invention is presented for purposes of illustration and description and is not intended to be exhaustive or to limit the invention to the precise forms, structures or techniques disclosed. Modifications and variations to those forms, structures and techniques are possible without departing from the scope or spirit of the above disclosure and the following claims. Alternative embodiments will become apparent to those skilled in the art to which the present invention pertains without departing from its spirit and scope.

The invention claimed is:

1. A polyaxial bone fixation system, the system comprising:
    at least one fastener, the fastener having a head portion and a shaft portion; and
    a bone plate comprising a lower surface, an upper surface and at least one opening extending from the lower surface to the upper surface;
    wherein:
        the at least one opening is adapted and configured to receive the at least one fastener; and
        the head portion of the at least one fastener includes threads, the at least one opening includes a plurality of non-circumferential fins integrally connected to, and protruding therefrom, the plurality of non-circumferential fins form a concave portion protruding from an inner surface of the at least one opening, the plurality of non-circumferential fins each include a base that meet at the inner surface in substantially the same plane, the plurality of non-circumferential fins being arranged and configured to move at least a portion of each fin independently toward the upper surface or toward the lower surface when the at least one fastener is inserted into the at least one opening to secure a position of the at least one fastener relative to the bone plate at any one of a plurality of angles.

2. The polyaxial bone fixation assembly of claim 1, wherein the plurality of non-circumferential fins are provided as a series of concavely indented, inwardly protruding fins that are adapted to interlock with the threads to secure the head portion of the at least one fastener relative to the bone plate.

3. The polyaxial bone fixation assembly of claim 1, wherein the bone plate has a head portion, the at least one opening being located in the head portion of the bone plate.

4. The polyaxial bone fixation assembly of claim 3, wherein the bone plate further comprises one or more of the following: a threaded opening; a non- threaded opening; an opening adapted to receive locking or non-locking fasteners; an opening with fins; a combination slot; or; any combination thereof.

5. The polyaxial bone fixation assembly of claim 1, wherein the plurality of non-circumferential fins include five to eight fins.

6. The polyaxial bone fixation assembly of claim 1, wherein the plurality of non-circumferential fins each include inwardly tapered side surfaces.

7. The polyaxial bone fixation assembly of claim 1, wherein the plurality of non-circumferential fins are arranged and configured to deflect so that each fin is interposed between the threads when the at least one fastener is inserted into the at least one opening.

8. The polyaxial bone fixation assembly of claim 1, wherein the plurality of non-circumferential fins are arranged and configured to deform so that each fin is interposed between the threads when the at least one fastener is inserted into the at least one opening.

9. An orthopedic implant system comprising:
    an orthopedic implant comprising a first bone contacting surface, a second surface opposite the first bone contacting surface, and at least one opening extending from the first bone contacting surface to the second surface; and
    at least one fastener arranged and configured to be inserted into the at least one opening, the at least one fastener having a head portion and a shaft portion;
    wherein the head portion of the at least one fastener includes threads, the at least one opening includes a plurality of non-circumferential fins, each fin being arranged and configured to move independently toward the first bone contacting surface or the second surface to interlock with the threads to secure a position of the at least one fastener relative to the orthopedic implant when the at least one fastener is inserted into the at least one opening at any one of a plurality of angles; and
    wherein the at least one opening further includes a round circumference at the second surface and a jagged circumference formed by the protruding fins at the bone contacting surface.

10. The polyaxial bone fixation assembly of claim 9, wherein the plurality of non-circumferential fins are provided as a series of concavely indented, protruding fins.

11. The polyaxial bone fixation assembly of claim 9, wherein the plurality of non-circumferential fins form a concave portion protruding from an inner surface of the at least one opening.

12. The polyaxial bone fixation assembly of claim 11, wherein the plurality of non-circumferential fins each include a base that meet at the inner surface in substantially the same plane.

13. The polyaxial bone fixation assembly of claim 11, wherein the plurality of non-circumferential fins include five to eight fins.

14. The polyaxial bone fixation assembly of claim 9, wherein the plurality of non-circumferential fins include inwardly tapered side surfaces.

15. The polyaxial bone fixation assembly of claim 9, wherein the plurality of non-circumferential fins are each integrally connected to, and protruding from, an inner surface of the at least one opening or the head portion of the fastener.

16. The polyaxial bone fixation assembly of claim 9, wherein the plurality of non-circumferential fins each have a tapered top surface extending to a terminal end of the fin.

17. The polyaxial bone fixation assembly of claim 9, wherein the plurality of non-circumferential fins are deflectable so that each of the plurality of non-circumferential fins are interposed between the threads when the at least one fastener is inserted into the at least one opening.

18. The polyaxial bone fixation assembly of claim 9, wherein the plurality of non-circumferential fins are deformable so that each of the plurality of non-circumferential fins are interposed between the threads when the at least one fastener is inserted into the at least one opening.

\* \* \* \* \*